(12) United States Patent
Doshi et al.

(10) Patent No.: US 8,985,116 B2
(45) Date of Patent: Mar. 24, 2015

(54) LAYERED NASAL DEVICES

(75) Inventors: Rajiv Doshi, Belmont, CA (US); Bryan Loomas, Los Gatos, CA (US); Ryan Kendall Pierce, Carl Junction, MO (US); Arthur Ferdinand, San Jose, CA (US); Arthur G. Sandoval, San Francisco, CA (US); Jeffrey W. Servaites, San Francisco, CA (US); Matthew Durack, San Francisco, CA (US); Daniel Francis Kennedy, San Francisco, CA (US)

(73) Assignee: Theravent, Inc., San Jose, CA (US)

( * ) Notice: Subject to any disclaimer, the term of this patent is extended or adjusted under 35 U.S.C. 154(b) by 1376 days.

(21) Appl. No.: 11/759,916

(22) Filed: Jun. 7, 2007

(65) Prior Publication Data

US 2007/0283962 A1 Dec. 13, 2007

Related U.S. Application Data

(60) Provisional application No. 60/905,850, filed on Mar. 7, 2007, provisional application No. 60/859,715, filed on Nov. 16, 2006, provisional application No. 60/811,814, filed on Jun. 7, 2006.

(51) Int. Cl.
*A61M 11/00* (2006.01)
*A61M 16/06* (2006.01)
(Continued)

(52) U.S. Cl.
CPC . *A62B 23/06* (2013.01); *A61F 5/08* (2013.01); *A61M 16/0688* (2014.02); *A61M 16/0866* (2014.02); *A61M 15/08* (2013.01); *A61M 16/208* (2013.01); *A61F 5/56* (2013.01); *A61M 16/106* (2014.02)

USPC .................................. 128/207.18; 128/848

(58) Field of Classification Search
USPC ............ 128/207.12, 206.27, 206.25, 206.21, 128/206.23, 200.24, 201.18, 205.27, 128/205.29, 206.11, 206.12, 206.14, 128/206.15, 206.18, 207.18
See application file for complete search history.

(56) References Cited

U.S. PATENT DOCUMENTS 69,396 A 10/1867 Curtis
628,111 A 7/1899 McHatton
(Continued)

FOREIGN PATENT DOCUMENTS

EP 0434258 A2 6/1991
EP 1157663 A1 11/2001
(Continued)

OTHER PUBLICATIONS

Doshi et al.; U.S. Appl. No. 12/884,140 entitled "Sealing nasal devices for use while sleeping," filed Sep. 16, 2010.
(Continued)

*Primary Examiner* — Steven Douglas
(74) *Attorney, Agent, or Firm* — Shay Glenn LLP

(57) ABSTRACT

Described herein are nasal devices. In particular, layered nasal respiratory devices are described. Layered nasal device may include a layered airflow resistor that is configured to resist airflow in a first direction more than airflow in a second direction and that includes a flap valve adjacent to a flap valve limiting layer and an adhesive holdfast layer that is configured to secure the layered airflow resistor in communication with the subject's nasal cavity. Methods of using and methods of assembling layered nasal device are also described.

40 Claims, 64 Drawing Sheets

(51) Int. Cl.
*A62B 23/06* (2006.01)
*A61M 16/08* (2006.01)
*A61M 16/20* (2006.01)
*A61M 16/10* (2006.01)
*A61F 5/08* (2006.01)
*A61M 15/08* (2006.01)
*A61F 5/56* (2006.01)

(56) References Cited

U.S. PATENT DOCUMENTS

| | | |
|---|---|---|
| 669,098 A | 3/1901 | Overshiner |
| 675,275 A | 5/1901 | Gunning |
| 718,785 A | 1/1903 | McNary |
| 746,869 A | 12/1903 | Moulton |
| 774,446 A | 11/1904 | Moulton |
| 810,617 A | 1/1906 | Carence |
| 1,819,884 A | 8/1931 | Fores |
| 2,198,959 A | 4/1940 | Clarke |
| 2,237,954 A | 4/1941 | Wilson |
| 2,264,153 A | 11/1941 | Rowe |
| 2,274,886 A | 3/1942 | Carroll |
| 2,282,681 A | 5/1942 | Stotz |
| 2,335,936 A | 12/1943 | Hanlon |
| 2,433,565 A | 12/1947 | Korman |
| 2,448,724 A | 9/1948 | McGovney |
| 2,593,315 A | 4/1952 | Kraft |
| 2,672,138 A | 3/1954 | Carlock |
| 2,751,906 A | 6/1956 | Irvine |
| 2,777,442 A | 1/1957 | Zelano |
| 3,145,711 A | 8/1964 | Beber |
| 3,315,701 A | 4/1967 | Stilwell |
| 3,370,305 A | 2/1968 | Goott et al. |
| 3,451,392 A | 6/1969 | Cook et al. |
| 3,463,149 A | 8/1969 | Albu |
| 3,513,839 A | 5/1970 | Vacante |
| 3,556,122 A | 1/1971 | Laerdal |
| 3,616,802 A * | 11/1971 | Marinaccio ............... 131/339 |
| 3,657,855 A | 4/1972 | Swezey |
| 3,695,265 A | 10/1972 | Brevik |
| 3,710,799 A | 1/1973 | Caballero |
| 3,722,509 A | 3/1973 | Nebel |
| 3,747,597 A | 7/1973 | Olivera |
| 3,802,426 A | 4/1974 | Sakamoto |
| 3,884,223 A | 5/1975 | Keindl |
| 3,902,621 A | 9/1975 | Hidding |
| 4,004,584 A | 1/1977 | Geaney |
| 4,030,491 A | 6/1977 | Mattila |
| 4,040,428 A | 8/1977 | Clifford |
| 4,054,134 A | 10/1977 | Kritzer |
| 4,062,358 A | 12/1977 | Kritzer |
| 4,094,316 A | 6/1978 | Nathanson |
| 4,143,872 A | 3/1979 | Havstad et al. |
| 4,212,296 A | 7/1980 | Schaar |
| 4,220,150 A | 9/1980 | King |
| 4,221,217 A | 9/1980 | Amezcua |
| 4,226,233 A | 10/1980 | Kritzer |
| 4,240,420 A | 12/1980 | Riaboy |
| 4,267,831 A | 5/1981 | Aguilar |
| 4,327,719 A | 5/1982 | Childers |
| RE31,040 E | 9/1982 | Possis |
| 4,354,489 A | 10/1982 | Riaboy |
| 4,403,616 A | 9/1983 | King |
| 4,456,016 A | 6/1984 | Nowacki et al. |
| 4,487,207 A | 12/1984 | Fitz |
| 4,533,137 A | 8/1985 | Sonne |
| 4,582,058 A | 4/1986 | Depel et al. |
| 4,584,997 A | 4/1986 | Delong |
| 4,601,465 A | 7/1986 | Roy |
| 4,640,277 A | 2/1987 | Meyer et al. |
| 4,651,873 A | 3/1987 | Stolcenberg et al. |
| 4,702,374 A | 10/1987 | Kelner |
| 4,718,554 A | 1/1988 | Barbato |
| 4,739,987 A | 4/1988 | Nicholson |
| 4,822,354 A | 4/1989 | Elosegui |
| 4,854,574 A | 8/1989 | Larson et al. |
| 4,860,766 A | 8/1989 | Sackner |
| 4,862,903 A | 9/1989 | Campbell |
| 4,908,028 A | 3/1990 | Colon et al. |
| 4,913,138 A | 4/1990 | Yoshida et al. |
| 4,919,138 A | 4/1990 | Nordenstroom |
| 4,973,047 A | 11/1990 | Norell |
| 4,979,505 A | 12/1990 | Cox |
| 4,984,302 A | 1/1991 | Lincoln |
| 4,984,581 A | 1/1991 | Stice |
| 5,016,425 A | 5/1991 | Weick |
| 5,033,312 A | 7/1991 | Stupecky |
| 5,038,621 A | 8/1991 | Stupecky |
| 5,052,400 A | 10/1991 | Dietz |
| 5,059,208 A | 10/1991 | Coe et al. |
| 5,074,293 A | 12/1991 | Lott et al. |
| 5,078,739 A | 1/1992 | Martin |
| 5,092,781 A | 3/1992 | Casciotti et al. |
| 5,117,820 A | 6/1992 | Robitaille |
| 5,197,980 A | 3/1993 | Gorshkov et al. |
| 5,255,687 A | 10/1993 | McKenna |
| 5,383,470 A | 1/1995 | Kolbly |
| 5,385,542 A | 1/1995 | Rawlings |
| 5,391,205 A | 2/1995 | Knight |
| 5,392,773 A | 2/1995 | Bertrand |
| 5,394,867 A | 3/1995 | Swann |
| 5,414,627 A | 5/1995 | Wada et al. |
| 5,415,660 A | 5/1995 | Campbell et al. |
| 5,425,359 A | 6/1995 | Liou |
| 5,459,544 A | 10/1995 | Emura |
| 5,522,382 A | 6/1996 | Sullivan et al. |
| 5,535,739 A | 7/1996 | Rapoport et al. |
| 5,562,641 A | 10/1996 | Flomenblit et al. |
| 5,568,808 A | 10/1996 | Rimkus |
| 5,572,994 A | 11/1996 | Smith |
| 5,607,469 A | 3/1997 | Frey |
| 5,649,533 A | 7/1997 | Oren |
| 5,665,104 A | 9/1997 | Lee |
| 5,727,546 A * | 3/1998 | Clarke et al. ............. 128/203.15 |
| 5,730,122 A | 3/1998 | Lurie |
| 5,740,798 A | 4/1998 | McKinney |
| 5,743,256 A | 4/1998 | Jalowayski |
| 5,763,979 A | 6/1998 | Mukherjee et al. |
| 5,775,335 A | 7/1998 | Seal |
| 5,782,896 A | 7/1998 | Chen et al. |
| 5,797,920 A | 8/1998 | Kim |
| 5,803,121 A | 9/1998 | Estes |
| 5,823,187 A | 10/1998 | Estes et al. |
| 5,848,590 A | 12/1998 | Smith |
| 5,865,170 A | 2/1999 | Moles |
| 5,876,434 A | 3/1999 | Flomenblit et al. |
| 5,890,998 A | 4/1999 | Hougen |
| 5,899,832 A | 5/1999 | Hougen |
| 5,910,071 A | 6/1999 | Hougen |
| 5,911,756 A | 6/1999 | Debry |
| 5,947,119 A | 9/1999 | Reznick |
| 5,954,766 A | 9/1999 | Zadno-Azizi et al. |
| 5,957,978 A | 9/1999 | Blom |
| 5,992,006 A | 11/1999 | Datsikas |
| 6,004,342 A | 12/1999 | Filis |
| 6,058,932 A | 5/2000 | Hughes |
| 6,083,141 A | 7/2000 | Hougen |
| D430,667 S | 9/2000 | Rome |
| 6,119,690 A | 9/2000 | Pantaleo |
| 6,165,133 A | 12/2000 | Rapoport et al. |
| 6,177,482 B1 | 1/2001 | Cinelli et al. |
| 6,189,532 B1 | 2/2001 | Hely et al. |
| 6,213,955 B1 | 4/2001 | Karakasoglu et al. |
| 6,219,997 B1 | 4/2001 | Friberg et al. |
| 6,258,100 B1 | 7/2001 | Alferness et al. |
| 6,287,290 B1 | 9/2001 | Perkins et al. |
| 6,293,951 B1 | 9/2001 | Alferness et al. |
| 6,311,839 B1 | 11/2001 | Lo |
| 6,328,038 B1 | 12/2001 | Kessler et al. |
| 6,369,126 B1 | 4/2002 | Cinelli et al. |
| 6,398,775 B1 | 6/2002 | Perkins et al. |
| 6,439,233 B1 | 8/2002 | Geertsema |
| 6,484,725 B1 | 11/2002 | Chi |
| 6,500,095 B1 | 12/2002 | Hougen |

(56) References Cited

U.S. PATENT DOCUMENTS

| | | | |
|---|---|---|---|
| 6,510,846 B1 | 1/2003 | O'Rourke | |
| 6,527,761 B1 | 3/2003 | Soltesz et al. | |
| 6,561,188 B1 | 5/2003 | Ellis | |
| 6,562,057 B2 | 5/2003 | Santin | |
| 6,568,387 B2 | 5/2003 | Davenport et al. | |
| 6,573,421 B1 | 6/2003 | Lemaire | |
| 6,581,598 B1 | 6/2003 | Foran et al. | |
| 6,585,639 B1 | 7/2003 | Kotmel et al. | |
| 6,592,594 B2 | 7/2003 | Rimbaugh et al. | |
| 6,592,995 B2 | 7/2003 | Topolkaraev et al. | |
| 6,595,215 B2 | 7/2003 | Wood | |
| 6,609,516 B2 | 8/2003 | Hollander et al. | |
| 6,626,172 B1 | 9/2003 | Karow et al. | |
| 6,626,179 B1 | 9/2003 | Pedley | |
| 6,631,721 B1 | 10/2003 | Salter et al. | |
| 6,679,264 B1 | 1/2004 | Deem et al. | |
| 6,694,979 B2 | 2/2004 | Deem et al. | |
| 6,722,360 B2 | 4/2004 | Doshi | |
| 6,726,598 B1 | 4/2004 | Jarvis et al. | |
| 6,737,160 B1 | 5/2004 | Full et al. | |
| 6,769,432 B1 | 8/2004 | Keifer | |
| 6,776,162 B2 | 8/2004 | Wood | |
| 6,776,163 B2 | 8/2004 | Dougill et al. | |
| 6,811,538 B2 | 11/2004 | Westbrook et al. | |
| 6,841,716 B1 | 1/2005 | Tsutsumi | |
| 6,848,446 B2 | 2/2005 | Noble | |
| 6,863,066 B2 | 3/2005 | Ogle | |
| 6,866,652 B2 | 3/2005 | Bierman | |
| 6,872,439 B2 | 3/2005 | Fearing et al. | |
| 6,913,017 B2 | 7/2005 | Roberts | |
| 6,921,574 B2 | 7/2005 | Cinelli et al. | |
| 6,997,177 B2 | 2/2006 | Wood | |
| 7,011,723 B2 | 3/2006 | Full et al. | |
| 7,013,896 B2 | 3/2006 | Schmidt | |
| 7,047,969 B2 | 5/2006 | Noble | |
| 7,156,098 B2 | 1/2007 | Dolezal et al. | |
| 7,175,723 B2 | 2/2007 | Jones et al. | |
| 7,178,524 B2 | 2/2007 | Noble | |
| 7,201,169 B2 | 4/2007 | Wilkie et al. | |
| D542,407 S | 5/2007 | Stallard et al. | |
| 7,263,996 B2 | 9/2007 | Yung Ho | |
| D566,834 S | 4/2008 | Barton | |
| 7,422,014 B1 | 9/2008 | Smith | |
| 7,559,326 B2 | 7/2009 | Smith et al. | |
| 7,578,294 B2 | 8/2009 | Pierro et al. | |
| 7,640,934 B2 | 1/2010 | Zollinger et al. | |
| 7,880,051 B2 | 2/2011 | Madsen et al. | |
| 7,992,566 B2 | 8/2011 | Pflueger et al. | |
| 2001/0051799 A1 | 12/2001 | Ingenito | |
| 2001/0056274 A1 | 12/2001 | Perkins et al. | |
| 2002/0062120 A1 | 5/2002 | Perkins et al. | |
| 2002/0077593 A1 | 6/2002 | Perkins et al. | |
| 2002/0112729 A1 | 8/2002 | DeVore et al. | |
| 2002/0157673 A1 | 10/2002 | Kessler et al. | |
| 2003/0024527 A1 | 2/2003 | Ginn | |
| 2003/0050648 A1 | 3/2003 | Alferness et al. | |
| 2003/0070682 A1 | 4/2003 | Wilson et al. | |
| 2003/0106555 A1 | 6/2003 | Tovey | |
| 2003/0106556 A1 | 6/2003 | Alperovich et al. | |
| 2003/0140925 A1 | 7/2003 | Sapienza et al. | |
| 2003/0149387 A1 | 8/2003 | Barakat et al. | |
| 2003/0154988 A1 | 8/2003 | DeVore et al. | |
| 2003/0158515 A1 | 8/2003 | Gonzalez et al. | |
| 2003/0195552 A1 | 10/2003 | Santin | |
| 2003/0209247 A1 | 11/2003 | O'Rourke | |
| 2004/0016432 A1 | 1/2004 | Genger et al. | |
| 2004/0020489 A1 | 2/2004 | Gillespie et al. | |
| 2004/0020492 A1 | 2/2004 | Dubrul et al. | |
| 2004/0020493 A1 | 2/2004 | Wood | |
| 2004/0055606 A1 | 3/2004 | Hendricksen et al. | |
| 2004/0112379 A1 | 6/2004 | Djupesland | |
| 2004/0123868 A1* | 7/2004 | Rutter | 128/207.14 |
| 2004/0149615 A1 | 8/2004 | Eisenbraun | |
| 2004/0194779 A1 | 10/2004 | Doshi | |
| 2004/0254491 A1 | 12/2004 | Ricciardelli | |
| 2004/0261791 A1 | 12/2004 | Horian | |
| 2004/0261798 A1 | 12/2004 | Rimkus | |
| 2005/0010125 A1 | 1/2005 | Joy et al. | |
| 2005/0011524 A1 | 1/2005 | Thomlinson et al. | |
| 2005/0033344 A1 | 2/2005 | Dillard et al. | |
| 2005/0051170 A1 | 3/2005 | Koo | |
| 2005/0066965 A1 | 3/2005 | Cronk et al. | |
| 2005/0133039 A1 | 6/2005 | Wood | |
| 2005/0279351 A1 | 12/2005 | Lewis et al. | |
| 2005/0284479 A1 | 12/2005 | Schrader et al. | |
| 2006/0000472 A1 | 1/2006 | Fenton | |
| 2006/0016450 A1 | 1/2006 | Pearson et al. | |
| 2006/0085027 A1 | 4/2006 | Santin et al. | |
| 2006/0144398 A1 | 7/2006 | Doshi et al. | |
| 2006/0150978 A1 | 7/2006 | Doshi et al. | |
| 2006/0150979 A1 | 7/2006 | Doshi et al. | |
| 2006/0169285 A1 | 8/2006 | Bovo | |
| 2006/0266361 A1 | 11/2006 | Hernandez | |
| 2006/0283461 A1 | 12/2006 | Lubke et al. | |
| 2007/0016123 A1 | 1/2007 | Jensen | |
| 2007/0051364 A1 | 3/2007 | Jacobson et al. | |
| 2007/0095349 A1 | 5/2007 | Hansmann et al. | |
| 2007/0175478 A1 | 8/2007 | Brunst | |
| 2007/0227542 A1 | 10/2007 | Kashmakov et al. | |
| 2007/0277832 A1 | 12/2007 | Doshi et al. | |
| 2007/0287976 A1 | 12/2007 | Sherrill | |
| 2007/0295338 A1 | 12/2007 | Loomas et al. | |
| 2008/0023007 A1 | 1/2008 | Dolezal et al. | |
| 2008/0032119 A1 | 2/2008 | Feldhahn et al. | |
| 2008/0041397 A1 | 2/2008 | Hirs | |
| 2008/0053460 A1 | 3/2008 | Wilson | |
| 2008/0087286 A1 | 4/2008 | Jones | |
| 2008/0099021 A1 | 5/2008 | Moore | |
| 2008/0135044 A1 | 6/2008 | Freitag et al. | |
| 2008/0142014 A1 | 6/2008 | Jiang | |
| 2009/0145441 A1 | 6/2009 | Doshi et al. | |
| 2009/0145788 A1 | 6/2009 | Doshi et al. | |
| 2009/0188493 A1 | 7/2009 | Doshi et al. | |
| 2009/0194100 A1 | 8/2009 | Minagi | |
| 2009/0194109 A1 | 8/2009 | Doshi et al. | |
| 2010/0326447 A1 | 12/2010 | Loomas et al. | |
| 2011/0005520 A1 | 1/2011 | Doshi et al. | |
| 2011/0005528 A1 | 1/2011 | Doshi et al. | |
| 2011/0005529 A1 | 1/2011 | Doshi et al. | |
| 2011/0005530 A1 | 1/2011 | Doshi et al. | |
| 2011/0240032 A1 | 10/2011 | Doshi | |
| 2011/0240038 A1 | 10/2011 | Doshi et al. | |
| 2012/0055488 A1 | 3/2012 | Pierce et al. | |

FOREIGN PATENT DOCUMENTS

| | | |
|---|---|---|
| EP | 1205203 A2 | 5/2002 |
| EP | 1481702 A2 | 12/2004 |
| FR | 2862614 A1 | 5/2005 |
| GB | 2096574 A | 10/1982 |
| GB | 2324729 A | 4/1998 |
| JP | 52-123786 A | 10/1977 |
| JP | 55-122742 U | 9/1980 |
| JP | 58-136345 A | 8/1983 |
| JP | 63-189257 U | 12/1988 |
| JP | 7-47126 | 2/1995 |
| JP | 3059270 U | 3/1999 |
| JP | 2001-299916 A | 10/2001 |
| JP | 2002-153489 A | 5/2002 |
| JP | 2002-219174 A | 8/2002 |
| JP | 2002-345963 A | 12/2002 |
| JP | 2002-345966 | 12/2002 |
| JP | 05/40589 A | 2/2005 |
| JP | 2005-505355 | 2/2005 |
| JP | 2008-136496 | 6/2008 |
| JP | 2008-522763 | 7/2008 |
| RU | 2048820 C1 | 11/1995 |
| SU | 1586709 A1 | 8/1990 |
| WO | WO 90/12614 A1 | 11/1990 |
| WO | WO 93/08777 A1 | 5/1993 |
| WO | WO 95/17220 A1 | 6/1995 |
| WO | WO 95/33520 A1 | 12/1995 |
| WO | WO 98/46310 A2 | 10/1998 |
| WO | WO 99/03395 A1 | 1/1999 |

(56) References Cited

FOREIGN PATENT DOCUMENTS

| | | |
|---|---|---|
| WO | WO 00/29066 A1 | 5/2000 |
| WO | WO 00/50121 A1 | 8/2000 |
| WO | WO 00/67848 A1 | 11/2000 |
| WO | WO 01/02042 A1 | 1/2001 |
| WO | WO 01/13839 A1 | 3/2001 |
| WO | WO 01/13908 A2 | 3/2001 |
| WO | WO 01/49371 A2 | 7/2001 |
| WO | WO 01/87170 A1 | 11/2001 |
| WO | WO 01/89381 A1 | 11/2001 |
| WO | WO 02/38038 A2 | 5/2002 |
| WO | WO 03/022124 A2 | 3/2003 |
| WO | WO 03/034927 A1 | 5/2003 |
| WO | WO 2004/084998 A1 | 10/2004 |
| WO | WO2005/000805 A2 | 1/2005 |
| WO | WO2006/040585 A1 | 4/2006 |
| WO | WO 2006/063339 A2 | 6/2006 |
| WO | WO2007/023607 | 3/2007 |
| WO | WO 2007/129814 A1 | 11/2007 |
| WO | WO 2007/134458 A1 | 11/2007 |
| WO | WO 2007/146133 A2 | 12/2007 |

OTHER PUBLICATIONS

Doshi et al.; U.S. Appl. No. 12/884,146 entitled "Nasal devices for use while sleeping," filed Sep. 16, 2010.

Doshi et al.; U.S. Appl. No. 12/955,633 entitled "Nasal respiratory devices," filed Nov. 29, 2010.

Sather et al.; U.S. Appl. No. 12/941,734 entitled "Nasal devices having a safe failure mode and remotely activatable," filed Nov. 8, 2010.

Doshi et al.; U.S. Appl. No. 12/711,782 entitled "Respiratory devices," filed Feb. 24, 2010.

Favet et al.; U.S. Appl. No. 13/035,524 entitled "Nasal devices including layered nasal devices and delayed resistance adapters for use with nasal devices," filed Feb. 25, 2011.

Lai et al.; U.S. Appl. No. 13/062,888 entitled "Nasal devices, systems and methods," filed Mar. 8, 2011.

Sather et al.; U.S. Appl. No. 12/044,868 entitled "Respiratory sensor adapters for nasal devices," filed Mar. 7, 2008.

Pierce et al.; U.S. Appl. No. 12/141,875 entitled "Adhesive nasal respiratory devices," filed Jun. 18, 2008.

Sather et al.; U.S. Appl. No. 12/405,837 entitled "Nasal devices with noise-reduction and methods of use," filed Mar. 17, 2009.

Ferdinand et al.; U.S. Appl. No. 12/485,750 entitled "Adjustable resistance nasal devices," filed Jun. 16, 2009.

Hakel et al.; Nasal obturator for velopharyngeal dysfunction in dysarthria: technical report on a one-way valve; Journal of Medical Speech-Language Pathology; vol. 12; No. 4; pp. 155-159; 2004.

Doshi et al.; U.S. Appl. No. 13/212,948 entitled "Packaging and dispensing nasal devices," filed Aug. 18, 2011.

Sather et al.; U.S. Appl. No. 13/117,933 entitled "Layered nasal respiratory devices," filed May 27, 2011.

Doshi et al., U.S. Appl. No. 13/545,865 entitled "Nasal Devices," filed Jul. 10, 2012.

Witt et al.; U.S. Appl. No. 61/141,251 entitled "System, Method, and Respiration Appliance for Supporting the Airway of a Subject," filed Dec. 30, 2008.

Doshi et al; U.S. Appl. No. 11/811,339 entitled "Nasal devices," filed Jun. 7, 2007.

Doshi et al; U.S. Appl. No. 11/941,913 entitled "Nasal device applicators," filed Nov. 16, 2007.

Doshi et al; U.S. Appl. No. 11/941,915 entitled "Adjustable nasal devices," filed Nov. 16, 2007.

Doshi, Rajiv; U.S. Appl. No. 12/014,060 entitled "Methods and devices for improving breathing in patients with pulmonary disease," filed Jan. 14, 2008.

Mahadevia, A. K. et al., Effects of expiratory positive airway pressure on sleep-induced respiratory abnormalities in patients with hypersomnia-sleep apnea syndrome, Am Rev Respir Dis 1983, vol. 128, pp. 708-711, Oct. 1983.

http://chinookmed.com/index.cfm/fa/product.display&Product_ID=275.

Dillard, D. et al., Evaluation of a novel intra-bronchial valve to produce lung volume reduction, World Congress of Bronchology, Jun. 2002 (figs. 1-4 available upon request).

\* cited by examiner

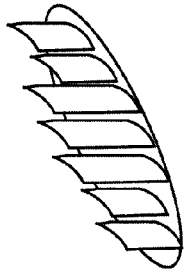
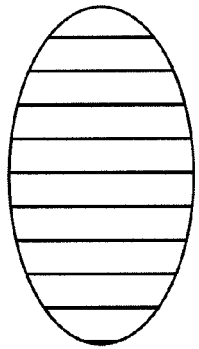
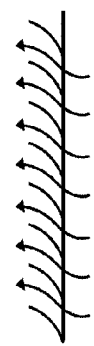
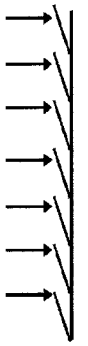
FIG. 2D    FIG. 2E    FIG. 2F    FIG. 2G
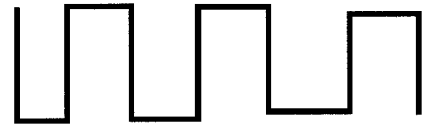
FIG. 2C
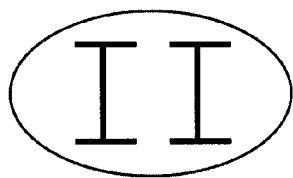
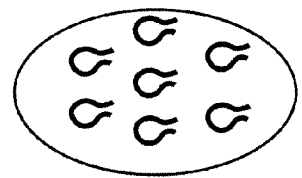
FIG. 2A    FIG. 2B

| | | Inspiratory Resistance | Expiratory Resistance |
|---|---|---|---|
| | | 0.6 | 22 |
| | | 0.4 | 5.3 |
| | | 0.6 | 8.2 |
| | | 1 | 9 |
| | | 0.2 | 7.4 |
| | | 1.4 | 13 |
| | | 0.3 | 11.4 |

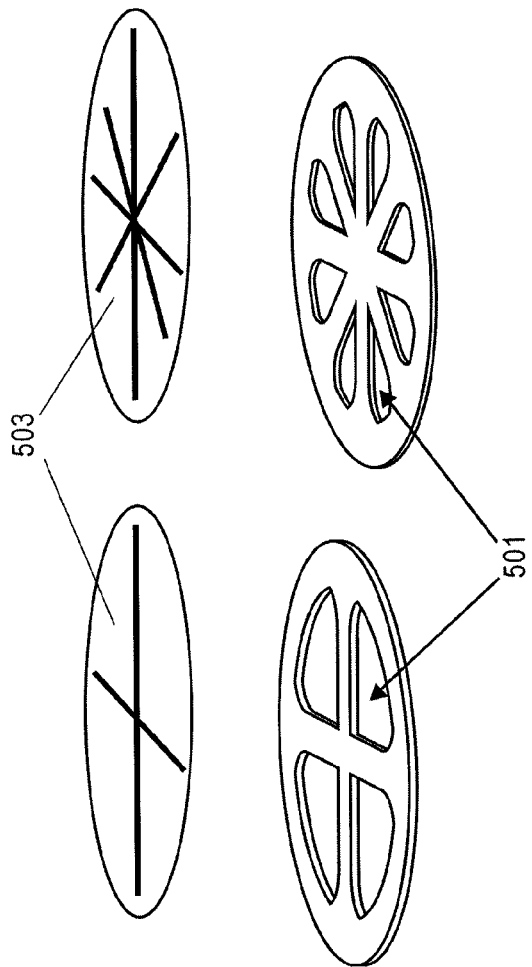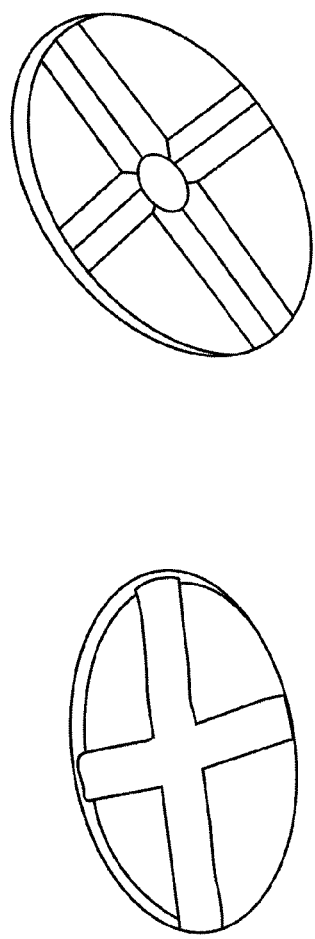
FIG. 5A
FIG. 5B
FIG. 5C

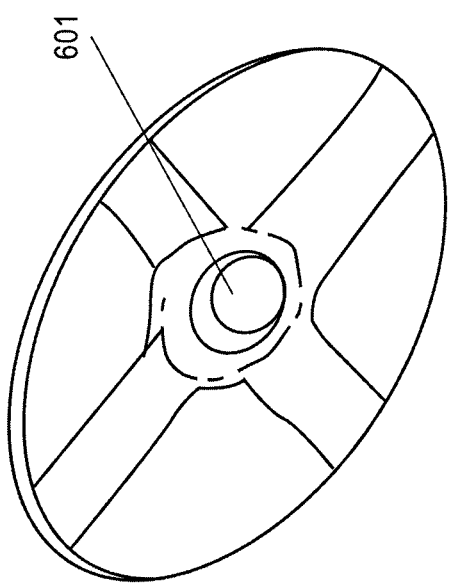
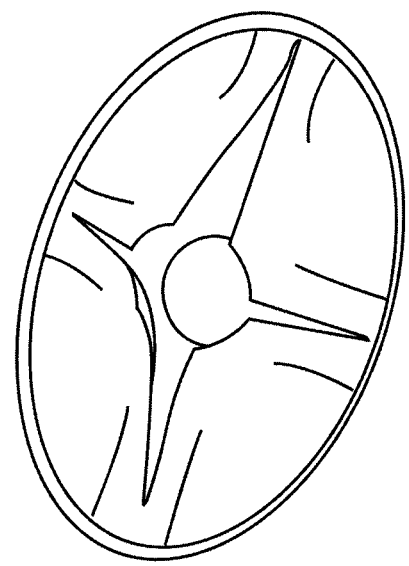
FIG. 6A
FIG. 6B

TOP

BOTTOM

AIRFLOW

SILICONE OPENS WHICH ALLOWS AIR TO LEAK, BUT SUPPLY A BACK PRESSURE

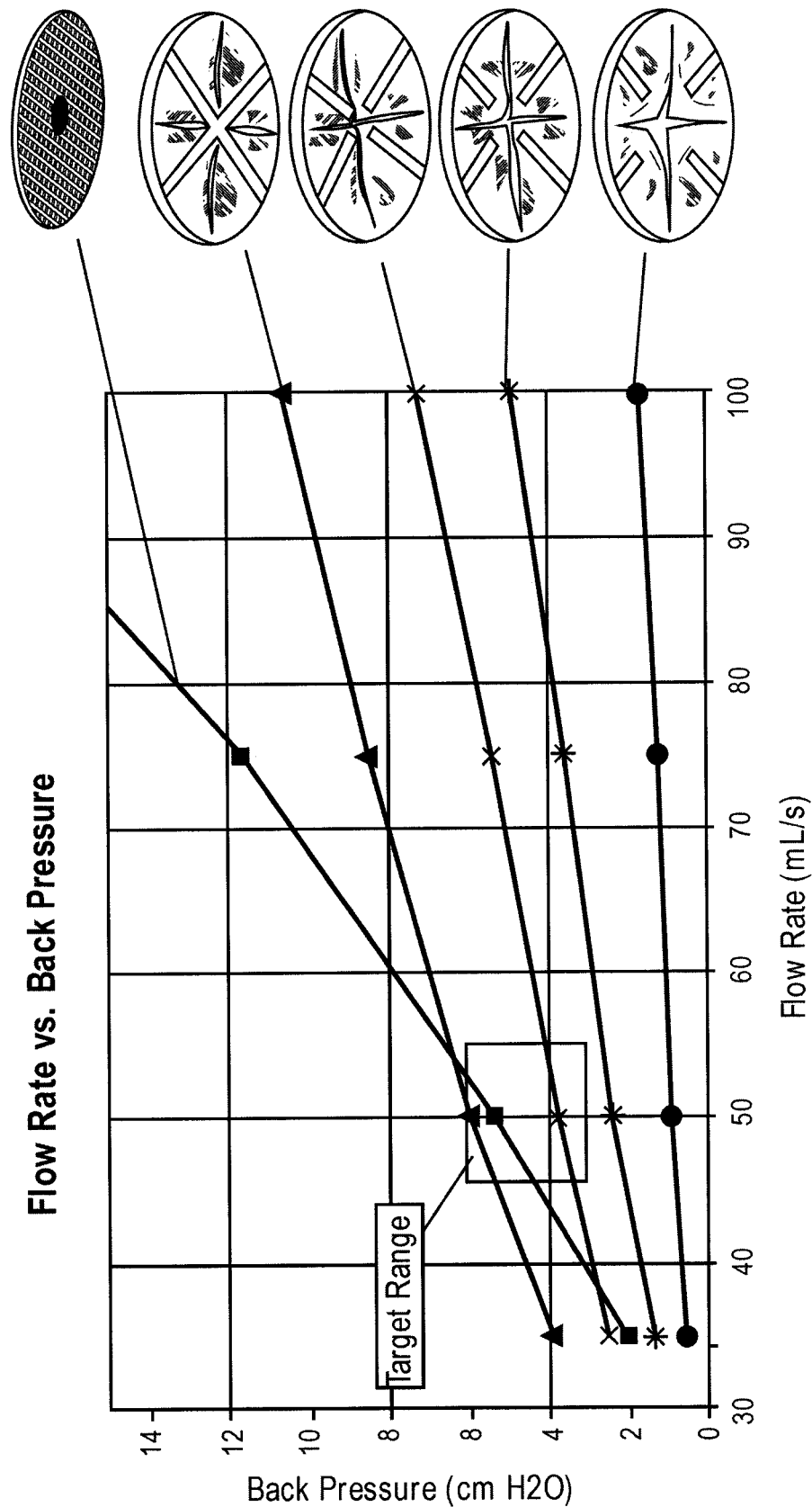

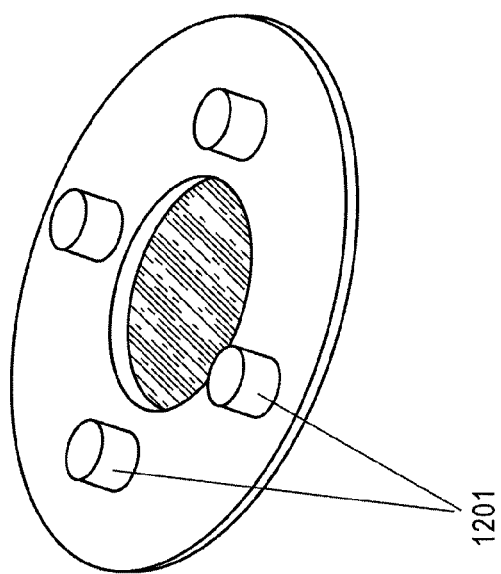
FIG. 12D
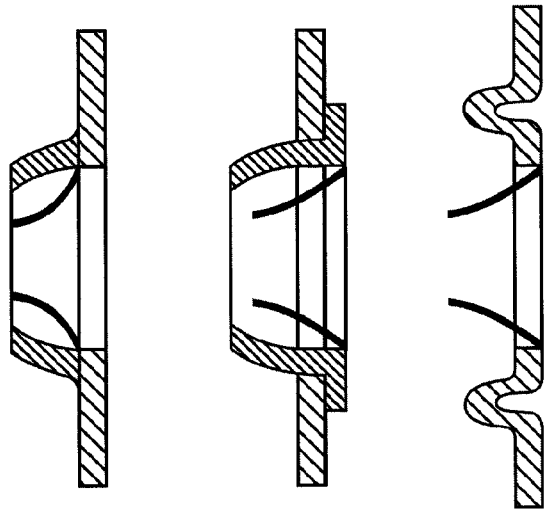
FIG. 12A
FIG. 12B
FIG. 12C

FIG. 17

| | A<br>FLAPPER GEOMETRY | B<br>ONE OR TWO | B<br>ALIGNMENT METHOD | C<br>MESH COVERAGE | D<br>MESH PLACEMENT |
|---|---|---|---|---|---|
| 1 | S-CURVE | SINGLE DEVICE | NONE | LOCAL | CONTINUOUS |
| 2 | FISH SCALES | BRIDGED | COLD FORMED CONE | FULL | PICK AND PLACE |
| 3 | PIE SLICES | FULL DEVICE | INJECTION MOLDED CONE | | |
| 4 | | | VISUAL ONLY | | |

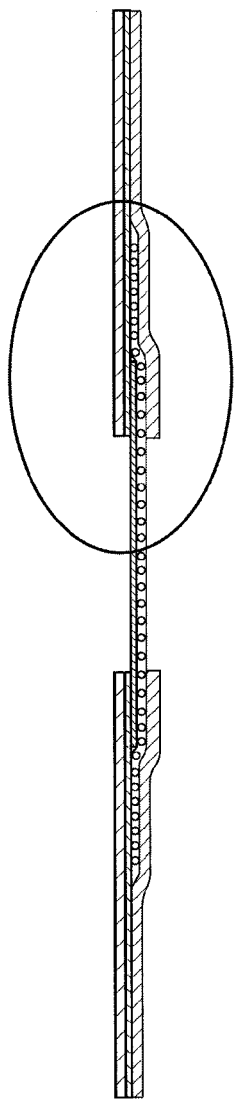
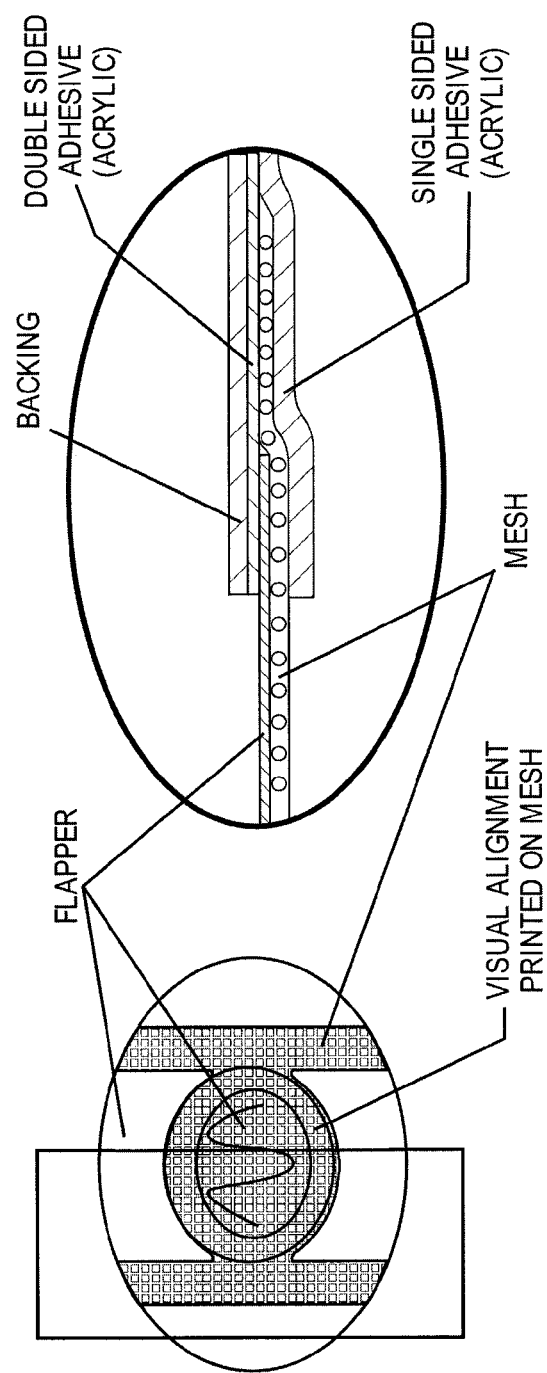
FIG. 19A
FIG. 19B

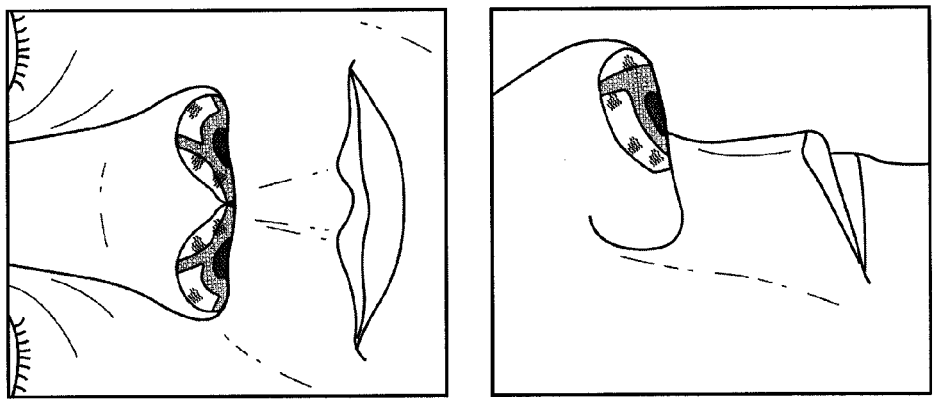
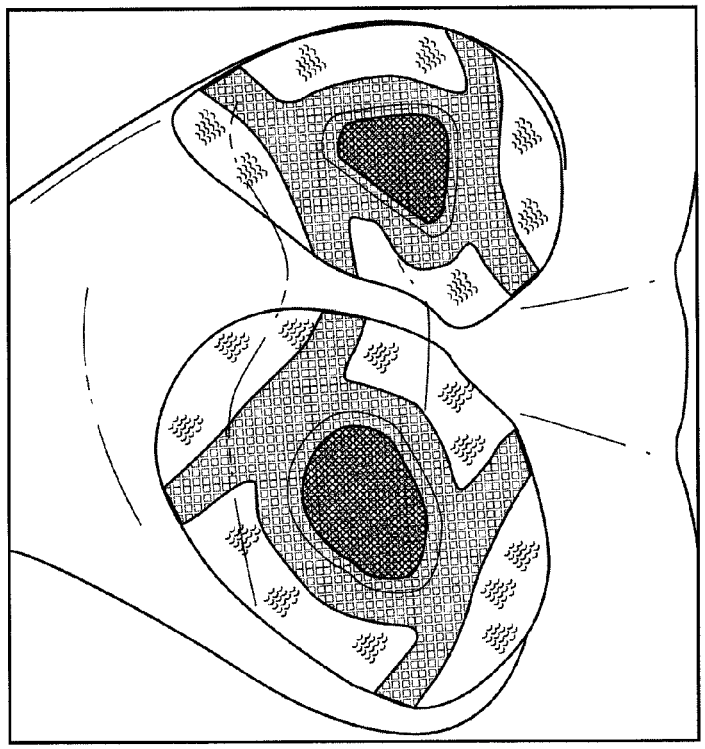
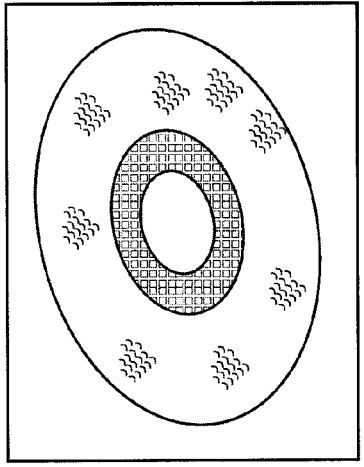

FIG. 20B1
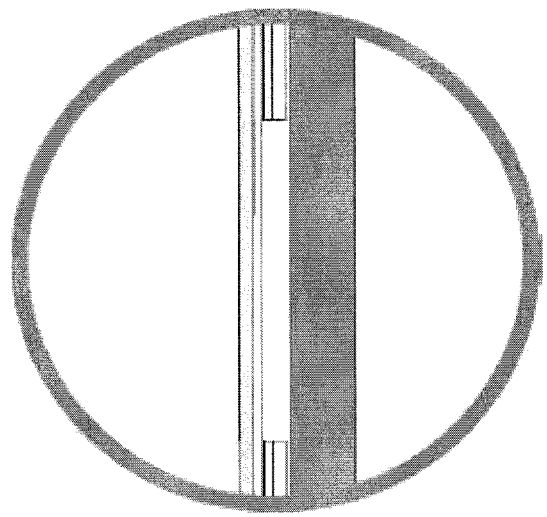
FIG. 20B
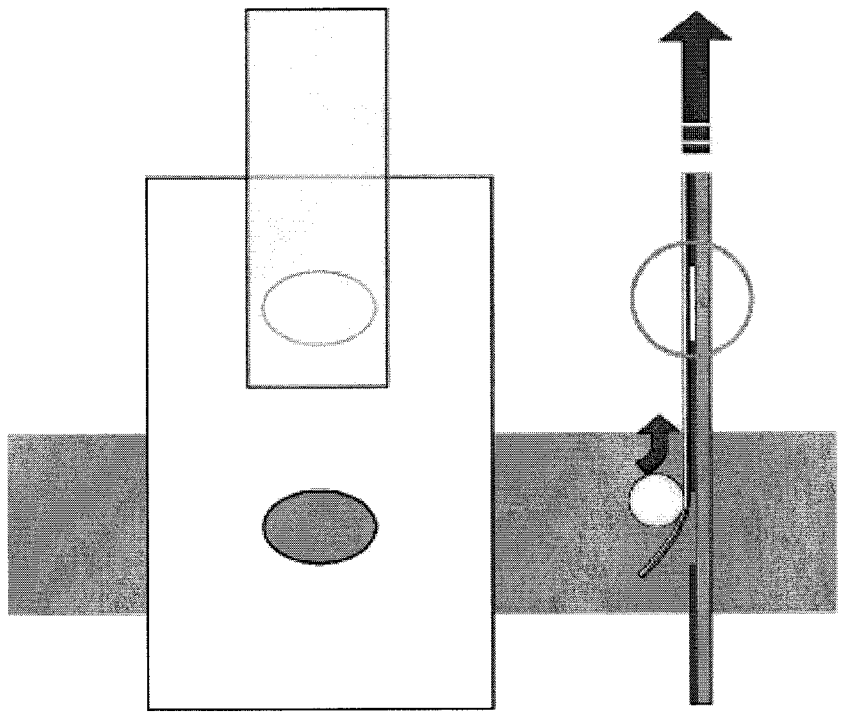

FIG. 20C1
FIG. 20C
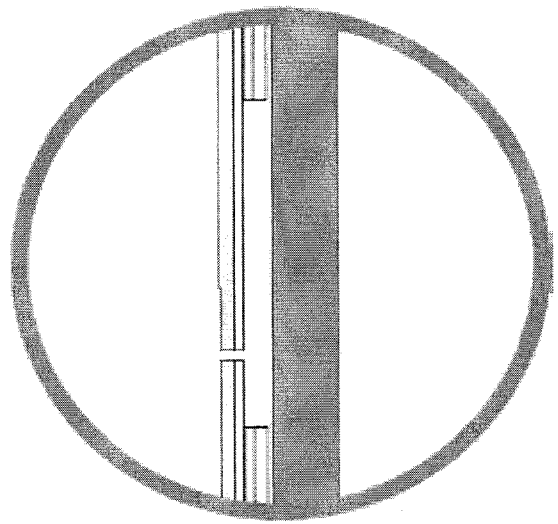
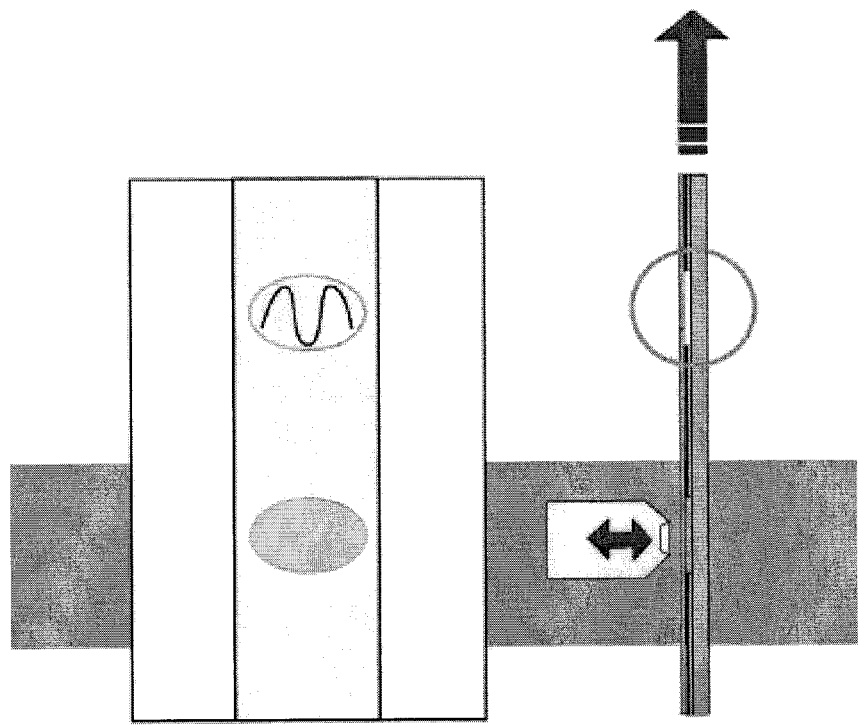

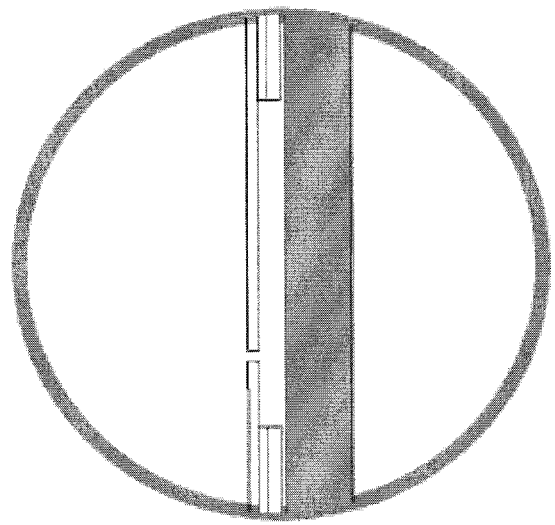
FIG. 20D1
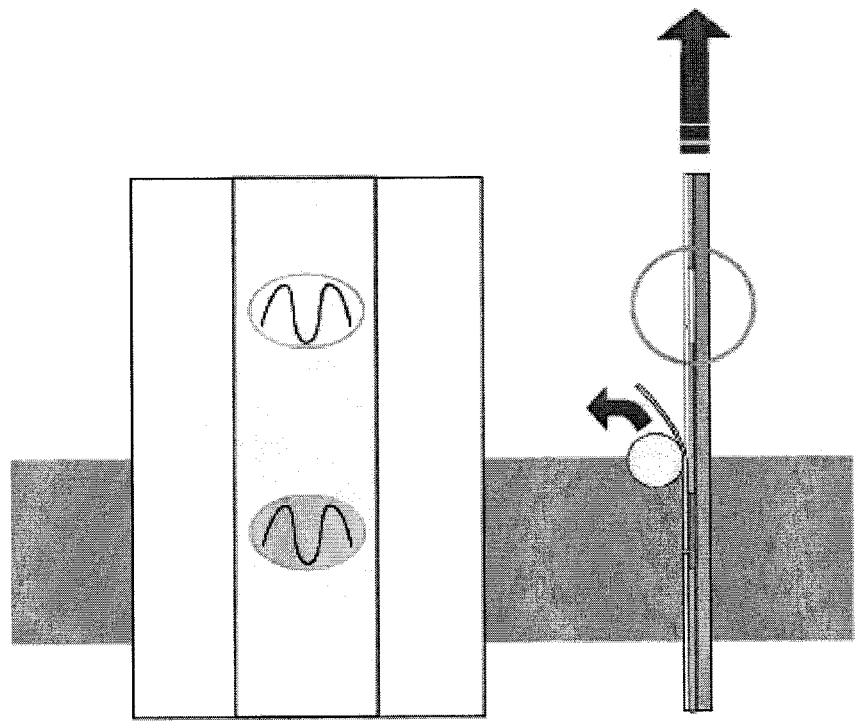
FIG. 20D

FIG. 20E1
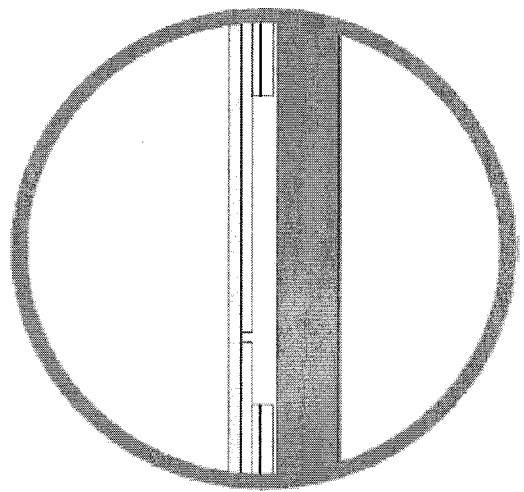
FIG. 20E
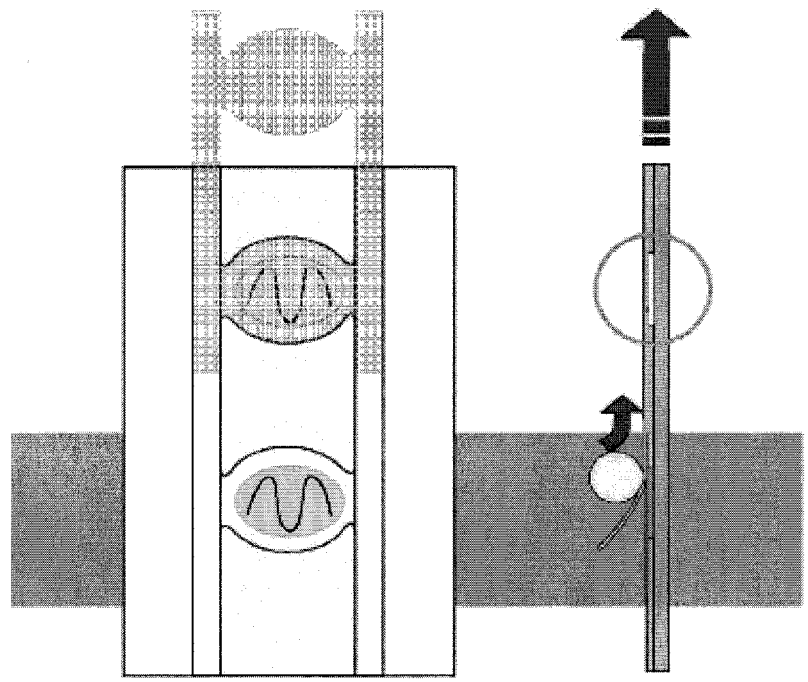

FIG. 20F1
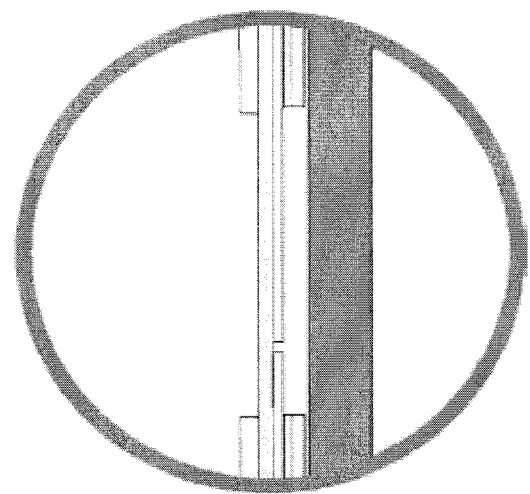
FIG. 20F
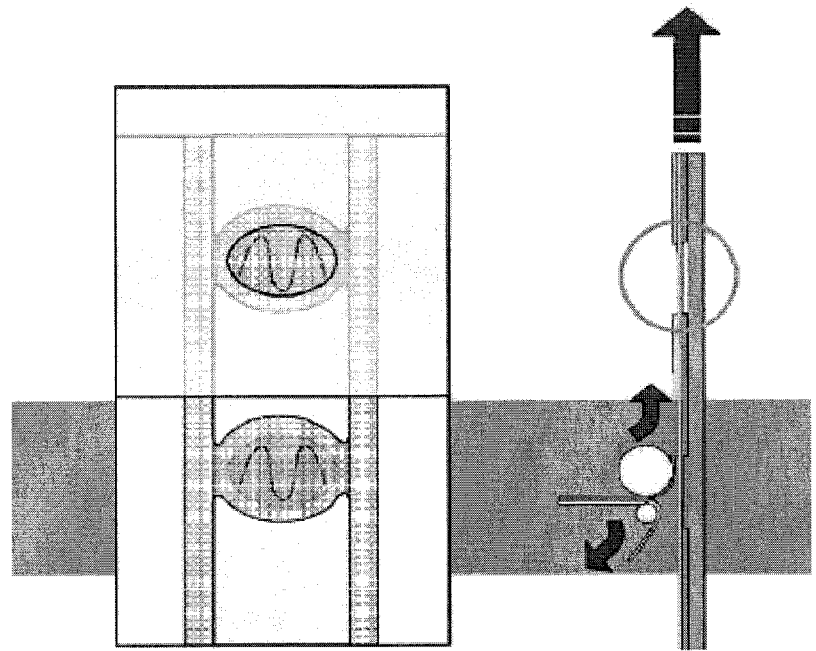

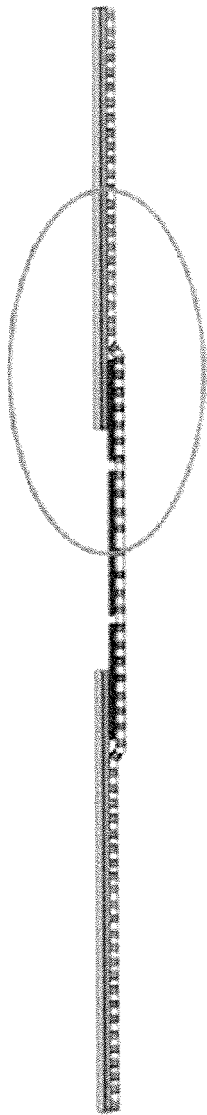
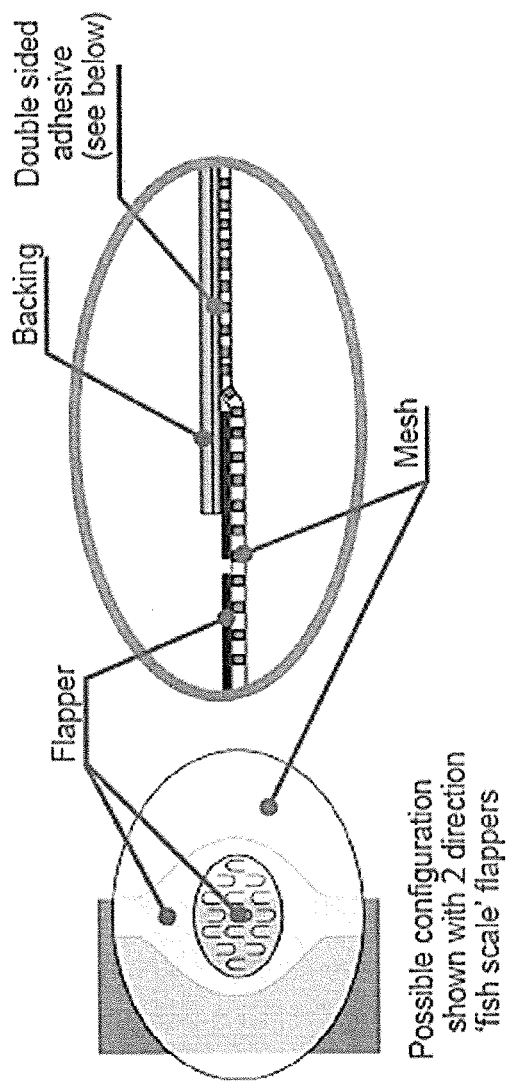
FIG. 21A
FIG. 21B

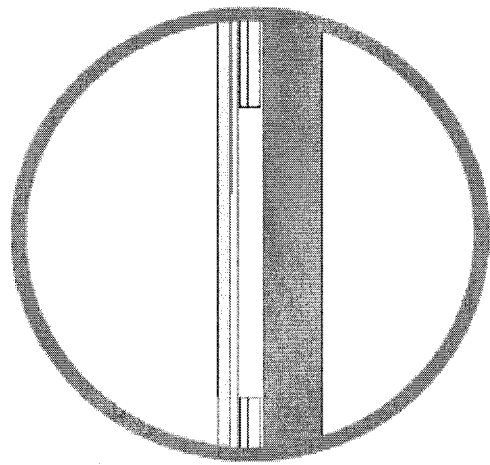
FIG. 22B1
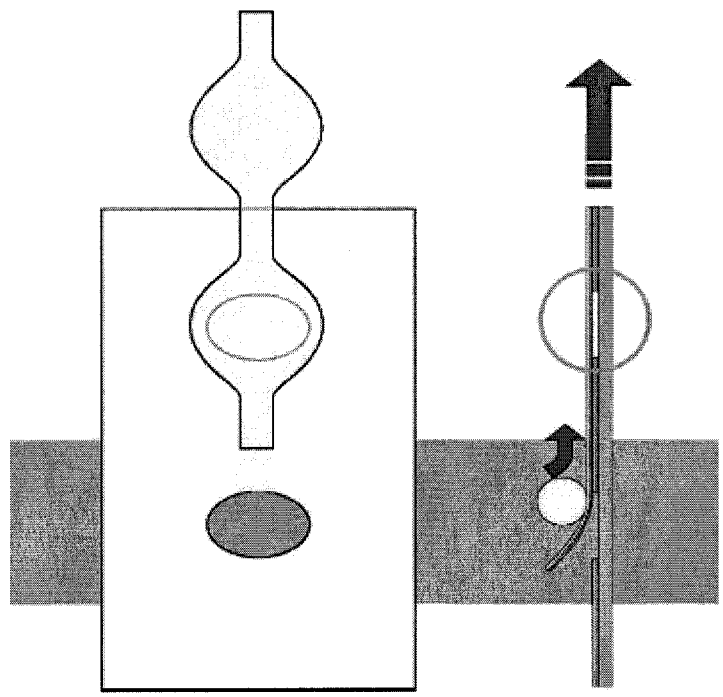
FIG. 22B

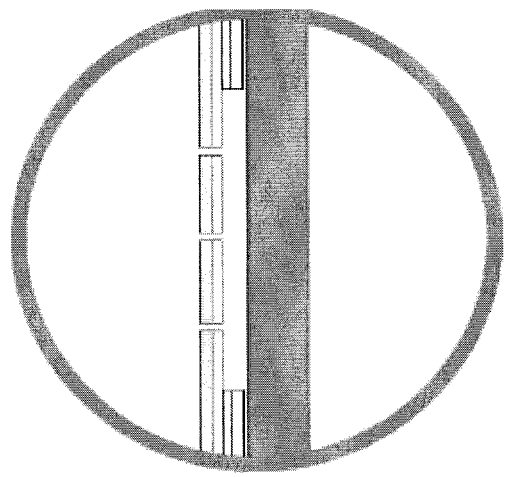
FIG. 22C1
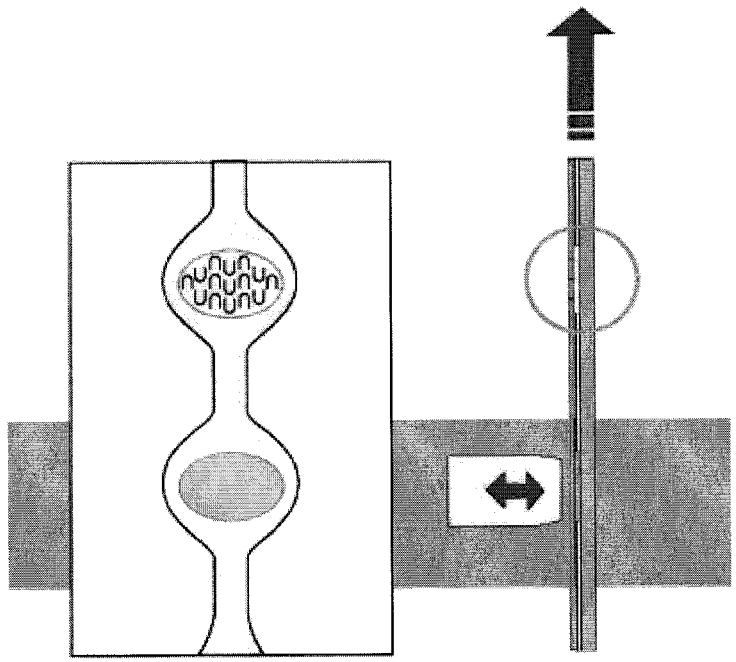
FIG. 22C

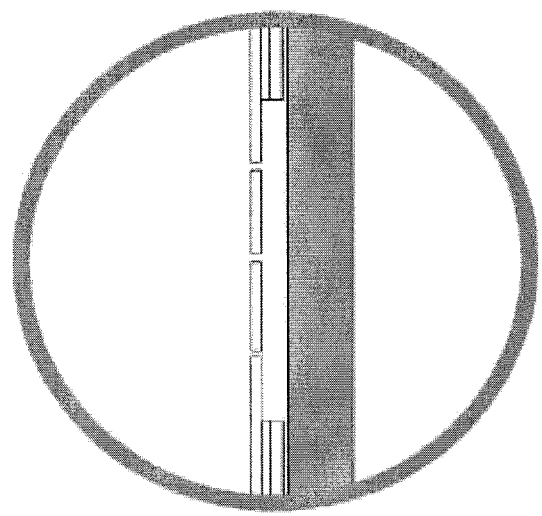
FIG. 22D1
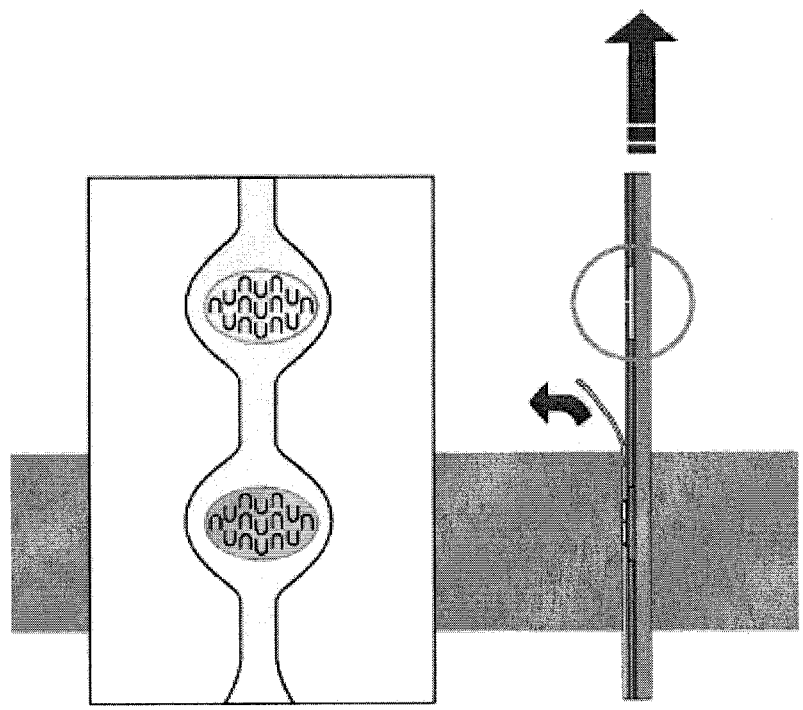
FIG. 22D

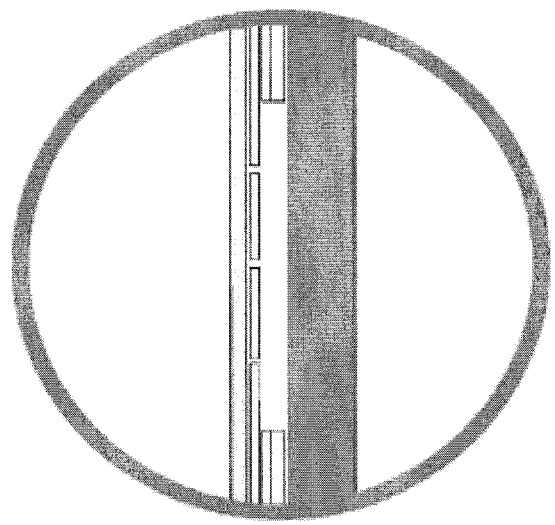
FIG. 22E1
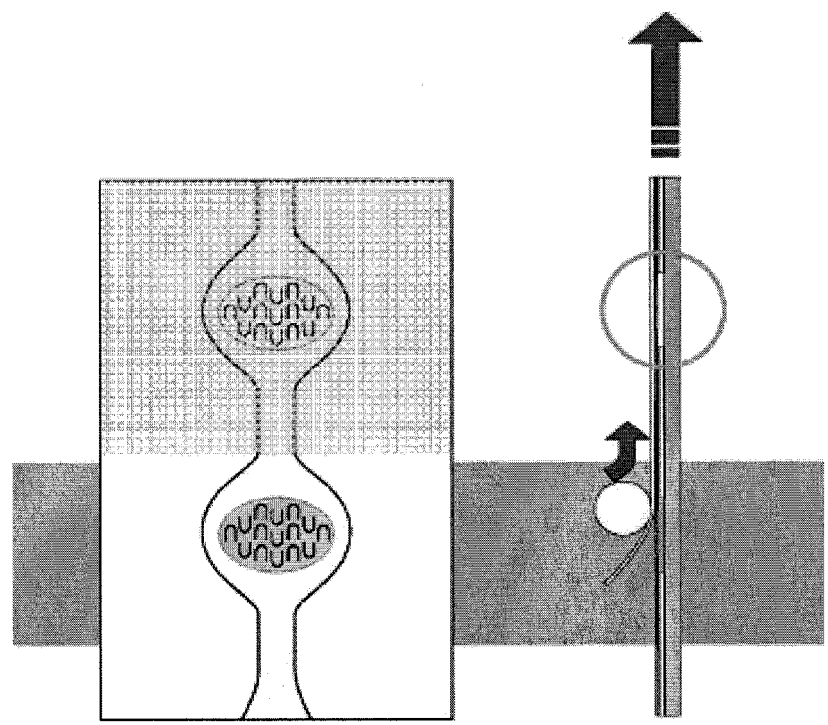
FIG. 22E

FIG. 24B1
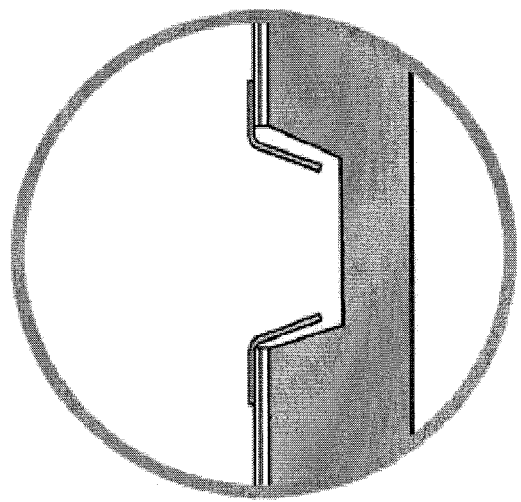
FIG. 24B
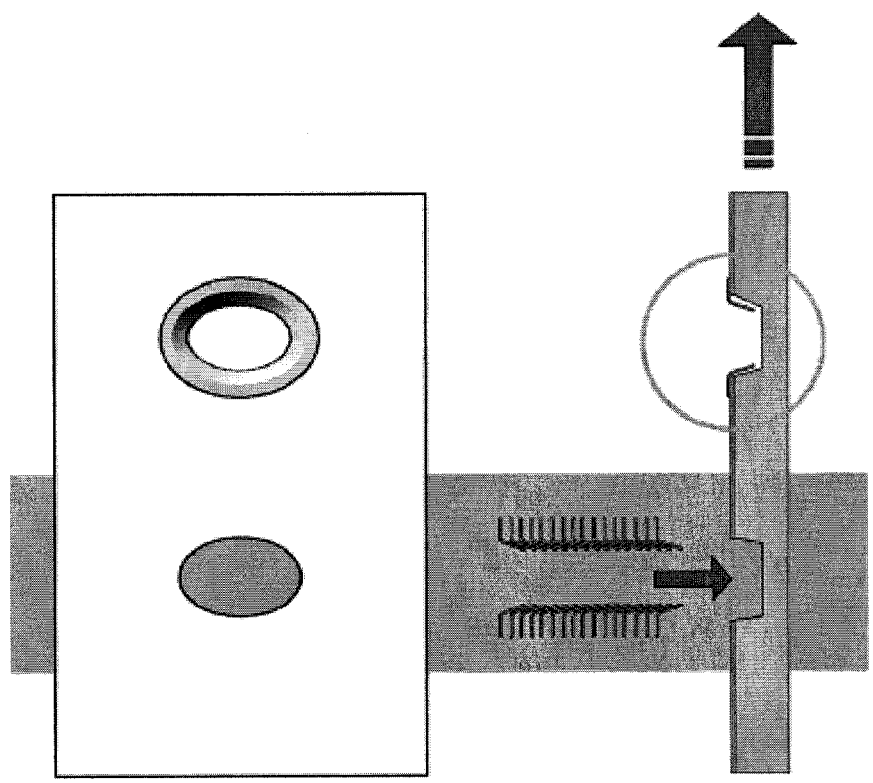

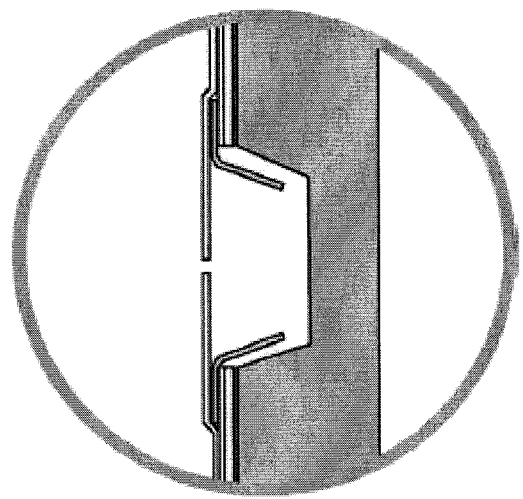
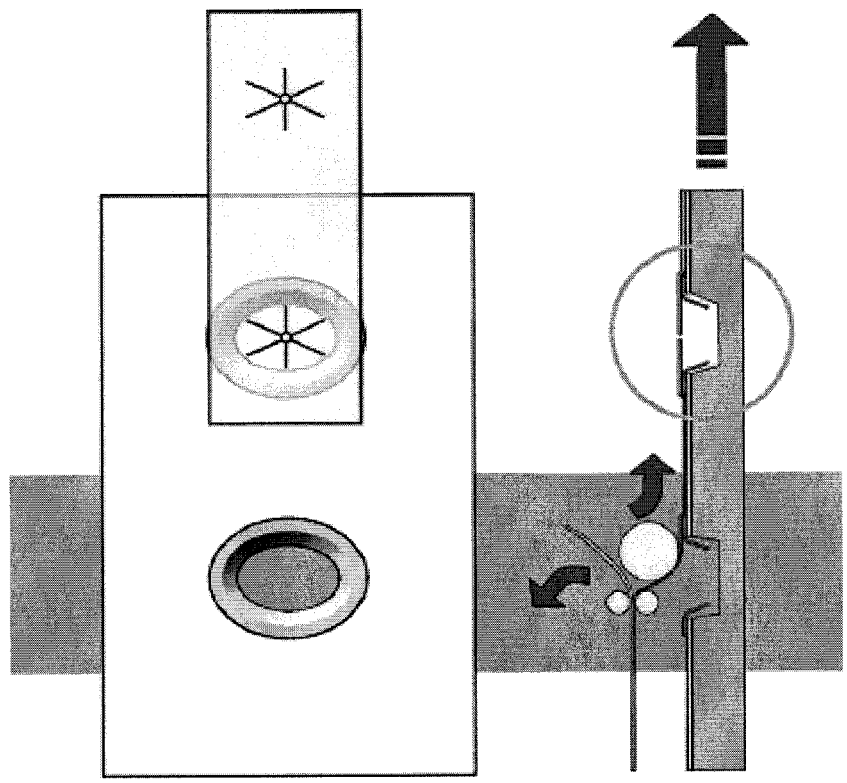
FIG. 24C1
FIG. 24C

FIG. 24D1
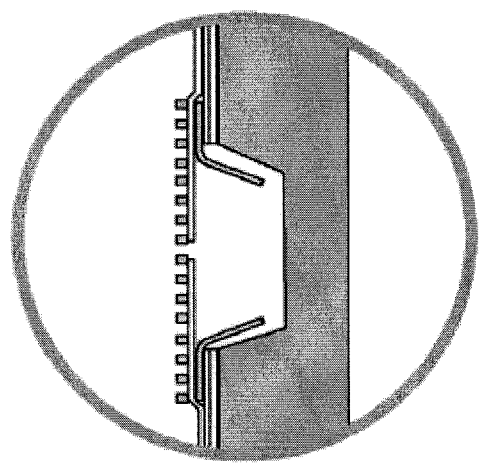
FIG. 24D
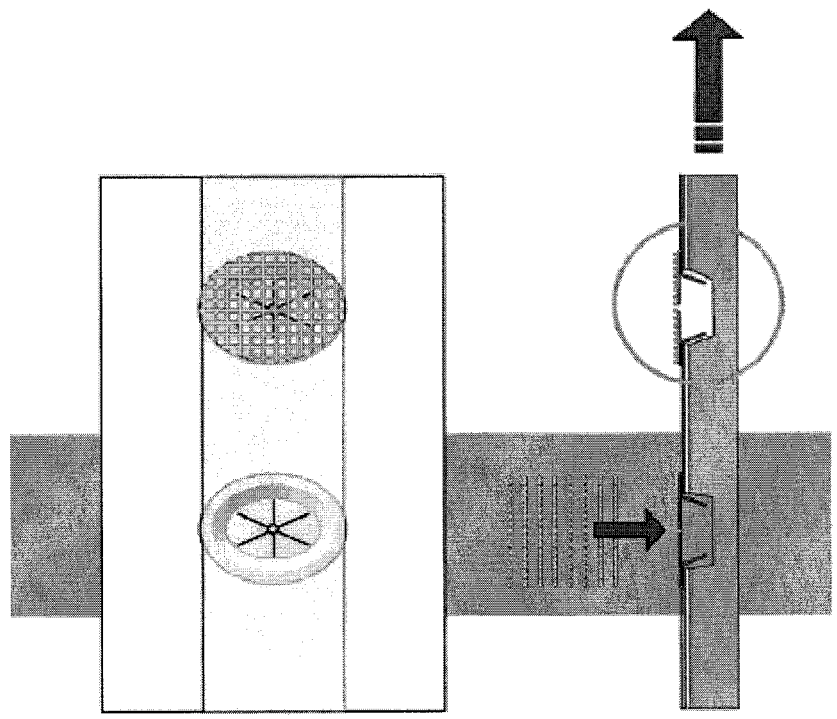

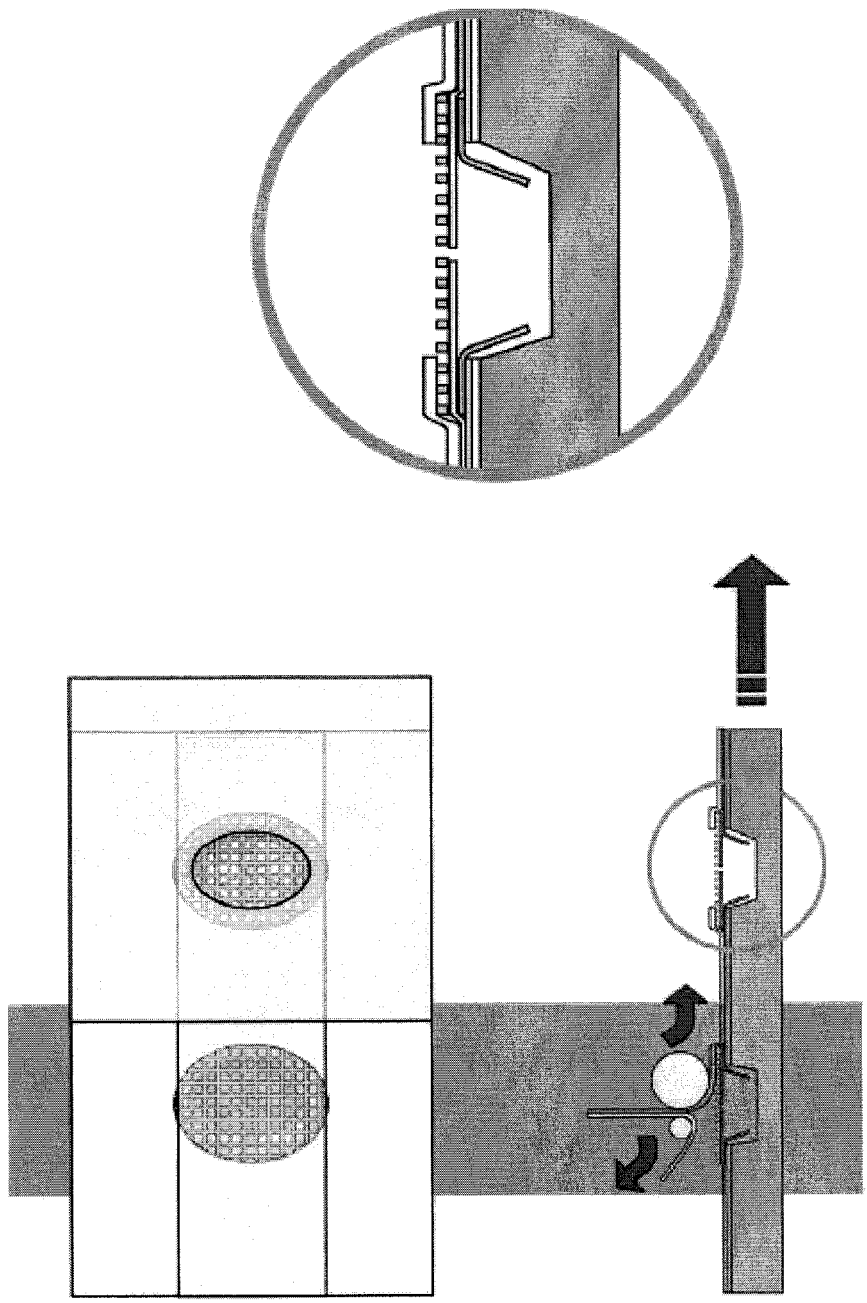

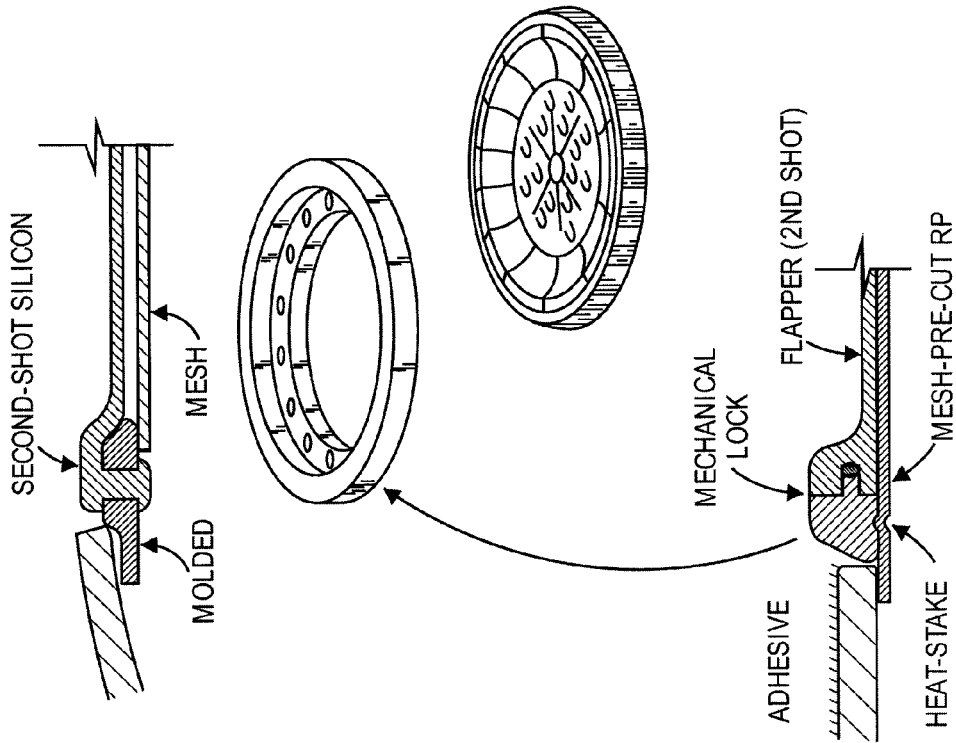

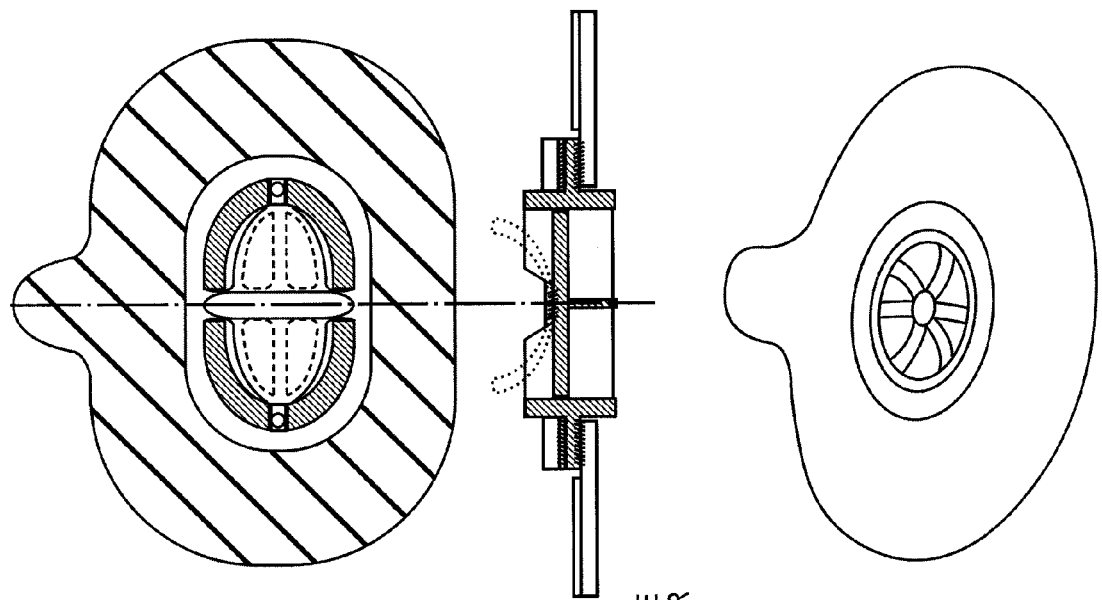
FIG. 28A
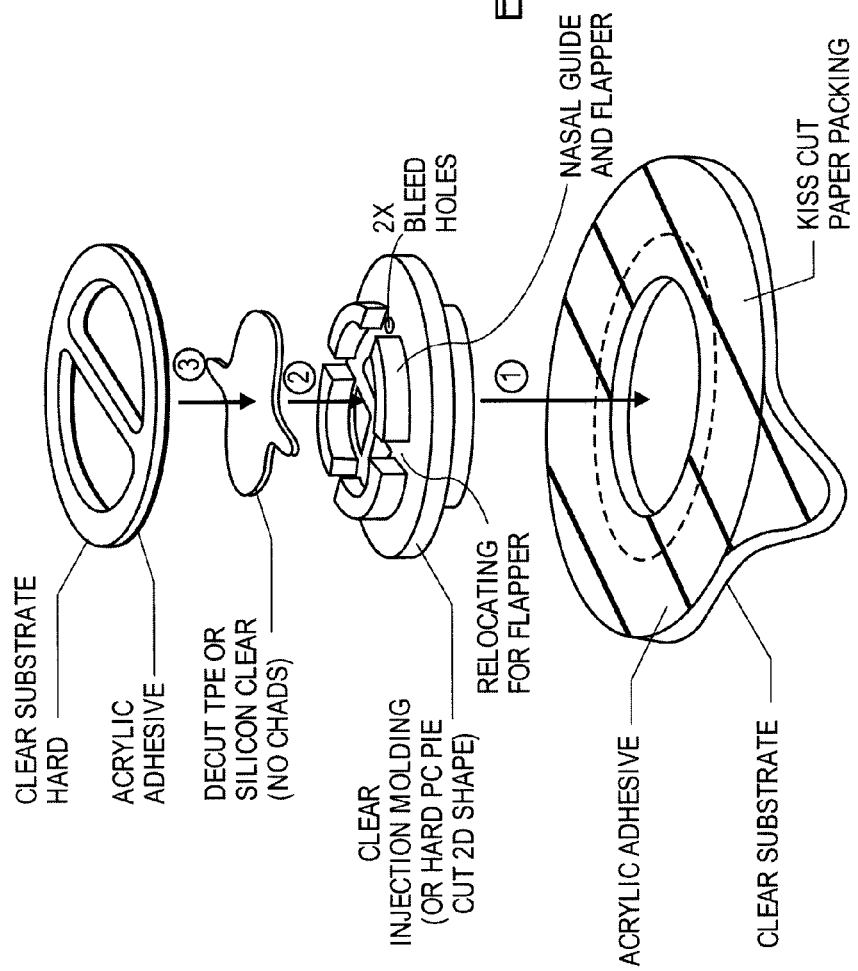

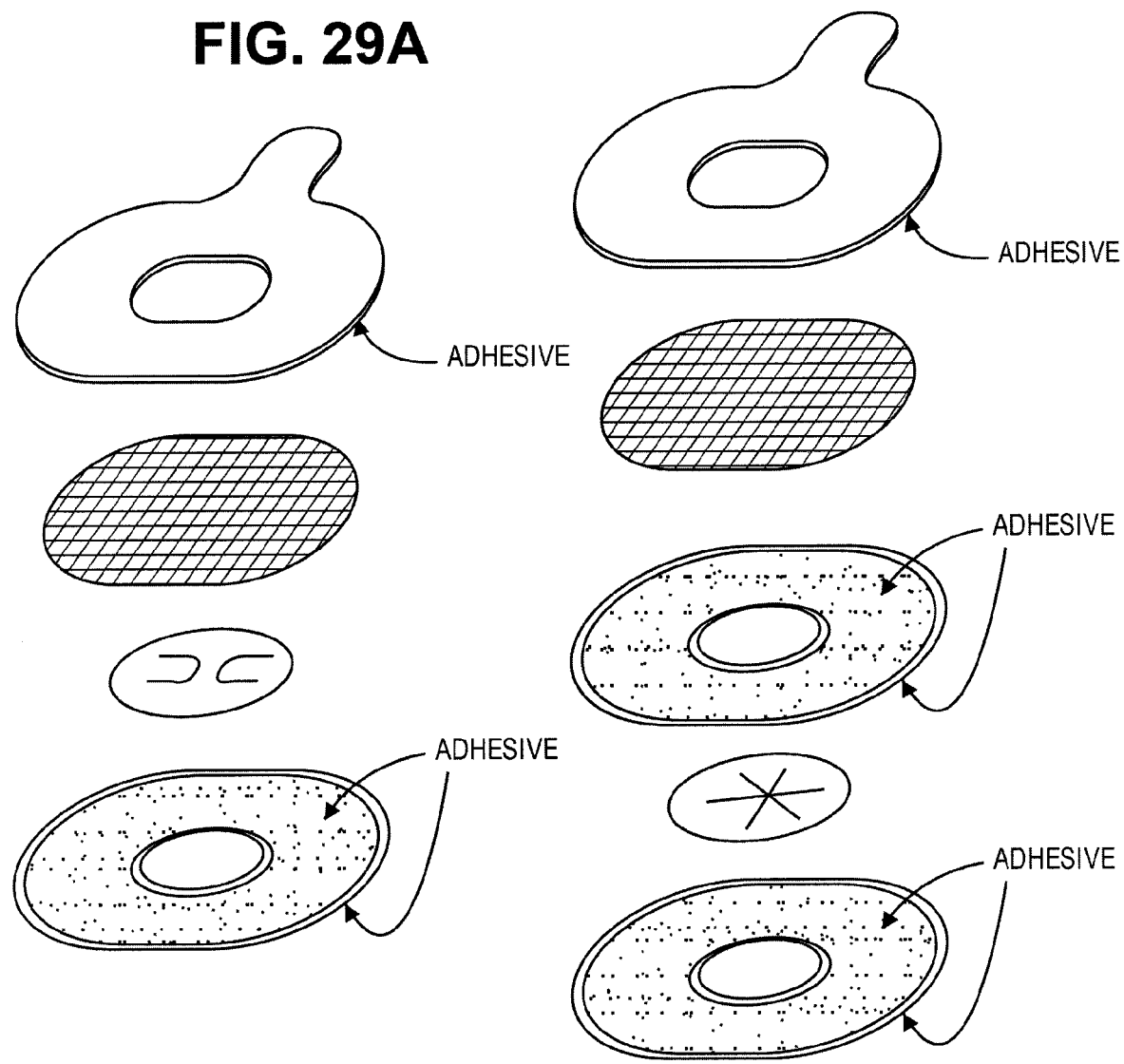

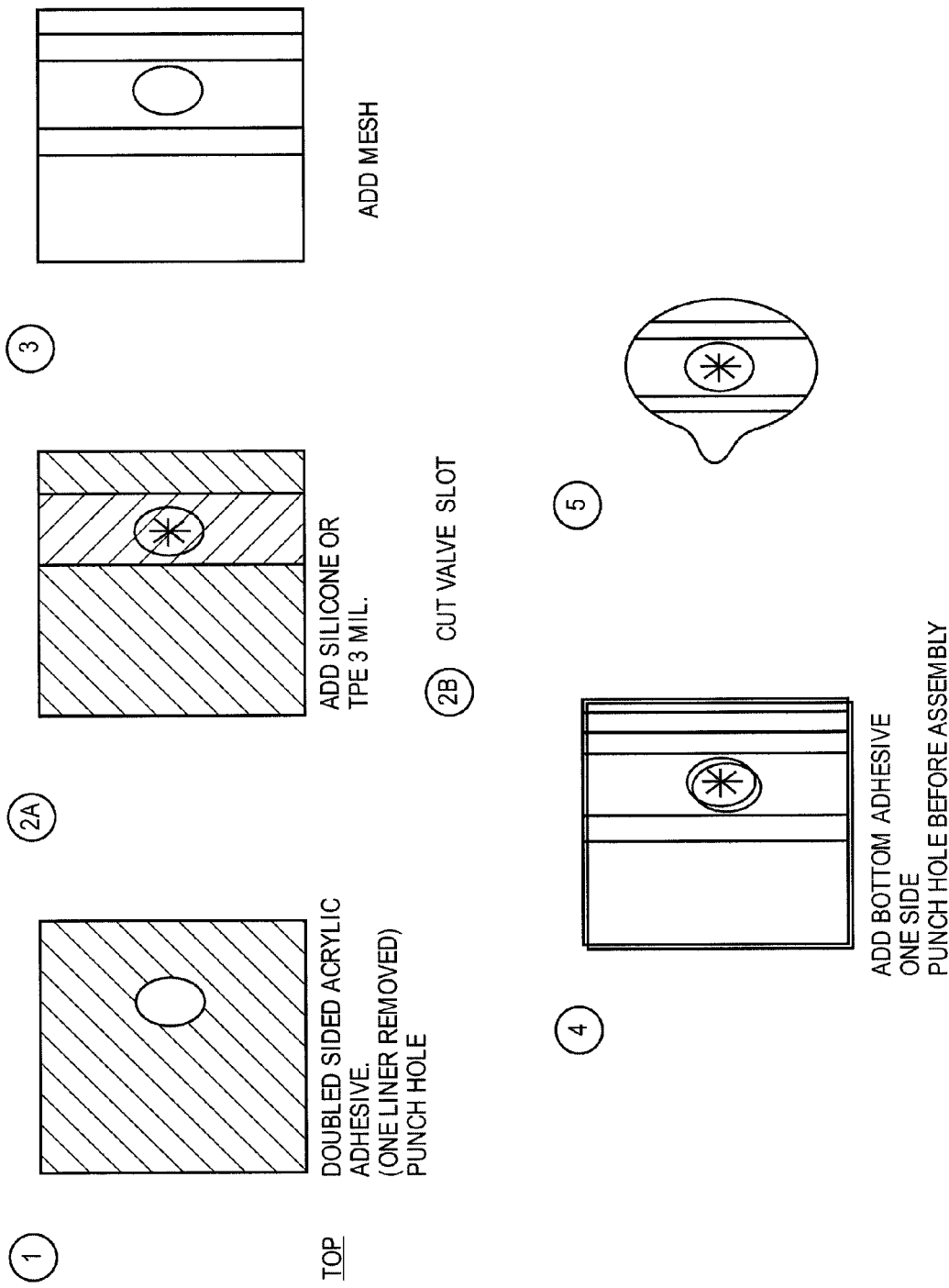

LAYERED NASAL DEVICES

CROSS-REFERENCE TO RELATED APPLICATIONS

This application claims priority to U.S. Provisional Patent Applications: Ser. No. 60/905,850 (titled "NASAL DEVICES") filed Mar. 7, 2007; Ser. No. 60/859,715 (titled "Nasal Devices") filed Nov. 16, 2006; Ser. No. 60/811,814 (titled "RESPIRATORY DEVICES") filed Jun. 7, 2006. Each of these provisional patent applications is incorporated herein by reference in its entirety.

BACKGROUND OF THE INVENTION

Nasal respiratory devices have been well-described in the following US patent applications, each of which is incorporated herein in its entirety: U.S. patent application Ser. No. 11/298,640 (titled "NASAL RESPIRATORY DEVICES") filed Dec. 8, 2005, now U.S. Pat. No. 7,735,492; U.S. patent application Ser. No. 11/298,339 (titled "RESPIRATORY DEVICES") filed Dec. 8, 2005, now U.S. Pat. No. 7,798,148; and U.S. patent application Ser. No. 11/298,362 (titled "METHODS OF TREATING RESPIRATORY DISORDERS") filed Dec. 8, 2005, now U.S. Pat. No. 7,735,491.

These patent applications generally describe nasal respiratory devices and methods for treating a variety of medical conditions through the use of such devices. These medical conditions include but are not limited to snoring, sleep apnea (obstructive, central, complex and mixed), Cheyne Stokes breathing, UARS, COPD, hypertension, asthma, GERD, heart failure, and other respiratory and sleep conditions. Such nasal respiratory devices typically induce positive end-expiratory pressure ("PEEP") or expiratory positive airway pressure ("EPAP"), and are adapted to be removably secured in communication with a nasal cavity. Similarly, the respiratory devices described herein may include any devices having one or more expiratory resistor valves. These devices may include a passageway with an opening at a proximal end and an opening at a distal end, a valve (or airflow resistor) in communication with the passageway, and a holdfast in communication with the outer walls forming the passageway. The holdfast is configured to removably secure the respiratory device within (or over or around) the nasal cavity. Examples of the valves or resistors may also be found in previously incorporated U.S. provisional patent application Ser. No. 60/811,814.

Although general descriptions of these devices have been described both functionally and by example, some specific variations of nasal respiratory devices have not previously been described. Thus, it would be beneficial to improve upon the devices, kits and methods previously described, and particularly to more fully develop certain embodiments of nasal devices and methods of arranging, using, manufacturing, inserting and removing nasal respiratory devices. Described below are specific variations of nasal devices, accessories for nasal devices, methods of using nasal devices and kits including nasal devices.

SUMMARY OF THE INVENTION

Described herein are specific variations of nasal devices, accessories for nasal devices, methods of using nasal devices and kits including nasal devices. In particular, adhesive nasal device are described. Adhesive nasal devices may be worn by a subject to modify the airflow thorough one or (more typically) both nostrils. As described in more detail below, an adhesive nasal device may be secured over the subject's nostrils so that airflow through the nostrils passes primarily (or exclusively) through the nasal device. Generally, the adhesive nasal device is removably secured over, partly over and/or at least partly within the subject's nostrils by an adhesive.

As used herein the term "adhesive nasal device" may refer to a device for covering one or both of a subject's nostrils. Thus, the description herein may apply to nasal respiratory devices adapted to fit over both of a subject's nostrils.

The adhesive nasal devices described herein may be completely flexible, or partially rigid, or completely rigid. For example, the devices described herein may include an adhesive holdfast region that is at least partially flexible, and an airflow resistor. The airflow resistor may be flexible, or rigid. In some variations, the devices described herein also include one or more alignment guides for helping a subject to orient the device when securing it over the subject's nose. For example, an alignment guide may be used to position the airflow resistor so that it is approximately centered over the subject's nostril opening.

In general, an adhesive nasal device may be secured in communication with a subject's nose, and specifically with one or both of the subject's nasal cavities. A typical adhesive nasal device may include an airflow resistor configured to resist airflow in a first direction more than airflow in a second direction and an adhesive holdfast configured to secure the airflow resistor at least partially across the subject's nose. The holdfast may comprise a biocompatible adhesive and a flexible region configured to conform to at least a portion of a subject's nose.

An airflow resistor may regulate flow of air into and out of the nostril, through the device. In some variations, the adhesive nasal device includes two airflow resistors, configured so that one airflow resistor is in fluid communication with each nostril. In addition, an adhesive nasal device includes an adhesive holdfast (e.g., holdfast region or layer) configured to secure the adhesive nasal device in communication with the subject's nasal passageway(s).

The adhesive nasal devices described herein may be composed of layers. Layered nasal devices (which may also be referred to as layered adhesive nasal devices) may be completely or partially flexible, as previously mentioned. For example, a layered nasal device may include an airflow resistor configured to resist airflow in a first direction more than airflow in a second direction (wherein the airflow resistor comprises a flap valve layer adjacent to a flap valve limiting layer), and an adhesive holdfast layer comprising an opening across which the airflow resistor is operably secured. The airflow resistor may be disposed substantially in the plane of the adhesive holdfast layer. The adhesive holdfast layer may be made of a flexible substrate that includes a biocompatible adhesive.

Any of the adhesive nasal devices described herein may include one or more leak pathways, through which air may pass even when the airflow resistor is closed. Thus, there may be a basal ("leak") flow of air (e.g., during exhalation). The leak pathway may be present on any portion or region of the nasal respiratory device. For example, the airflow resistor may include at least one leak pathway.

The flap valve (or flap valve layer) may include a plurality of valve leaflets. Thus, the flap valve may be a flexible layer of silicone or polyurethane (or any other appropriate material) that is divided up into a plurality of movable flaps, as described in more detail below. For example, the flap valve layer may include a plurality of valve leaflets that are spaced across the flap valve layer. Each valve leaflet may open and close (e.g., open during inhalation and close during expiration). In some variations, the flap valve includes a plurality of valve leaflets that open from a central point. For example, the flap valve may be formed by cutting spokes that radiate from a single point (or region) to form triangular leaflets.

An airflow resistor may include a flap valve and a flap valve limiter. A flap valve limiter may be configured as a flap valve limiting layer. This limiting layer may be adjacent to (directly adjacent or functionally adjacent) to the flap valve, and may limit the ability of the flap valve to open in one direction. The flap valve limiter (or limiting layer) may completely prevent opening of the flap valve in one direction, or it may partially prevent opening of the flap valve in one direction. For example, a flap valve limiter may be a mesh or a plurality of cross struts. Cross-struts may also be referred to as support members or cross-beams. Cross struts or cross beams may extend only partially across the passageway regulated by the airflow resistor (e.g., flap valve). For example, cross struts may be partial struts that do not completely extend across the passageway but still support one or more leaflets of the flap valve.

In some variations, the adhesive respiratory devices described herein include one or more alignment guides. An alignment guide typically helps the subject to apply the device to one (or both) nostrils in the proper orientation (e.g., so that the airflow resistor is aligned to communicate with the nasal opening). Any appropriate alignment guide may be used. For example, and alignment guide may comprise a visual alignment guide that a subject can look at to align the device (e.g., in a mirror), such as a color or shape that can be matched to one or both nasal openings. Thus, in some variations, at least a region of the device may be transparent or opaque, allowing at least a portion of the nasal opening to be seen through the device. The alignment guide may be a tactile alignment guide. A tactile alignment guide may be felt by the subject (e.g., by the subject's fingers and/or nose). For example, the alignment guide may be a ring, ridge, bump, post, or the like. In some variations, the alignment guide extends at least partially into the subject's nose when the device is worn. For example, an alignment guide may be a cone or conical region.

Also described herein are layered nasal device adapted to be adhesively secured in communication with a subject's nasal cavity that include a layered airflow resistor configured to resist airflow in a first direction more than airflow in a second direction (wherein the layered airflow resistor comprises a flap valve adjacent to a flap valve limiting layer), and an adhesive holdfast layer configured to secure the layered airflow resistor in communication with the subject's nasal cavity. These devices may include at least one leak pathway. For example, the leak pathway may be through the layered airflow resistor. In some variations, the airflow resistor layer is disposed substantially in the plane of the adhesive holdfast layer.

The adhesive holdfast layer may include a flexible substrate and a biocompatible adhesive.

In some variations, the flap valve is made of a plurality of valve leaflets. The flap valve may include a plurality of valve leaflets configured to open from a central point. In some variations, the flap valve is part of a flap valve layer. Thus, the flap valve may be include a plurality of valve leaflets formed in a flap valve layer. In some variations, the flap valve is formed in the adhesive holdfast layer. In general, a flap valve may be made of any appropriate material, including silicone or polyurethane.

Any appropriate flap valve limiting layer may be used. For example, the flap valve limiting layer may comprise a mesh. In some variations, the flap valve limiting layer comprises a plurality of struts. In some variations, the flap valve limiting layer comprises a plurality of partial struts.

Any of the devices described herein may also include an alignment guide, such as a ring, a conical alignment guide, a tactile alignment guide, or a visual alignment guide.

In some variations, the device may further include a support frame. The support frame may be removable. For example, the support frame may support the device, including the holdfast region of the device, and be completely or partially removable after the device has been applied to the subject. In some variations, the support frame remains on the nasal device after application.

Also described herein are layered nasal devices adapted to be adhesively secured in communication with a subject's nasal cavity that include a layered airflow resistor configured to resist airflow in a first direction more than airflow in a second direction (wherein the layered airflow resistor comprises a flap valve adjacent to a flap valve limiter), and a layered adhesive holdfast comprising a substrate layer, a layer of biocompatible adhesive, and a removable protective cover layer at least partially covering the biocompatible adhesive. The layered adhesive holdfast may at least partially surround the layered airflow resistor. An alignment guide may also be used as part of these devices. The flap valve may be formed from the substrate layer of the layered holdfast. In some variations, the flap valve comprises a plurality of valve leaflets configured to open from a central point.

As mentioned, any of these devices may also include a support frame. In some variations, the support frame is a support frame layer. Also described herein are methods of treating a subject that include the steps of removing a protective cover from a layered adhesive holdfast of an adhesive nasal device (wherein the adhesive nasal device comprises a layered airflow resistor), and placing the layered airflow resistor in communication with at least one of the subject's nasal cavities, and adhesively securing the adhesive nasal device to the subject's nose.

Also described herein are methods of fabricating a layered nasal device, including the steps of forming an adhesive layer comprising a biocompatible adhesive, forming a flap valve, forming a flap valve limiter, and securing the flap valve limiter to the flap valve and the adhesive layer so that the flap valve limiter is adjacent to the flap valve. The method may also include the step of securing an alignment guide in communication with the flap valve limiter, the flap valve and the adhesive layer.

In some variations, the method also includes the steps of forming an opening through the adhesive layer and securing the flap valve limiter adjacent to the flap valve in communication with the opening. Also described herein are methods of making an adhesive nasal device including the steps of forming an opening through a flexible adhesive substrate and securing an airflow resistor across the opening by securing a flap valve limiter adjacent to a flexible valve across the opening.

Layered device may also be fabricated by batch (or mass) fabrication methods. Furthermore, the layered devices described herein may be contrasted with previously described nasal (including adhesive nasal) devices that include a rim body region that forms a passageway. Although the layered devices may include a passageway, the layered devices may be substantially flat. Thus, these layered devices may not include a rim body region.

An adhesive nasal device may be adapted to be removably secured in communication with a subject's nasal cavity. The adhesive holdfast may include a biocompatible adhesive that is configured to secure the nasal device across a subject's nose or nostril(s) so that the airflow resistor is in communication with the subject's nasal opening. When placing the device in communication with the subject's nasal opening (or nasal orifice), the airflow resistor (e.g., the airflow resistor layer) may be aligned with the nasal opening (or both nasal openings). In any of the devices described herein, the adhesive holdfast region may be configured so that it does not substantially cover the subject's mouth when the device is worn by a subject. Thus, the devices may be configured so that the adhesive holdfast secures the device in communication only with one of the subject's nostrils, or with both of the subject's nostrils.

In some variations of the adhesive nasal devices described herein (particularly those variations configured to cover both of a subject's nostrils), the device may also include a bridge region in the adhesive holdfast. The bridge region may be located between the airflow resistors configured to fit over, partly over and/or at least partly within each of the subject's nostrils.

As mentioned, an adhesive holdfast may include a flexible adhesive substrate, and/or a protective cover (configured to be removed, for example, by peeling off to expose the adhesive of the adhesive layer). The device may also include a tab or handle configured to be grasped by a subject applying the device. In some variations, this tab or handle is formed of a region of the layered adhesive holdfast.

The various components of the device may be made of any appropriate materials, as described in greater detail below. For example, various components of the device (e.g., alignment guide) may be made of medical grade plastic, such as Acrylonitrile Butadiene Styrene (ABS), polypropylene, polyethylene, polycarbonate, polyurethane or polyetheretherketone. The airflow resistor may be a flap valve and the flap may be made of silicone or thermoplastic urethane. The adhesive holdfast may include an adhesive substrate made of silicone, polyurethane or polyethylene. Examples of biocompatible adhesive on the adhesive holdfast may include hydrocolloids or acrylics.

In some versions, the respiratory device further comprises an active agent. In some versions, this active agent is a drug (e.g., a medicament). In some versions, this active agent comprises an odorant, such as a fragrance. In some versions, the active agent comprises menthol, eucalyptus oil, and/or phenol. In other versions, the respiratory device may be used with other pulmonary or medical devices that can administer medication or other medical treatment, including but not limited to inhalers and nebulizers.

In some versions, the respiratory device further comprises a filter. This filter may be a movable filter, such as a filter that filters air flowing through the passageway in one direction more than another direction (e.g., the device may filter during inhalation but not expiration).

INCORPORATION BY REFERENCE

All publications and patent applications mentioned in this specification are herein incorporated by reference in their entirety, to the same extent as if each individual publication or patent application was specifically and individually indicated to be incorporated by reference in its entirety.

BRIEF DESCRIPTION OF THE DRAWINGS

FIGS. 2A-2G are different variations of flap valves.

FIGS. 3A-3H are different variations of flap valves.

FIG. 4A is a table showing different variations of flap valves.

FIGS. 5A-5C are different variations of flap valves and flap valve limiters.

FIGS. 6A and 6B, 7A and 7B, 8A-8G, and 9A-9C are different variations of flap valves and flap valve limiters.

FIG. 10F is a graph showing the flow rate of different flap valve limiters at different back pressures.

FIGS. 12A-12D, 13, 14A and 14B, and 15 are different variations of alignment guides for an adhesive nasal device.

FIG. 17 is a matrix showing different variations of adhesive nasal devices.

FIGS. 19A and 19B show a layered nasal device, and FIGS. 19C-19E show a subject wearing the device.

FIGS. 20A-20G illustrate one method of fabricating the device of FIGS. 19A and 19B.

FIGS. 21A and 21B show another layered nasal device.

FIGS. 22A-22F illustrate one method of fabricating the device of FIGS. 21A and 21B.

FIGS. 24A-24F illustrate one method of fabricating the device of FIGS. 23A and 23B.

FIGS. 27A-27C show different views of a device having an injection molded flap valve.

FIGS. 28A-28C shows a layered nasal device.

FIGS. 29A and 29B show exploded views of layered nasal devices.

FIGS. 30 and 31 illustrate methods of fabricating layered nasal devices as described herein.

DETAILED DESCRIPTION OF THE INVENTION

Figure 1B:
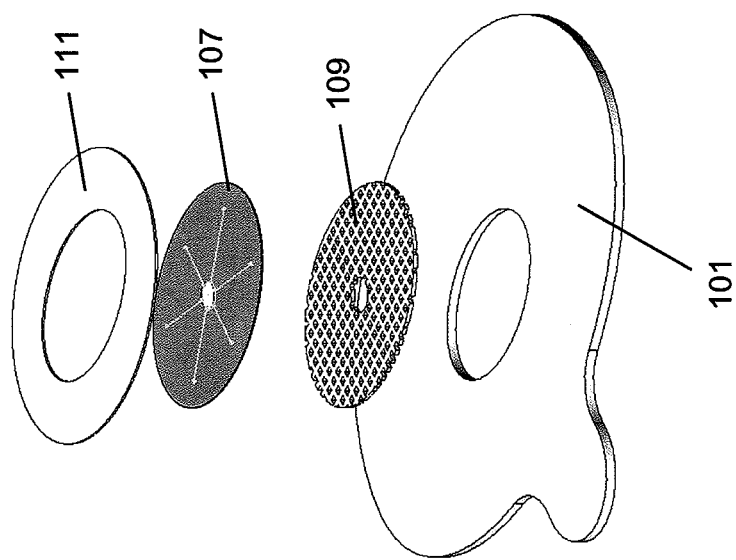
FIGS. 1A and 1B show one variation of a layered adhesive holdfast in a top view and an exploded perspective view, respectively.

An adhesive nasal respiratory device is one variation of a general nasal respiratory device in which an adhesive holdfast region is used to secure the device in fluid communication with one or both of a subject's nostrils. A nasal respiratory device, including an adhesive respiratory device, may be used to regulate a subject's respiration. For example, the device may create positive end expiratory pressure ("PEEP") or expiratory positive airway pressure ("EPAP") during respiration in a subject wearing the device. The adhesive respiratory devices and methods described herein may be useful to treat a variety of medical conditions, and may also be useful for non-therapeutic purposes. The devices and methods described herein are not limited to the particular embodiments described. Variations of the particular embodiments described may be made and still fall within the scope of the disclosure. Examples and particular embodiments described are not intended to be limiting.

As used herein, an adhesive nasal device may be configured to fit across partly across, at least partly within, in, over and/or around a single nostril (e.g., a "single-nostril nasal device"), or across, in, over and/or around both nostrils ("whole-nose nasal device"). Both single-nostril nasal devices and whole-nose nasal devices may be referred to herein as "adhesive nasal devices," and (unless the context indicates otherwise), any of the features described for single-nostril nasal devices may be used with whole-nose nasal devices, and vice-versa. In some variations, an adhesive nasal device is formed from two single-nostril nasal devices that are connected to form a unitary adhesive nasal device that can be applied to the subject's nose. Single-nostril nasal devices may be connected by a bridge (or bridge region, which may also be referred to as a connector). The bridge may be movable (e.g., flexible), so that the adhesive nasal device may be adjusted to fit a variety of physiognomies. The bridge may be integral to the nasal devices. In some variations, single-nostril nasal devices are used that are not connected by a bridge, but each include an adhesive region, so that (when worn by a user) the adhesive holdfast regions may overlap on the subject's nose.

Layered nasal devices are of particular interest, and are described more fully below. Layered adhesive nasal devices may include two or more layers. For example, a layered nasal device may include an adhesive holdfast layer and an airflow resistor layer. These layers may be composed of separate layers, and these layers may be separated by other layers, or they may be adjacent. The adhesive holdfast layer may be itself formed of layers (optionally: a substrate layer, a protective covering layer, an adhesive layer, etc), and thus may be referred to as a layered adhesive holdfast. Similarly, the airflow resistor may be formed of multiple layers (optionally: a flap valve layer, a valve limiter layer, etc.), and thus may be referred to as a layered airflow resistor. In some variations, the layered adhesive holdfast and the layered airflow resistor share one or more layers. For example, the flap valves layer and the adhesive substrate layer may be the same layer, in which the leaflets of the flap valve layer are cut from the substrate layer material. As used herein, a "layer" may be generally planar geometry (e.g., flat), although it may have a thickness, which may be uniform or non-uniform in section.

As used in this specification, the singular forms "a," "an," and "the" include plural reference unless the context clearly dictates otherwise. The following descriptions including various design parameters or goals, and methods and devices which fit the design parameters or goals. The devices and methods described herein (and recited by any claims) are not limited to any particular theory of operation.

In general, the adhesive nasal devices described herein include a holdfast region (or layer) and at least one airflow resistor. As will be apparent from the figures, many of these devices may be removable and insertable by user without special tools. In some variations, a subject may use an applicator to apply the device (e.g., to help align it).

In operation, an adhesive nasal device is placed in communication with one or both of a subject's nostrils to modify the flow of air through the subject's nose. Thus, the respiratory devices described herein include one or more airflow resistors for modifying the flow of air through the nose in at least one direction. In most variations of the devices described herein, the airflow resistor is configured to occlude airflow through a passageway in one direction more than it occludes airflow in the opposite direction. For example, an airflow resistor may occlude airflow during exhalation more than inhalation. Resistance to inhalation may be increased minimally, negligibly, or not at all. Examples of airflow resistors are described below, but any appropriate airflow resistor may be used. For example, airflow resistors may be valves for regulating airflow (e.g., flap valves, hinge-less valves, balloon valves, stepper valves, ball valves, etc.) or the like. In the examples shown in the figures and described herein, the airflow resistor is typically a flap valve having one or more flaps or leaves that move to regulate flow through the resistor. The airflow resistor may also include a valve limiter, such as a flap valve limiter. For example, a valve limiter restricts the ability of a valve to open in one or more directions. As described in more detail below, the flap valve limiter may prevent the valve from substantially opening in one direction (e.g., expiration) or may allow some degree of opening or partial opening, but not complete opening Any of the nasal devices described herein may also include one or more leak pathways through which air can pass when the valve is otherwise closed. The leak pathway may be separate from the airflow resistor, or it may be part of the airflow resistor (e.g., passing through a region of the flap valve, etc.). In some variations, the airflow resistor is configured so that a leak pathway is formed when the valve is closed. For example, the flap(s) of the flap valve may not seal when the valve is closed. A leak pathway may pass through any appropriate region of the device, including the holdfast region.

An adhesive nasal device may be configured to treat snoring, or any other sleep disordered breathing, as described briefly above. For example, a subject may apply an adhesive respiratory device over his nose (one or both nostrils) by exposing an adhesive on the holdfast of the device (e.g., by removing a protective cover material from an adhesive region of the holdfast) and applying gentle pressure to adhere the device around the nostrils. In this way, the device may be seated around the nasal orifice (and may project at least partly into the nostrils) and form at least a partial seal between the nostrils and the device so that the majority of flow into and out of the nostrils passes through the passageways of the nasal device. Once the device is applied to the subject's nose, respiration through the nostrils may be regulated. In some variations, the adhesive nasal device is configured so that there is only nominal resistance through the nasal device during inhalation (e.g., less than about 2 cm $H_2O$, less than about 1 cm $H_2O$ less than about 0.5 cm $H_2O$, less than about 0.4 cm $H_2O$, less than about 0.3 cm $H_2O$, less than about 0.2 cm $H_2O$, etc.), but increased resistance to airflow during exhalation (e.g., greater than about 2 cm $H_2O$, greater than about 3 cm $H_2O$, greater than about 4 cm $H_2O$, greater than about 5 cm $H_2O$, greater than about 6 cm $H_2O$, greater than about 7 cm $H_2O$, greater than about 8 cm $H_2O$, greater than about 9 cm $H_2O$, greater than about 10 cm $H_2O$, greater than about 12 cm $H_2O$, etc.). During inhalation in a subject wearing such a device, the subject may breathe through the nose (and thus through the nasal device). During exhalation, the adhesive nasal device provides greater resistance to airflow through the device. Resistance to exhalation may be limited (or set) by a leak pathway. Thus, the subject may still breathe predominantly though the nose (and the nasal device) during exhalation, but may also breathe at least partly through the mouth.

It may also be beneficial for a subject to wear a nasal respiratory device over an extended period of time (e.g., during a period of sleep). Described below are variations of adhesive nasal devices (including layered nasal devices) that may be comfortably worn and secured in or over the subject's nose or nasal passages. In some variations, a grip (e.g., a tab, handle, strap, or other additional interface region) may be included to help secure the device to the subject's nostril, nose or face, and may additionally or alternatively be helpful in positioning or manipulating (e.g., gripping) the device, particularly when it is being applied. This additional interface region may be formed of the same material as the adhesive holdfast region, or it may be a separate region, as described in more detail below.

In some embodiments, one or more components of the device are impregnated with, contain or are coated with one or more compounds that may be inhaled during use. The presence of airflow, heat or other conditions may facilitate the release of the compound into the inhaled air or surrounding tissues. The compound may be herbal (such as menthol or lavender), chemical or pharmaceutical (such as an antihistamine or anti asthma drug) in nature. Depending on the compound, the user might experience a pleasant aroma (which may soothe or promote sleep or activity) or medical benefits, such as nasal decongestion or asthma relief. The compound may be inhaled during all or at least a portion of the time the user is wearing the device. The compounds may be used as part of treatment of a sleep apnea, snoring, or may find use in other embodiments for other medical conditions.

In still other embodiments, the device may include a filter that removes particulate matter from external air upon inhalation. Particulate matter that would be removed may include dust and allergens. This invention may be embodied within a sleep apnea device, snoring device, a respiratory device, or comprise a stand alone device.

Other materials of interest include any materials that can serve as filters for allergens, pollen, dander, smog, etc. By providing a filter within the device, sinusitis, sleep apnea, snoring, hay fever, allergic rhinitis, and other allergic respiratory conditions may be reduced or prevented. This filter may in fact be part of the airflow resistor (e.g., the valve limiter) or may be a separate component of the device. Any suitable filtering material known to those skilled in the art may be used with the respiratory devices described herein. Such materials include, but are not limited to, activated carbon charcoal filters, hollow-fiber filters, and the like.

In some versions, the respiratory device may comprise a filter that remains in the path of inhalation and/or exhalation during use. In some versions, the filter material remains in the path of both inspiratory and expiratory airflow. This filter material may not appreciably alter resistance to airflow in either direction, or it may alter airflow to substantially the same degree in both directions (inhalation and exhalation). In some versions, the filter comprises a material having a large pore size so that airflow is not significantly inhibited.

In some versions, the device is used with an active agent. In some versions, the active agent comprises a drug. An active agent (e.g., a medicament) or other compound can be placed in or on the device to deliver the active agent into the mouth, tongue, hard and soft palates, sinuses, nose, nasal cavity, pharynx, vocal cords, larynx, airways, lungs, trachea, bronchi, bronchioles, alveoli, air sacs, or any tissues that are exposed to inspiratory or expiratory airflow. In some cases, the active agent may be embedded or impregnated in the device or components of the device. In some cases the active agent is a coating. An active agent may comprise any compound that is in some way useful or desirable for the patient. For example, the active agent may be any odorant, including: menthol, phenol, eucalyptus, or any agent that provides a fragrance in the inspired air. Alternatively, an active agent may comprise a drug with beneficial effects, such as beneficial vasculature effects. For example, an active agent may comprise a drug that effects the blood vessels (oxymetazoline or any other vasoactive compound), nasopharynx, airways or lungs (albuterol, steroids, or other bronchoconstriction or bronchodilation compounds). An active agent may comprise, for example, an antibiotic or a steroid. The above list of active agents is not meant to be limiting.

An active agent may be placed in or on any portion of the device. Furthermore, the location of the active agent within the respiratory device may specifically guide the delivery of the active agent. For example, in versions of the respiratory device configured to be placed inside a respiratory cavity, when the holdfast comprises an active agent (e.g., coated, embedded or otherwise part of the holdfast), the drug may be delivered through the mucus membranes of the respiratory cavity. In another example, an active agent may be included as a powder or releasable coating that may be aerosolized and delivered within the respiratory system. Thus, an active agent may be on a surface of the device (e.g., the passageway, holdfast or airflow resistor) or embedded within any surface of the device. A separate drug-containing region may also be included in the device. The addition of an active agent may be of particular interest in treating allergies and sinusitis. Respiratory devices (with or without airflow resistors) may therefore comprise active agents such as menthol or other fragrant compounds.

In some variations of the device an aligner is used to help align the device (e.g., the airflow resistor) with one or both of a subject's nostrils. An aligner may include a tactile aligner that may be felt by the subject's nose or hands, a visual aligner (e.g., a color, pattern, or other marking) that may be seen by the subject, or a structural aligner that inserts at least partly in or around the subject's nostril(s), or any combination of these. Aligners are described more fully below. In some variations, an aligner may also help maintain the alignment of the device with the subject's nostril(s), for example, by helping maintain the patency of the nostril opening.

Figure 1A:
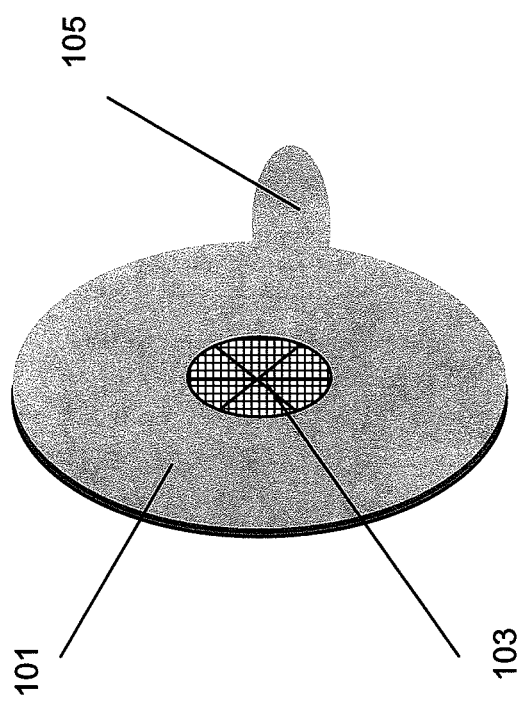

FIG. 1A is a top view of one example of a layered nasal device as described herein. The layered nasal device shown in FIG. 1 includes a holdfast layer 101 and an airflow resistor 103. The reverse side of the device shown in FIG. 1 includes an adhesive material (not shown) that may be covered by a protective covering. The protective covering (which may also be referred to as a protective liner) can be removed to expose the adhesive before application of the device. Thus, the holdfast layer of the device secures it to the subject. This holdfast layer may itself be layered, and may include an adhesive substrate (e.g., a backing layer). For example, the adhesive substrate may be a foam backing. This backing may act as a substrate for an adhesive material. In some variations, the adhesive substrate is itself adhesive. The holdfast layer 101 may have different regions, including a peri-nasal regions surrounding an opening (though which air may flow), and a tab 105 or grip region forming a tab that may make the device easier to grasp, apply and remove. Other regions may include regions of more aggressive and less aggressive adhesive (e.g., more or less adhesive material), regions of hydrogel material (including adhesive hydrogels) to help prevent irritation from repeated or extended use. Although the tab is shown as part of (integral with) the holdfast material, this region may also be formed separately, and may be made of different materials.

FIG. 1B shows an exploded view of the device of FIG. 1A. This exploded perspective view illustrates the layers of the device, including the adhesive holdfast 101 (which may itself be layered), two layers of airflow resistor, including the flap valve 107 and flap valve limiter 109, and an adhesive ring 111 that may help attach the flap valve and flap valve limiter to the adhesive holdfast. The holdfast, airflow resistor, alignment guide, and other device accessories are described in greater detail in the sections below.

Airflow Resistors

An airflow resistor is typically placed in communication with one or both of the subject's nostrils, so that at least some of the air flowing into and out of the nostrils passes through the airflow resistor. In general, an adhesive nasal device is sealed at least partly over, at least partly within, or at least partly in or around the subject's nostril(s), and the airflow resistor may control the amount of resistance, the degree of airflow, or the pressure differential across the nasal device. Any appropriate airflow resistor may be used as part of the adhesive nasal devices described herein. The airflow resistors described herein typically restrict airflow in one direction more than they restrict airflow in the opposite direction. For example, an airflow resistor may occlude airflow during exhalation more than inhalation. Examples of airflow resistors may be found in published U.S. patent application Ser. No. 11/298,640, titled "NASAL RESPIRATORY DEVICES" (filed Dec. 8, 2005), herein incorporated by reference in its entirety.

In some embodiments, the pressures created by the airflow resistor during exhalation may be between 0.01 and 100 cm of $H_2O$ measured at a flow rate of 100 ml/sec. In some variations of the adhesive devices described herein adapted to be used for snoring, the airflow resistor creates a resistance to exhalation that relatively low (compared to 100 cm of $H_2O$). For example, the resistance to exhalation may be between about 0.5 cm of $H_2O$ and about 10 cm $H_2O$, or between about 2 cm $H_2O$ and about 8 cm $H_2O$, or between about 3 cm $H_2O$ and about 8 cm $H_2O$, or about 4 cm $H_2O$. The resistance in terms of cm of $H_2O$ may be measured at a flow rate of 100 ml/sec.

Valve-type airflow resistors are particularly suitable. In particular, valves that may be used include flap valves (having one or more flaps or leaflets), hingeless valves, stopper-type valves, membrane-type valves, ball valves, balloon-type valves, and the like. This list is not intended to be exhaustive, and other types of selective airflow resistors may be used. Moreover, multiple airflow resistors may also be used, which may include combinations of different types of airflow resistors. Flap valves are of particular interest. An airflow resistor configured as a flap valve typically includes one or more hinged or flexible flaps (or leaves) that is movably secured so that the flap may open when air flows in one direction, and close when air flows in the opposite direction, or when air is not flowing. The opening and closing of the flap may allow air to flow across the valve, and thereby regulate airflow within a passageway in which the flap valve is positioned. In operation, the flap portion of the flap valve can thus selectively occlude airflow in one direction more than in other directions.

Valves configured for PEEP (positive end expiratory pressure) may also be used with any of the devices described herein. For example, a valve may be configured to have a non-zero threshold pressure for opening during expiration so that the valve is closed during expiration when the pressure across the valve is below the threshold pressure for opening during expiration, but the valve opens during expiration when the valve exceeds the threshold pressure for opening during expiration.

In some variations, an airflow resistor for use in an adhesive respiratory device includes a flap valve and a flap valve limiter that limits the movement of the flap valve. For example, a flap valve may be a flexible material (e.g., silicone) that can bend or flex to create an opening for airflow during inspiration (in a first direction). The flap valve may be prevented from opening for airflow during exhalation (in a second direction) by a flap valve limiter. Thus, a flap valve limiter may be a structure having a flap valve engagement surface (such as a bar, post, mesh, etc.) that limits the flap valve from opening in the second direction. In some variations, the flap valve limiter is a tether or hinge that is connected to the flap and prevents it from substantially extending beyond a predetermined position. Other flap valve limiters may be configured as valve supports (e.g., cross-bars) that prevent the valve from collapsing when air flows in one direction through the passageway. The airflow limiter may also include a valve seal region (e.g., a rim or ridge) against which the flap may be seated or abut when the valve is "closed."

As mentioned above, one or more leak pathways may be included as part of the adhesive respiratory device. A leak pathway typically allows air to flow through the passageway even when the valve is closed. Thus a minimum basal level of airflow may be permitted through the passageway regardless of the state of the airflow resistor. In some variations, the leak pathway is a hole or unoccluded passage. A leak pathway may be a part of any region of the nasal respiratory device. For example a leak pathway may be part of the airflow resistor, part of the holdfast (or some combination thereof). In some embodiments, the leak pathway arises from an intentional lack of perfect sealing or abutment of various components of the device (e.g., between leaflets of a flap valve, etc). A nasal respiratory device may be configured to have multiple leak pathways.

The flap of a flap valve may be made of a flexible material, or a hinged stiff material. In some variations, the flap comprises a thin sheet of flexible material that is shaped to fit across an opening and at least partially occlude airflow through the opening when the flap is closed. The flap may be shaped so that it does not occlude airflow through one or more leak pathways.

FIG. 2A through FIG. 4 show different variations of flap valves. In some variations, the flap valve (or valves) is formed from multiple slots or openings in the valve material. Thus, a flap valve may be formed from a layer of material that is cut to form different flaps or leaves. A flap valve may be any appropriate shape. For example, FIG. 2A shows a flap valve having four valve leaflets (creating two valve openings) that is formed by cutting the valve layer using two H-shaped patterns. Similarly, FIG. 2B shows a flap valve having multiple independent leaflets that are formed by cutting the valve into seven individual flaps. Each of the leaflets has a neck region that may bend to open the flap. A flap valve may be formed from an irregularly shaped cut (e.g., as shown in FIG. 2C, which has a square-wave shape). FIGS. 2D-2G illustrate a flap valve that is formed of parallel layers. A side perspective view is shown in FIG. 2D in which the flap leaflets are partially opened. FIG. 2E shows a top view of this flap valve. FIGS. 2F and 2G show airflow patterns through this variation of a flap valve. In FIG. 2F, air may flow through the open valve, as shown. Pressure from the airflow may open the valve leaflets and keep it open. In FIG. 2G, the valve leaflets shown in FIG. 2F are closed, and little or no air may flow past them. In this example, the valve leaflets overlap with adjacent valve leaflets in the valve layer, so that a seal may be formed when the valve is closed. Thus, in FIG. 2G, the air flowing downwards may keep the valve closed.

Figure 3A:
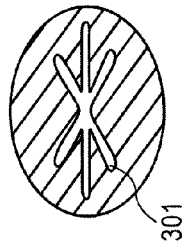
Figure 3B:
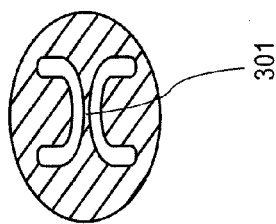
Figure 3C:
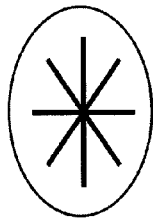
Figure 3D:
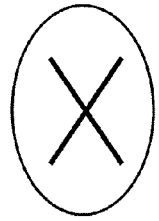
Figure 3F:
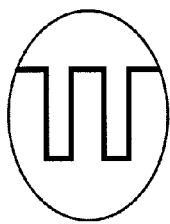
Figure 3G:
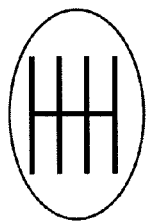
Figure 3H:
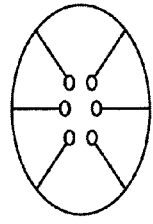

In FIGS. 3A and 3B, there is a space between the flap leaflets and the rest of the layer forming the flap valve 301. Thus, even when the flap leaflets are closed, the space between the flaps leaflets may form a leak pathway, permitting the passage of airflow through the device. In some variations the flap valves open from a single point, as shown in FIGS. 3C and 3D. In these examples, the flap leaflets of the flap valve are formed by cutting in a radial pattern from a single point, resulting in pie-shaped leaflets. The valve may be opened by bending back the pie-shaped wedges to form a single central opening. This variation may be useful, because valve leaflets that open from a central point may be more reliably opened without interfering with the walls of the nose or nasal opening. Similarly the flap valve shown in FIG. 3E has leaflets that open outwards, but from multiple points. The flap valves shown in FIGS. 3F and 3G open along a long axis of the flap valve layer, and the edges of the flap valve shown in FIG. 3H open towards a central point.

The shape of the flap valves may help determine the resistance (to both expiration and inspiration) for the airflow resistor. For example, the table in FIG. 4 illustrates exemplary inspiratory and expiratory resistance (in cm $H_2O$) of airflow resistors having a flap valve as shown in the column to the left. In this example, the airflow resistor includes both the flap valve and an adjacent flap valve limiter that permits the flap valve to open in only one direction (e.g., upwards out of the page in this example, representing inspiration). Other factors, including the geometer of the airflow resistor, the size and location of the leak pathways, and the material from which the flap valves are made may also affect the inspiratory and expiratory resistance.

Thus, a flap valve (especially the flap region) may comprise any appropriate material, including those previously mentioned. For example, the flap may comprise polymeric materials, rubber (natural and synthetic), paper, fabric, or the like. For example, materials which may be used include: latex, polyethylene, polypropylene, polystyrene, polyvinyl chloride, polyvinylidene chloride, polyvinyl acetate, polyacrylate, styrene-butadiene copolymer, chlorinated polyethylene, polyvinylidene fluoride, ethylene-vinyl acetate copolymer, ethylene-vinyl acetate-vinyl chloride-acrylate copolymer, ethylene-vinyl acetate-acrylate copolymer, ethylene-vinyl acetate-vinyl chloride copolymer, nylon, acrylonitrile-butadiene copolymer, polyacrylonitrile, polyvinyl chloride, polychloroprene, polybutadiene, thermoplastic polyimide, polyacetal, polyphenylene sulfide, polycarbonate, thermoplastic polyurethane, thermoplastic resins, thermosetting resins, natural rubbers, synthetic rubbers (such as a chloroprene rubber, styrene butadiene rubber, nitrile-butadiene rubber, and ethylene-propylene-diene terpolymer copolymer, silicone rubbers, fluoride rubbers, and acrylic rubbers), elastomers (such as a soft urethane, water-blown polyurethane), and thermosetting resins (such as a hard urethane, phenolic resins, and a melamine resins), and injection moldable materials such as polyether block amide (e.g., PEBAX®), and the like.

An airflow resistor, including a flap valve, may be formed as a layered airflow resistor. Further, a flap valve layer may be formed in any appropriate manner. For example, a flap valve may be fashioned by cutting, molding, or otherwise forming a flap valve leaflet (or a plurality of flap valve leaflets) from a layer of material. In one variation, a layer of material (e.g., silicone, polyurethane, etc.) is die cut to form the flap valve leaflets as part of a flap valve layer. Other methods of cutting may be used to form the valve or each valve leaflets, including laser cutting, jet cutting, or the like. In some variations, the flap valve is formed by molding. For example, the flap valve may be formed by thermoforming, injection molding, or the like. In some variations, the flap is made out of silicone or thermoplastic urethane. For example, the flap may be a thin and flexible piece of silicone. This flap may be any appropriate thickness that allow it to be flexible (e.g., to move from the open and closed positions). For example, the flap may comprise silicone that is between 0.0001 and 0.1 inches thick. In some embodiments, the silicone is approximately 0.002 inches thick.

In variations in which the flap valve is made of a flexible material it may be particularly advantageous to include a flap valve limiter as part of the airflow resistor to regulate the motion of the flap valve. As described above, a flap valve limiter is typically an air-permeable structure that limits the range of motion of the flap valve, preventing it from opening (or limiting it to partially opening) in at least one direction. For example, the flap valve limiter may be a mesh, grid, bar, peg, or other structure that does not substantially inhibit the passage of air, but can limit the movement of the flap valve leaflet(s) in at least one direction. FIG. 5A shows two examples of flap valve limiters 501 that can be used with the flap valves 503 shown above them. In this example, the flap valve limiters 501 shown are die-cut plastic pieces having a flap valve seating surface (the surface shown) onto which the leaflets of the flap valve may rest. FIGS. 5B and 5C show similar variations of the flap valve and flap valve limiter assembly (forming an airflow resistor) incorporated in an opening through a holdfast layer.

Figure 7B:
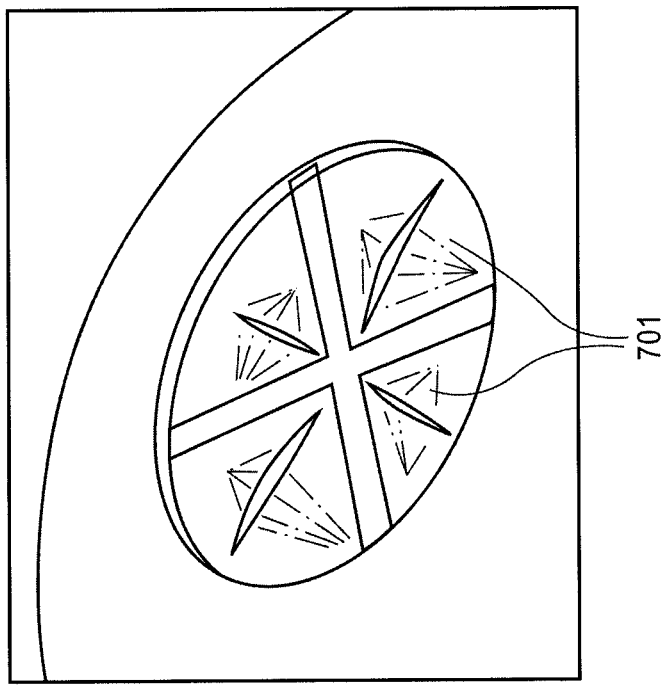
Figure 7A:
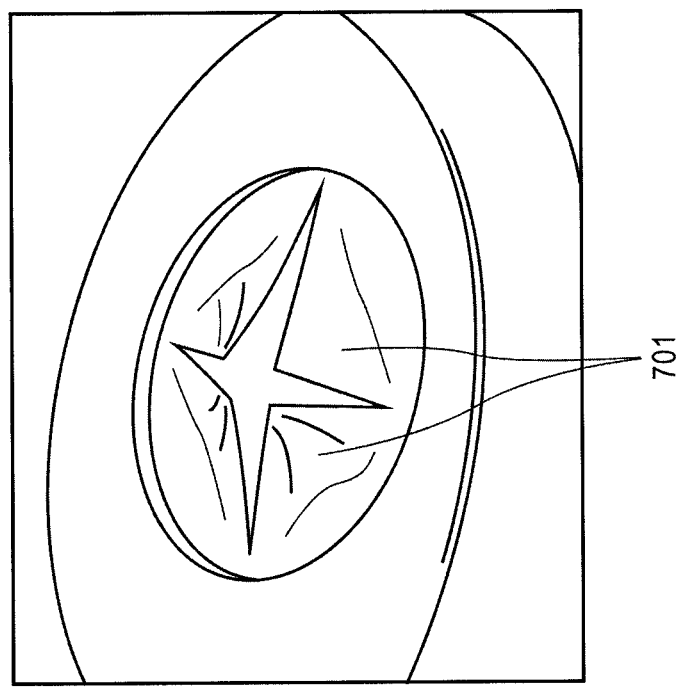
Figure 8A:
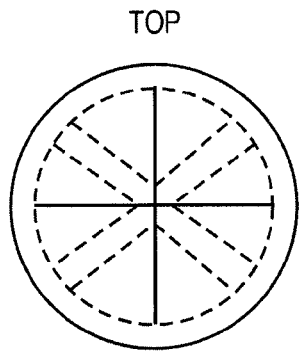
Figure 8B:
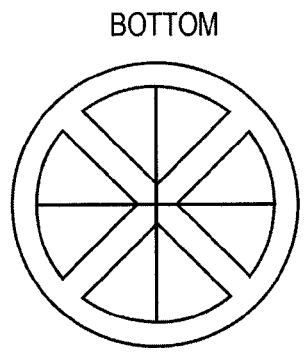
Figure 8C:
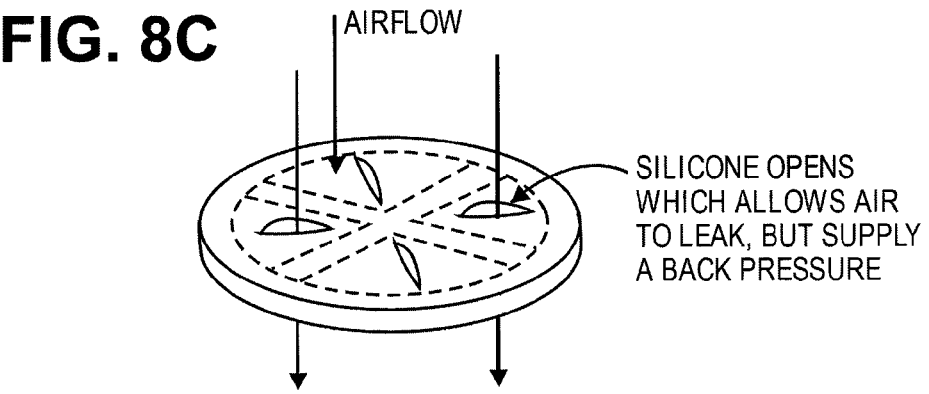
Figure 8D:
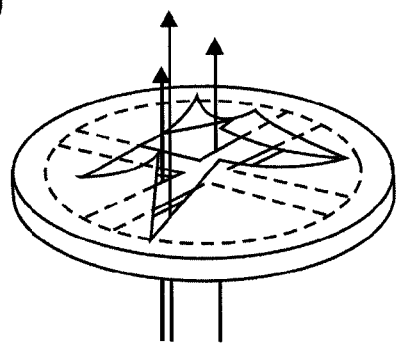
Figure 8E:
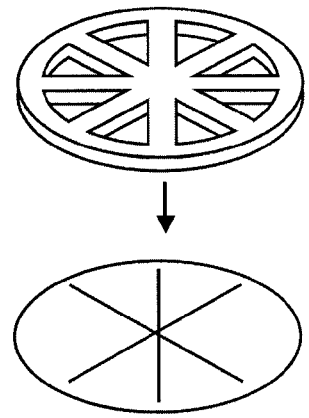
Figure 8F:
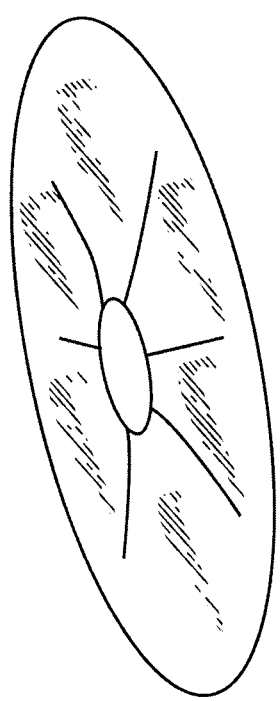
Figure 8G:
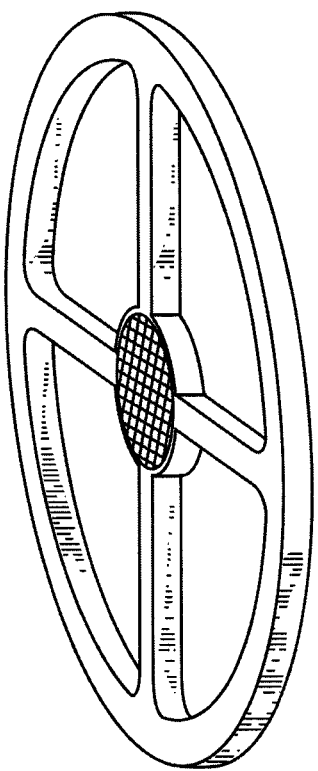

A flap valve limiter may be formed in any appropriate manner, including molding (e.g., injection molding), cutting (e.g., die cutting, stamping, laser cutting, etc.) or thermosetting. In some variations the flap valve limiter is a flap valve layer that is formed from a mesh. Thus, the flap valve limiter may be formed by cutting, molding, etc. For example, a flap valve limiter may be formed by cutting a mesh material. Other examples of airflow resistors having a flap valve and a flap valve limiter are shown in FIGS. 6A and 6B during both inhalation (FIG. 6A) and exhalation (FIG. 6B). In FIG. 6A, the flap valves have opened to allow air to flow through them, while in FIG. 6B (exhalation) the flap leaflets are closed, resting against the flap valve limiter. Airflow through the airflow resistor is thus limited to the central leak pathway 601 during exhalation. The central leak pathway 501 is a hole through the flap valve and limiter. FIGS. 7A and 7B show another airflow resistor having a leak pathway formed by the space between the valve leaflets 701, as described briefly above. FIG. 7A shows an airflow resistor having a flap valve and a flap valve resistor that is opened (e.g., during inhalation). FIG. 7B shows the opposite side of the same airflow resistor during expiration. Although the valve leaflets are closed in FIG. 7B, the air pressure from expiration (pushing the leaflets against the struts of the flap valve limiter) creates leak pathways 701. FIG. 8A-8D also illustrates this. In these examples, the flap valve limiter limits the movement of the flap valve by supporting the valve leaflets at their center. In other variations, the valve leaflets may be supported along their entire surface (e.g., when the flap valve limiter is a mesh), or at their edges.

Figure 9C:
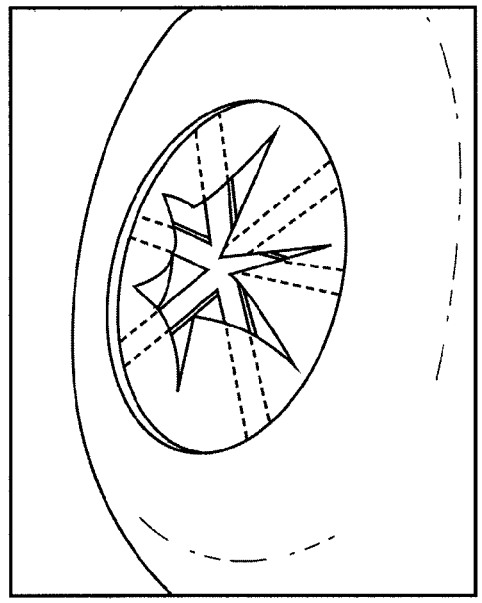
Figure 9A:
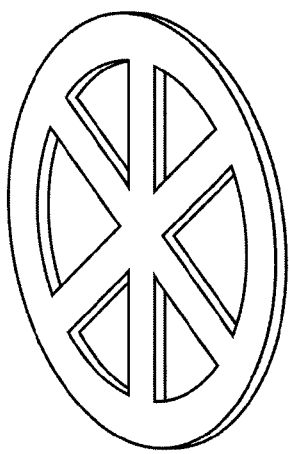
Figure 9B:
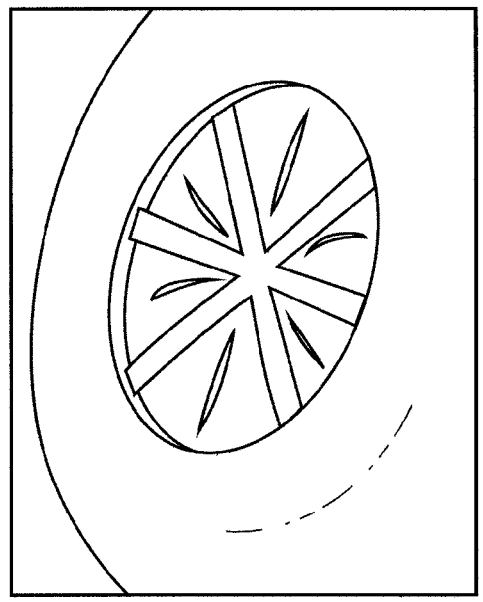

Although the flap valve and flap valve limiter shown in FIGS. 7A-8D are configured to have four valve leaflets, any appropriate number of flaps or leaflets may be used, as mentioned above. FIGS. 8E and 8F show examples of an airflow resistor having six pie-cut valve leaflets and a flap valve limiter that may be used with it. FIG. 8G shows another variation of a flap valve limiter that includes both mesh and strut regions. Another flap valve limiter that may be used with a six-leaf flap valve is shown in FIG. 9A, and FIGS. 9B and 9C show a six-leaf flap valve in operation.

Figure 10A:
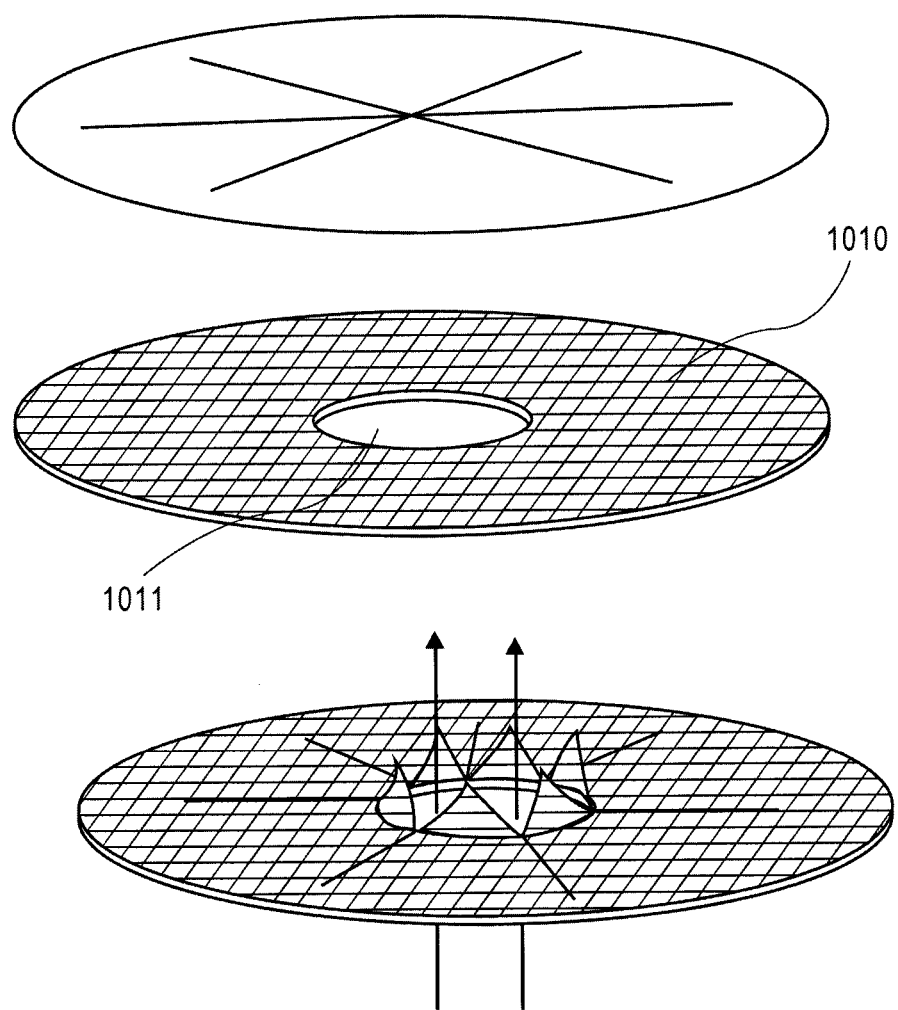
FIG. 10A-10E are different variations of flap valve limiters.

FIG. 10A shows a mesh flap valve limiter 1010. In this example, the flap valve limiter 1010 includes a hole 1011 through the center region. This central hole may form a leak pathway, as shown. Any appropriate mesh may be used. For example, the mesh may be formed of nylon or other fibrous materials. As briefly mentioned above, the valve limiter may be made of any appropriate air permeable material or shape. In some variations it may be beneficial to include materials that are flexible (e.g., nylon mesh). In some variations, it may be beneficial to use materials that are relatively stiff. Exemplary meshes may include: molded polypropylene plastic mesh (e.g., 0.0140" thickness), precision woven nylon mesh (31.2 openings per inch×31.2 openings per inch), precision woven nylon mesh (80×80), precision woven polypropylene mesh (69×69), filter mesh, precision woven nylon mesh (198×198), PTFE diamond mesh, precision woven polyester mesh (109×109), precision woven polyester mesh (45.7×45.7).

In some variations, the flap valves or the flap valve limiter (or both) is coated with a material to increase or decrease friction between the two layers (e.g., to prevent the flap leaflets from sticking to each other and/or to the flap valve limiter). In some variations of the airflow resistor, the flap layer (forming the flap valves) is positioned immediately adjacent to a layer forming the flap valve limiter, as shown in FIG. 5A-9C, above. However, the flap valve layer and the airflow resistor layers may not be immediately adjacent. For example, there may be an intermediate layer.

Figure 10D:
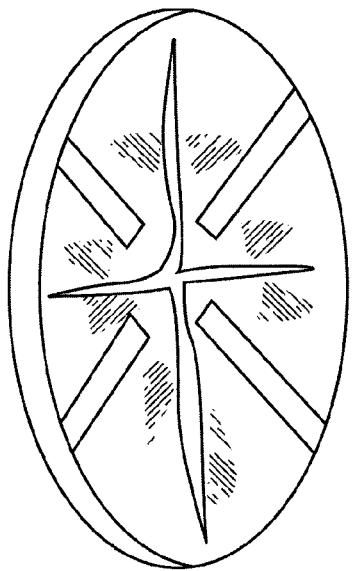
Figure 10E:
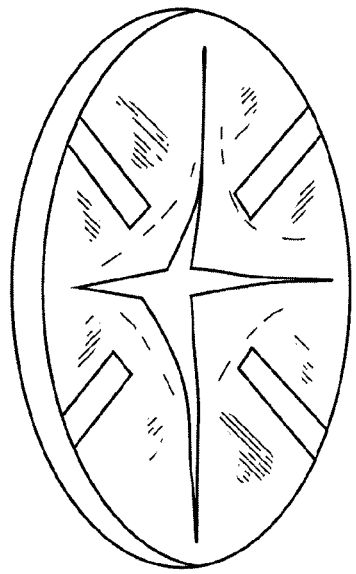
Figure 10B:
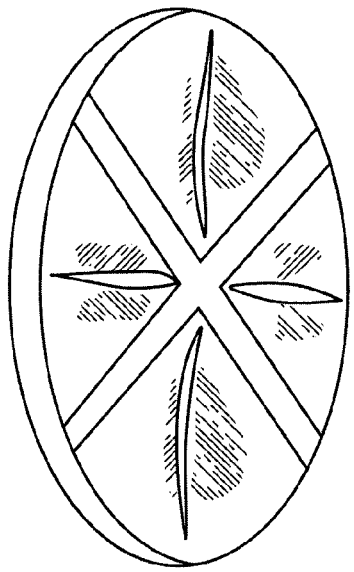
Figure 10C:
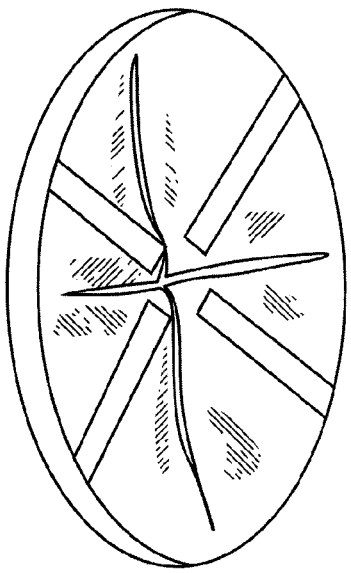

FIGS. 10B-10E shows flap valve limiters that are configured as struts and partial struts for limiting the motion of a flap valve layer having four leaflets. In FIG. 10B, one variation of a layered airflow resistor is shown having four flap valve leaflets in a flap valve layer and a flap valve limiter layer in an adjacent layer that has four struts that meet in the center of the opening regulated by the flap valve, forming two complete cross bars or cross struts. The struts forming the flap valve limiting layer support the flap valve approximately in the center of the each leaflet. In FIG. 10C through 10E, the struts are partial struts of progressively shorter length. The shorter the length of each strut, the greater the possible leak through the otherwise closed flap valve. This effect may be seen in FIG. 10F. In FIG. 10F, back pressure at different flow rates is graphically exemplified for different flap valve limiter variations, including different partial struts. The flap valve limiters corresponding to each curve is indicated to the right of the graph. The target range indicated by the boxed region on the graph is one possible target range (e.g., during expiration when the valve is typically closed). In addition, the airflow resistors shown herein have a single flap valve layer. In some variations the airflow resistor may have multiple flap valve layers. For example, the airflow resistor may include overlapping layers of flap valve leaflets. Multiple layers of flap valve limiters may also be used. Each of these layers may be different in shape (e.g., number of leaflets, etc.). As mentioned above, the leaflets of the flap valve may also overlap when closed. Thus, a single flap valve layer may be formed of different substrate materials (e.g., silicone) that may be connected. Although the examples described above illustrate mostly layers of flap valves and flap valve limiters, the airflow resistor even an airflow resistor layer) is not necessarily formed by layers.

Figure 11A:
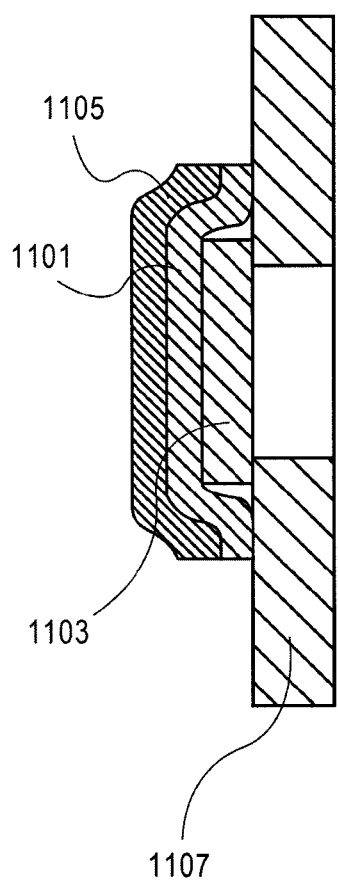
FIG. 11A is a side cross-sectional view of an airflow resistor.
Figure 11B:
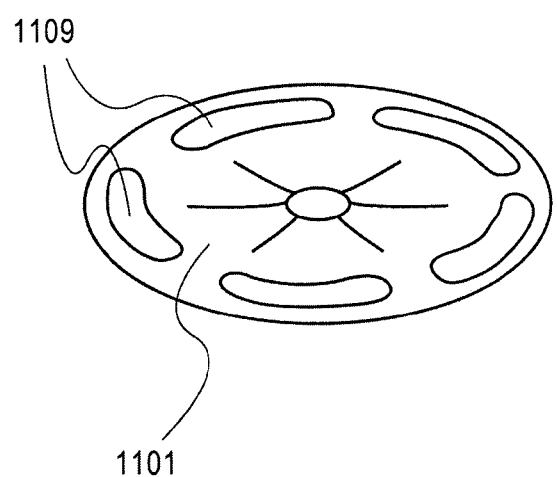
FIG. 11B is another variation of a flap valve layer.

An airflow resistor may be assembled so that the flap valve is free to open in at least one direction (e.g., inhalation) and constrained in a second direction (e.g., exhalation). FIG. 11A shows a side cross-sectional view of an airflow resistor assembled as part of an adhesive nasal device. Additional examples are provided below. In FIG. 11A, the flap valve layer 1101 is layered immediately adjacent to the flap valve limiter 1103. These components are secured in place between an upper 1105 and a lower 1107 substrate. They may be secured in position in any appropriate manner, including adhesive (e.g., by using the adhesive substrate region of the adhesive holdfast), by compression, by welding, by heat staking, etc. FIG. 11B shows a top view of the flap valve layer 1101 of FIG. 11A. In this example, the flap valve layer includes one or more attachment regions 1109, which may be used to help secure the flap valve in position. For example, when an adhesive is used to secure the flap valve layer, the attachment regions (openings 1109) may permit attachment of the layers above and below the flap valve layer (e.g., the substrate layer 1107 and the flap valve limiter 1105, helping to lock the layer into position. This may be particularly useful when the flap valve layer is made of a material such as silicone that is otherwise difficult to bond to.

As mentioned above, any of the devices described herein may also include one or more alignment guide. For example, an alignment guide may comprise a visual alignment guide that a subject can look at to align the device (e.g., in a mirror). For example, the device may be marked by a shape, a text, or a color to help align the device with one or both nasal openings. In one variation, the opening to the airflow resistor is marked by a circle that can be aligned with the subject's nose. In some variations, at least a region of the device may be transparent or opaque, allowing at least a portion of the nasal opening to be seen through the device. In some variations, the alignment guide is a tactile alignment guide. A tactile alignment guide may be felt by the subject (e.g., by the subject's fingers and/or nose). For example, the alignment guide may be a ring, ridge, bump, post, or the like. In some variations, the alignment guide extends at least partially into the subject's nose when the device is worn. For example, an alignment guide may be a cone or conical region.

Figure 13:
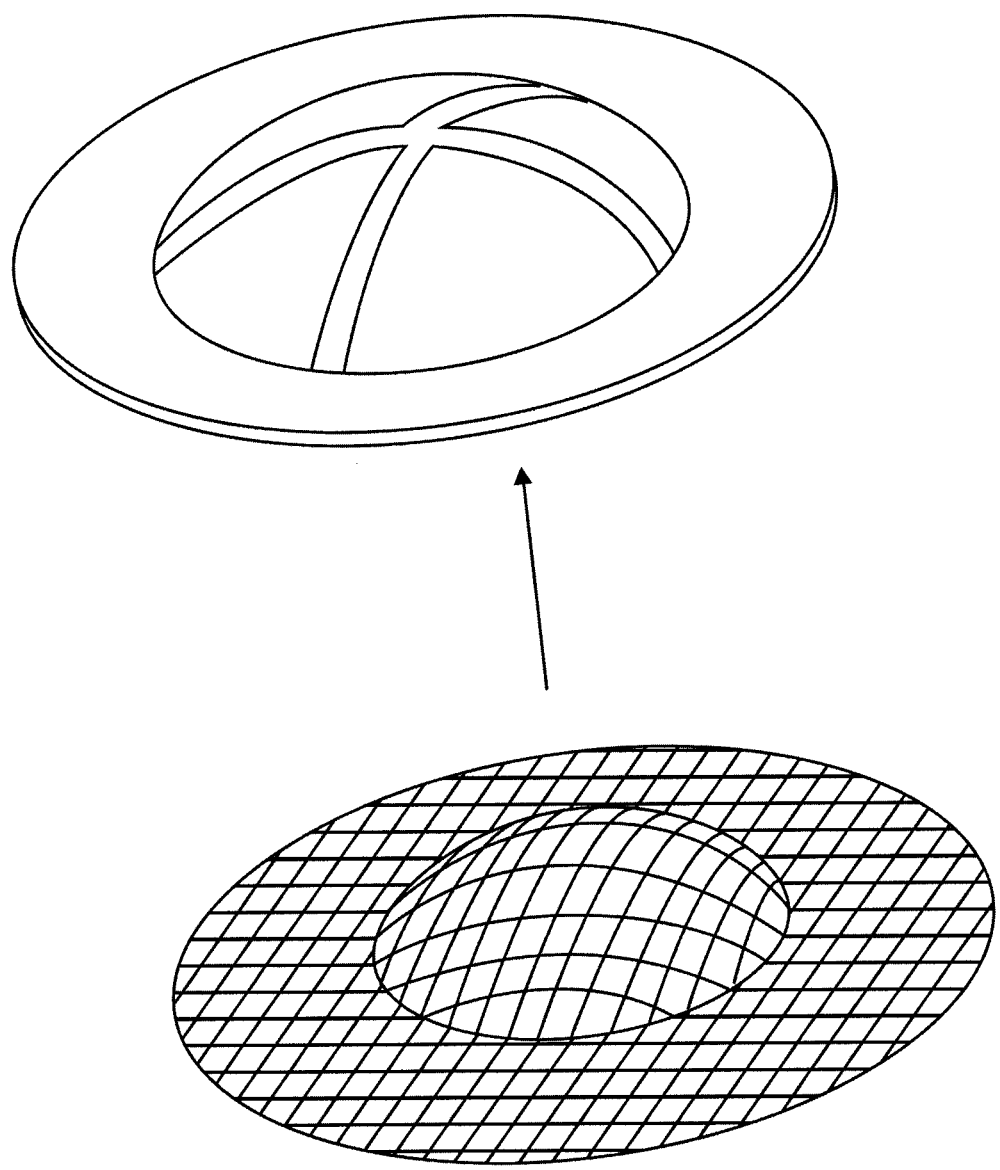

FIGS. 12A to 12D illustrate different alignment guides that may be used. For example, in FIGS. 12A and 12B, the alignment guide is a cone or ring that at encircles the airflow resistor and can be inserted at least partly into the subject's nostril. In FIG. 12C, the alignment guide is a ridge or rim that at least partly surrounds the airflow resistor, and is formed from the substrate (e.g., the holdfast substrate). FIG. 12D shows another variation of an alignment guide in which the guide is made up of posts 1201 that project from the surface of the device. FIG. 13 shows another variation of an airflow resistor, in which the shape of the flap valve and the flap valve limiter act as the alignment guide. In this example, the flap valve limiter is a rigid mesh that is indented (rather than flat), and can therefore be felt by the subject when applying the device. Thus, one variation of an alignment guide that may be used is an indentation or dome that is incorporated into the flap valve limiter. For example, if the flap valve limiter is formed from a plastic mesh, the indentation can be heat formed during manufacture of the device. In this variation, the flap valves are still allowed to freely open (providing little if any resistance) in the first direction, but constrained from opening (or fully opening) in the second direction (providing resistance). As mentioned herein, an alignment guide may also help protect the valve. For example, an alignment guide may prevent interference with a movable portion of the valve (e.g., flap or leaf of a flap valve) by other portions of the device or by the subject's nose, nasal hairs, "boogers," mucous, or the like.

Figure 14A:
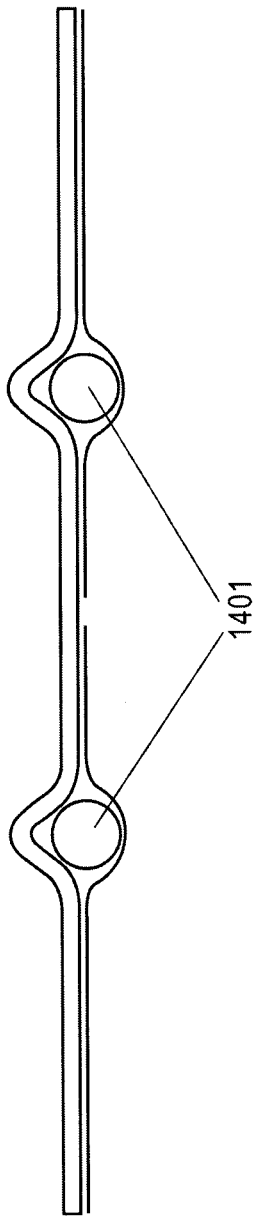
Figure 14B:
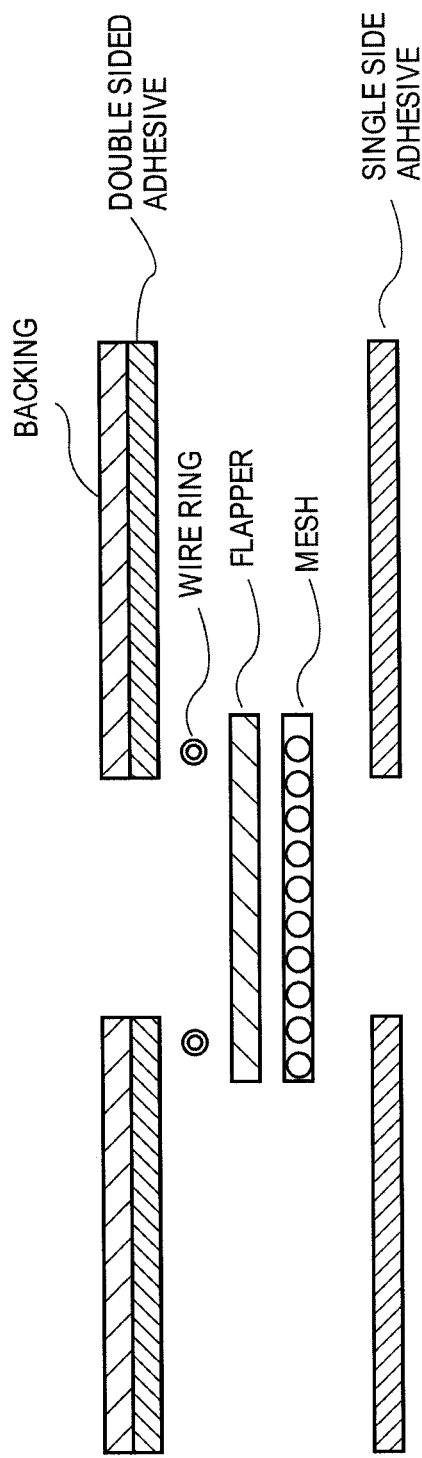

FIGS. 14A and 14B illustrate another tactile alignment guide included as part of the adhesive respiratory device. FIG. 14A shows a cross-section through an adhesive respiratory device that has a ring around the airflow resistor region. This ring may be formed from a wire that is included during the assembly of the device, as schematically illustrate in the exploded view of FIG. 14B.

Figure 15:
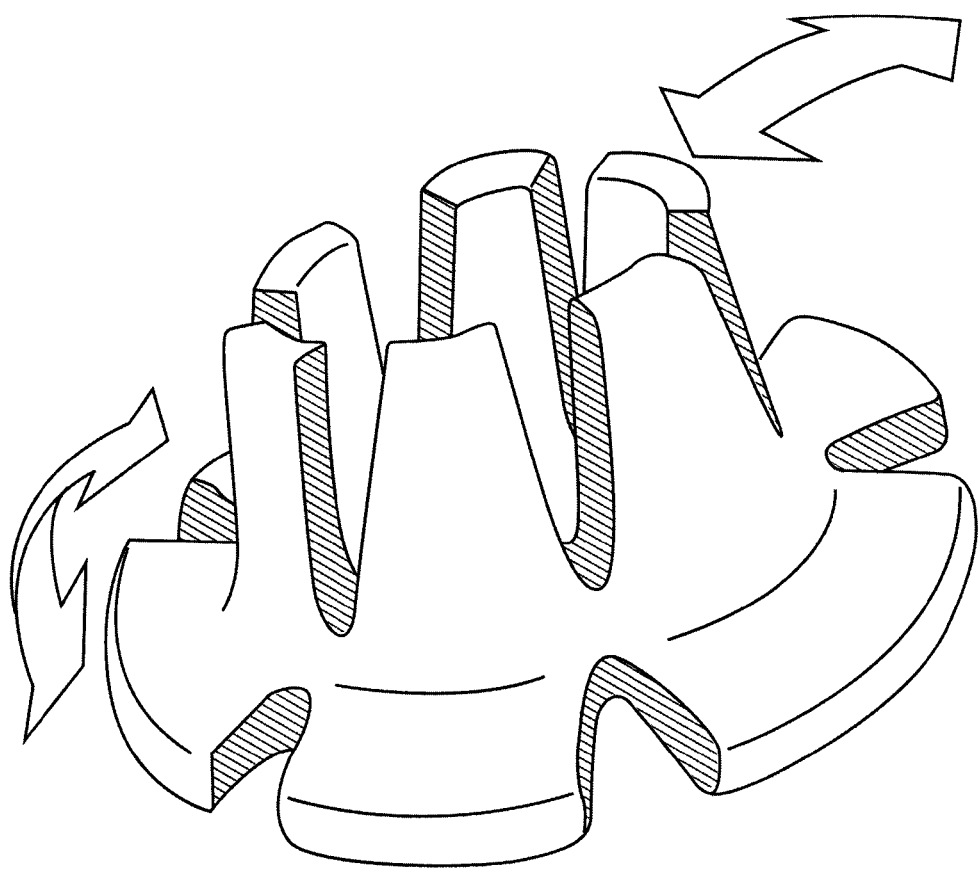

FIG. 15 shows a side perspective view of another alignment guide, similar to the conical alignment guides shown in FIGS. 12A and 12B. In FIG. 13 the alignment guide is somewhat flexible because of the cut-out regions shown. The conical alignment guides may be similar to the rim body region of the adhesive nasal devices described in U.S. Provisional application titled "NASAL DEVICES", filed on Mar. 7, 2007 by Doshi et al., and previously incorporated by reference. Similar to the rim body region, the alignment guides described herein may project into the subject's nostril(s) and may help keep the nostrils open, as well as keeping the adhesive nasal device aligned with the opening.

Figure 16A:
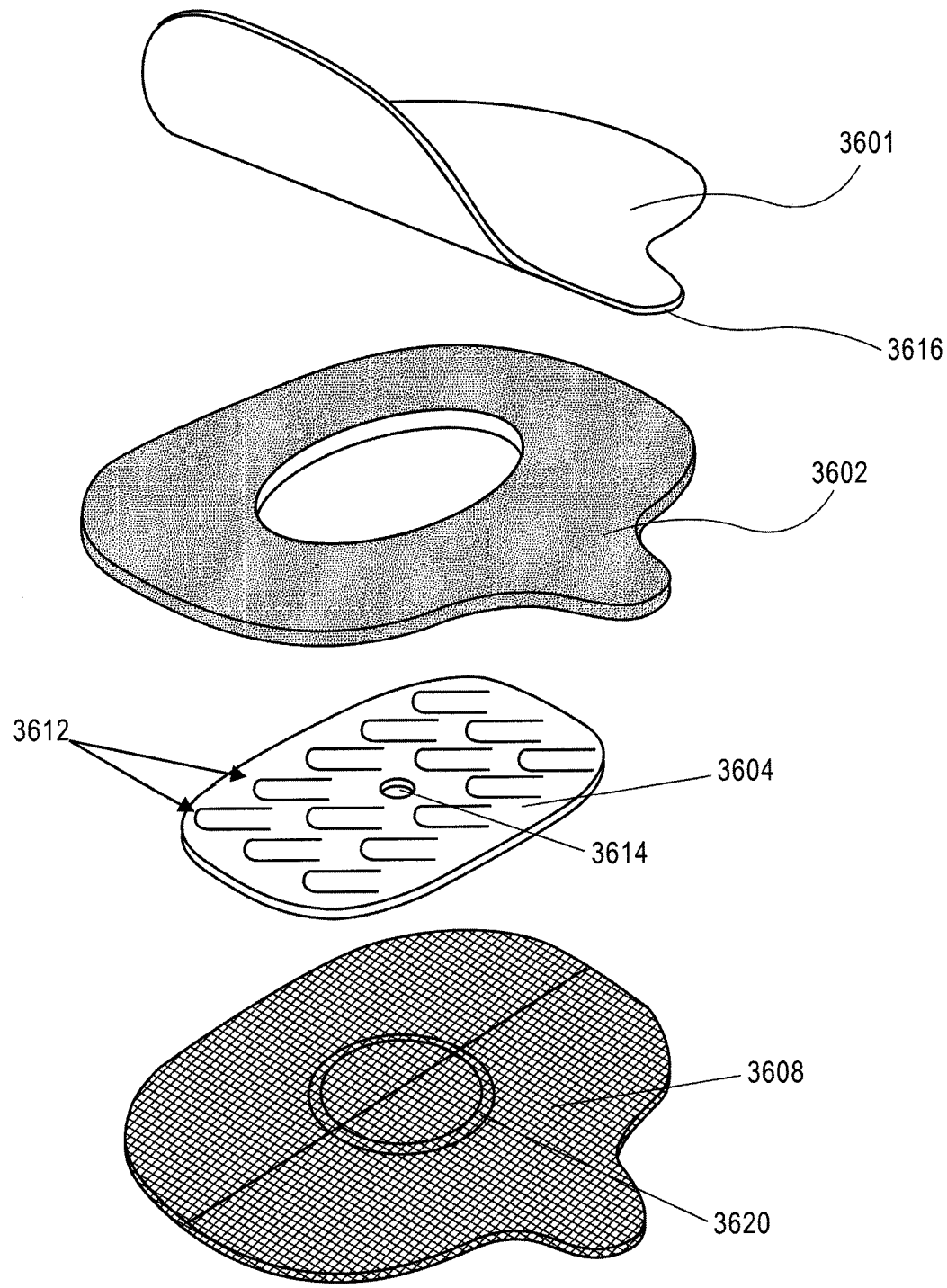
FIGS. 16A and 16B are rim body variations and FIGS. 16C and 16D are flap valve variations.

FIGS. 16A to 16D illustrate one embodiment of an adhesive nasal device as described herein. An exploded view of this exemplary device is illustrated in FIG. 16A. This variation may be particularly well suited to the treatment of snoring, and may be applied by a user at any time, but particularly before sleeping. In FIG. 16A, the adhesive nasal device includes an adhesive substrate (with an adhesive) 3602, a protective cover 3601 that fits over the adhesive, an airflow resistor layer (that has multiple flap valves formed from the valve layer) 3604, and a flap valve limiter 3608 that is at least partially made from a plastic mesh layer. The valve limiter includes a thermoformed locating ring 3620 (formed or attached to the valve limiter layer).

The device shown in FIG. 16A is a single-nostril adhesive nasal device. The airflow resistor layer 3604 in this variation includes multiple flap valves. In some variations, this airflow resistor comprises a silicone material that has been cut to form one or more flap valves. In FIG. 16A, the airflow resistor comprises a plurality of multiple flaps 3612 that are arranged in parallel or any other orientation by being cut from the same piece of silicone. This airflow resistor (flap layer 3604) is secured between the adhesive holdfast layer 3602 and the flap valve limiter 3608. The adhesive layer may be made of a foam material that is adhesive on one or both sides. When the adhesive holdfast layer is adhesive on both sides, it can be used to secure the airflow resistor between the adhesive holdfast layer and the flap valve limiter layer 3608. The outer perimeter of the airflow resistor layer 3604 is smaller than the outer perimeter of the flap valve limiter layer 3608, but larger than the inner perimeter of the airflow resistor layer 3602. Thus, the airflow resistor layer can be held by the adhesive on the adhesive holdfast 3602 against the flap valve limiter 3608, and the adhesive holdfast layer 3602 can similarly be secured to the flap valve limiter 3608 by the adhesive. Additional attachments may also be used to secure the device components together (e.g., welds, clips, etc.).

Figure 16B:
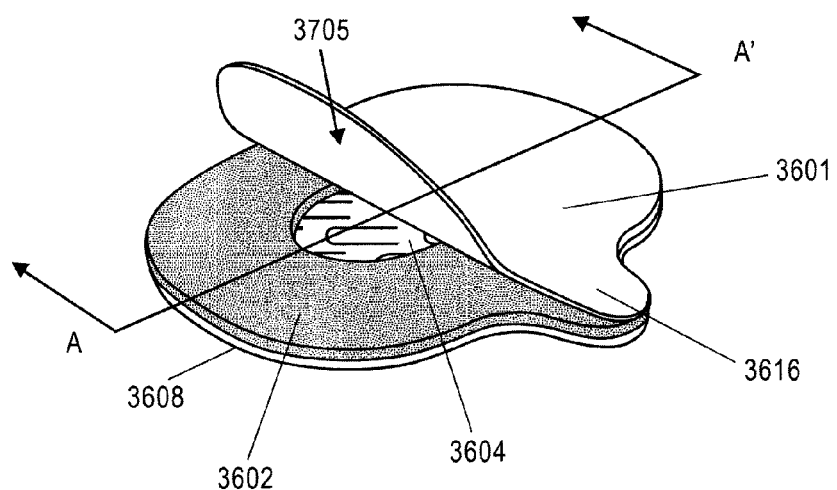

FIG. 16B shows a perspective view of an assembled nasal device similar to the device shown in FIG. 16A. In FIG. 16B, the protective cover 3601 has been partially peeled back to expose the central passageway opening 3705 formed when the foam adhesive holdfast layer 3602 is combined with the flap valve limiter layer 3608 and secures the airflow resistor layer 3604 therebetween. The flap valves formed in the airflow resistor layer 3604 that are free to move in the opening of this passageway may thus open to allow air to flow through the central passageway after the air passes through the plastic mesh of the flap valve limiter layer 3608.

The adhesive nasal device shown in FIGS. 16A and 16B also includes a tab or grip region 3616, as previously described. In addition, the airflow resistor layer 3604 may include at least one leak pathway 3614 (shown in FIG. 16A as a hole 3614), that permits air to pass even when the flap valves of the airflow resistor layer are held "closed" against the mesh. In some embodiments, a separate leak path may not be present.

Figure 16C:
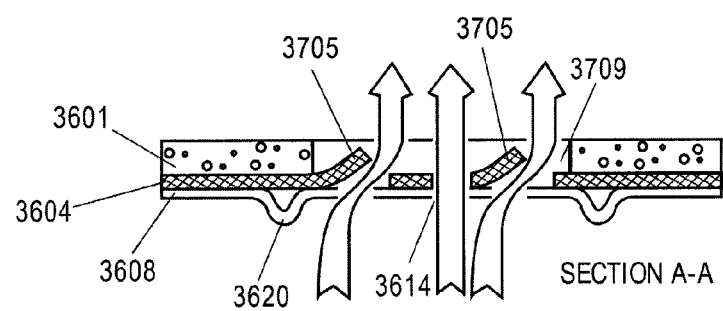
Figure 16D:
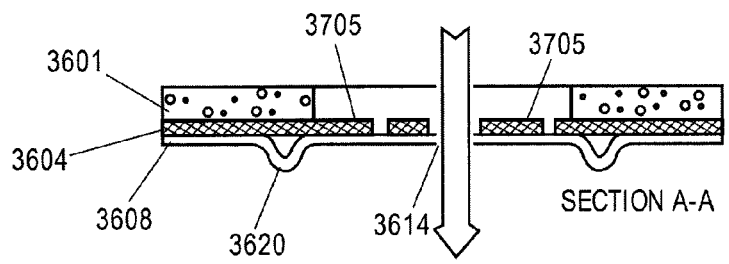

FIGS. 16C and 16D illustrate airflow through the device of FIG. 16B when it is worn by a subject during inhalation and expiration, respectively. Both FIGS. 16C and 16D show a cross-section through the device of FIG. 16B taken along lines A-A'. For example, in FIG. 16C, the large arrows pointing upwards represent airflow when the device is worn over a subject's nose. Airflow passes from the outside of the nose, though the adhesive nasal respiratory device, and into the nasal passageway during inhalation. The central arrow shows airflow through the leak pathway 3614, whereas the right and left arrows show airflow when the airflow resistor (parallel flap valves 3705) open during inhalation. The flap valves 3705 open upwards into the passageway formed through the device 3709, permitting air to flow through the airflow resistor as well as though the leak pathway.

During exhalation (as shown in FIG. 16D), the flap valves of the airflow resistor 3705 are blocked from opening in the direction of exhalation (indicated by the large arrow showing passage of air through the leak pathway) because of the mesh of the flap valve limiter layer 3608. Thus, the airflow resistors remain closed, and the only airflow through the device passes through the leak pathway, as indicated. In some embodiments, the multiple flaps 3612 may not completely seal on exhalation and this lack of seal may intentionally create the leak path. In other embodiments, portions of the flaps may be removed (or they may be notched for example) in order to create a desired leak path. As previously mentioned, the airflow resistor and/or alignment guide may be made of any appropriate material. Exemplary materials may include: metals, plastics, rubbers, ceramics, wood, chrome, or combinations thereof. Other materials may include acrylics, latex, polyethylene, polypropylene, polystyrene, polyvinyl chloride, polyvinylidene chloride, polyvinyl acetate, polyacrylate, styrene-butadiene copolymer, chlorinated polyethylene, polyvinylidene fluoride, ethylene-vinyl acetate copolymer, ethylene-vinyl acetate-vinyl chloride-acrylate copolymer, ethylene-vinyl acetate-acrylate copolymer, ethylene-vinyl acetate-vinyl chloride copolymer, nylon, acrylonitrile-butadiene copolymer, polyacrylonitrile, polyvinyl chloride, polychloroprene, polybutadiene, thermoplastic polyimide, polyacetal, polyphenylene sulfide, polycarbonate, thermoplastic polyurethane, thermoplastic resins, thermosetting resins, natural rubbers, synthetic rubbers (such as a chloroprene rubber, styrene butadiene rubber, nitrile-butadiene rubber, and ethylene-propylene-diene terpolymer copolymer, silicone rubbers, fluoride rubbers, and acrylic rubbers), elastomers (such as a soft urethane, water-blown polyurethane), and thermosetting resins (such as a hard urethane, phenolic resins, and a melamine resins).

Biocompatible materials may be used, particularly for those portions of the device which may contact a user. In addition to some of the materials described above, the biocompatible materials may also include a biocompatible polymer and/or elastomer. Suitable biocompatible polymers may include materials such as: a homopolymer and copolymers of vinyl acetate (such as ethylene vinyl acetate copolymer and polyvinylchloride copolymers), a homopolymer and copolymers of acrylates (such as polypropylene, polymethylmethacrylate, polyethylmethacrylate, polymethacrylate, ethylene glycol dimethacrylate, ethylene dimethacrylate and hydroxymethyl methacrylate, and the like), polyvinylpyrrolidone, 2-pyrrolidone, polyacrylonitrile butadiene, polyamides, fluoropolymers (such as polytetrafluoroethylene and polyvinyl fluoride), a homopolymer and copolymers of styrene acrylonitrile, cellulose acetate, a homopolymer and copolymers of acrylonitrile butadiene styrene, polymethylpentene, polysulfones polyimides, polyisobutylene, polymethylstyrene and other similar compounds known to those skilled in the art. Teflon, Mylar, PFA, LDPE, Hytrel, HDPE and polyester may also find use in any components of the devices.

Materials that biocompatible and/or sterilizable may also be preferred, for example, medical grade plastics such as Acrylonitrile Butadiene Styrene (ABS), latex, polypropylene, polycarbonate, and polyetheretherketone. The forgoing materials are intended as illustrations only.

FIG. 17 is a matrix illustrating just some of the variations of the adhesive nasal devices that may be formed from the different variations of airflow resistor components. For example, any flap valve geometry (e.g., "s-curve", "fish scales", "pie slice", etc.) may be used with single nostril, bridged nostril or both nostril geometries, any alignment method (e.g., visual aligner, tactile, etc.), and any flap valve limiter (e.g., mesh, full mesh, local mesh, struts, etc.).

Adhesive Holdfast

The adhesive nasal devices described herein may also include an adhesive holdfast for securing the device in communication with a nasal cavity. The adhesive holdfast may include one or more adhesive surfaces that are suitable for use against a subject's body (e.g., skin and/or nasal cavity). Thus, the adhesive holdfast may include a biocompatible adhesive. The adhesive holdfast may facilitate the positioning and securing of the device in a desired location with respect to the subject's nose, such as over, partially over, partially within, or within (e.g., substantially within) a nostril. An adhesive holdfast may be configured to secure the device to any appropriate region of the subject's nose, nasal passage, or nasal cavity, including the nostrils, nares or nasal chambers, limen, vestibule, greater alar cartilage, alar fibrofatty tissue, lateral nasal cartilage, agger nasi, floor of the nasal cavity, turbinates, sinuses (frontal, ethmoid, sphenoid, and maxillary), and nasal septum. The term "nasal cavity" may refer to any sub-region of the Nasal Fossa (e.g., a single nostril, nare, or nasal chamber) and includes or is defined by any of the anatomical terms listed above.

In general, the adhesive holdfast is configured to be applied predominantly to the outside of the nose (e.g., the skin surrounding the nasal opening or nostril). In some versions, the holdfast may also form a seal between the respiratory device and the nose, so that at least some of the air exchanged between the outside of the patient and the nostril must pass through the respiratory device. In some versions, the holdfast seals the device in communication with the nose completely, so that all air through the nostril (or nostrils) must be exchanged through the device. In some versions, the holdfast seal is incomplete, so that only some of the air exchanged between the patient and the external environment passes through the device. As used herein, "air" may be air from environment external to the patient, or it may be any respiratory gas (e.g., pure or mixed oxygen, $CO_2$, heliox, or other gas mixtures provided to the user).

The adhesive holdfast may be flexible so that it conforms to the surface of the subject's skin, which may be relatively irregularly shaped, and may include hair and the like. In some variations, the adhesive holdfast is made of a material that permits the passage of water vapor, liquid water, sweat and/or oil, which may enhance comfort. The adhesive holdfast may also include a texture or patterned relief surface to enhance bonding to the subject's nose region.

The adhesive holdfast may be made of layers. Thus, the adhesive holdfast may be referred to as a layered holdfast (or layered adhesive holdfast) For example, the adhesive holdfast may include a substrate layer to which a biocompatible adhesive is applied. The substrate is typically a flat (predominantly 2-sided) material that is flexible. An adhesive may be present on at least one surface of the substrate, allowing it to adhere to the subject's nasal region. In some variations, the substrate layer is itself adhesive without needing an additional adhesive. An additional protective cover may also be removably attached to the adhesive of the adhesive layer. The protective cover may allow the device (and particularly the adhesive holdfast) to be manipulated without inadvertently sticking the device to the fingers or other parts of the body and it may also prevent contamination of the adhesive. The liner may be a removable paper or other film that can be peeled off or otherwise removed to expose the adhesive. In some variations, the adhesive of the adhesive holdfast is activatable. For example, the adhesive becomes 'sticky' only after exposure to an activator (e.g., water, air, light, etc.). In some variations, an adhesive could be applied to the nose in a liquid form first, than the device is applied.

In some variations, a protective cover is not used. As already mentioned, in some variations, the substrate and adhesive are a single layer, so that the substrate comprises an adhesive material, or a material that can be activated to become adhesive. The adhesive holdfast may comprise any appropriate material. For example, the adhesive substrate may be a biocompatible material such as silicone, polyethylene, or polyethylene foam. Other appropriate biocompatible materials may include some of the materials previously described, such as biocompatible polymers and/or elastomers. Suitable biocompatible polymers may include materials such as: a homopolymer and copolymers of vinyl acetate (such as ethylene vinyl acetate copolymer and polyvinylchloride copolymers), a homopolymer and copolymers of acrylates (such as polypropylene, polymethylmethacrylate, polyethylmethacrylate, polymethacrylate, ethylene glycol dimethacrylate, ethylene dimethacrylate and hydroxymethyl methacrylate, and the like), polyvinylpyrrolidone, 2-pyrrolidone, polyacrylonitrile butadiene, polyamides, fluoropolymers (such as polytetrafluoroethylene and polyvinyl fluoride), a homopolymer and copolymers of styrene acrylonitrile, cellulose acetate, a homopolymer and copolymers of acrylonitrile butadiene styrene, polymethylpentene, polysulfones polyimides, polyisobutylene, polymethylstyrene and other similar compounds known to those skilled in the art. Structurally, the substrate may be a film, foil, woven, non-woven, foam, or tissue material (e.g., poluelofin non-woven materials, polyurethane woven materials, polyethylene foams, polyurethane foams, polyurethane film, etc.).

In variations in which an adhesive is applied to the substrate, the adhesive may comprise a medical grade adhesive such as a hydrocolloid or an acrylic. Medical grade adhesives may include foamed adhesives, acrylic co-polymer adhesives, porous acrylics, synthetic rubber-based adhesives, silicone adhesive formulations (e.g., silicone gel adhesive), and absorbent hydrocolloids and hydrogels.

In some variations, the adhesive is a structural adhesive. For example, the adhesive may adhere based on van der Walls forces. Patents no. U.S. Pat. No. 7,011,723, U.S. Pat. No. 6,872,439, U.S. Pat. No. 6,737,160, and U.S. Pat. No. 7,175, 723 describe setal-like structures whose shape and dimension provide adhesive force. These patents are herein incorporated by reference in their entirety.

The removable liner layer may be made of any appropriate matter that may be released from the adhesive. For example, the liner material may comprise craft paper. In some variations, the liner material comprises polyethylene film, or polyethylene coated paper (e.g. kraft paper). The liner may be any of the other materials described herein.

In general, any of the materials commonly used in the manufacture of bandages (particularly disposable bandages such as BAND-AIDS™), ostomy kits, and wound care products may be used in any or all components of devices described herein. An adhesive layer (or an adhesive holdfast layer) may be formed in any appropriate method, particularly those described herein. For example, an adhesive layer may be formed by cutting (stamping, die cutting, laser cutting, etc.) the adhesive substrate, biocompatible adhesive, and protective cover into the desired shape. Multiple steps may be used to form the adhesive layer. For example, the adhesive layer may be formed by cutting (or otherwise forming) the outer perimeter, then by cutting (or otherwise forming) an inner opening.

In general, the adhesive holdfast may comprise any appropriate shape that allows the airflow resistor to be positioned with respect to one or both nasal passages so that some (or most) of the airflow through the nasal passages must pass through the adhesive nasal device. In some variations, the adhesive holdfast attaches to the nose (or nasal passage) and forms a partial or complete seal therewith, thereby channeling airflow into or out of the nasal passageway through the device, and also securing the device in position. Thus, there are many designs that would achieve these criterions, many of which are described below.

It is not necessary that the entire adhesive holdfast region include an adhesive, although many of the substantially flat holdfast regions described in the preceding figures may have a biocompatible adhesive over much of the skin-contacting surface (although it may be covered by a protective cover that can be at least partially removed later). In some variations only a subset of the holdfast region (including the outer layer) includes an adhesive. For example the region adjacent to the rim body may not include an adhesive, or the region beneath the tabs or grips may not include an adhesive.

In some variations, the adhesive nasal devices described herein are adapted to fit different users having a diversity of sizes and shapes, particularly the shapes and sizes of their noses. As already described, the devices, including particularly the adhesive holdfast region, may be configured to that it is adaptable to different nose shapes. In some variations, the holdfast region may extend into the nostril, rather than just adhering around the outer surface of the nasal passages. For example, the adhesive holdfast may include a region that projects into the nostril, and can be secured against the walls of the nostril. In some variations, the internally-projecting regions may comprise a compressible material (e.g., a foam or the like) so that they may be secured within the nasal passages, and/or may cushion the inner rim base region (or any other portion of the adhesive nasal device) that projects into the subject's nostrils. Thus, in some variations, the inwardly-projecting portion of the holdfast is smaller than the nasal opening, and does not necessarily contact the sides of the subject's nasal passage.

Exemplary Laminate of Adhesive Nasal Devices

Figure 18:
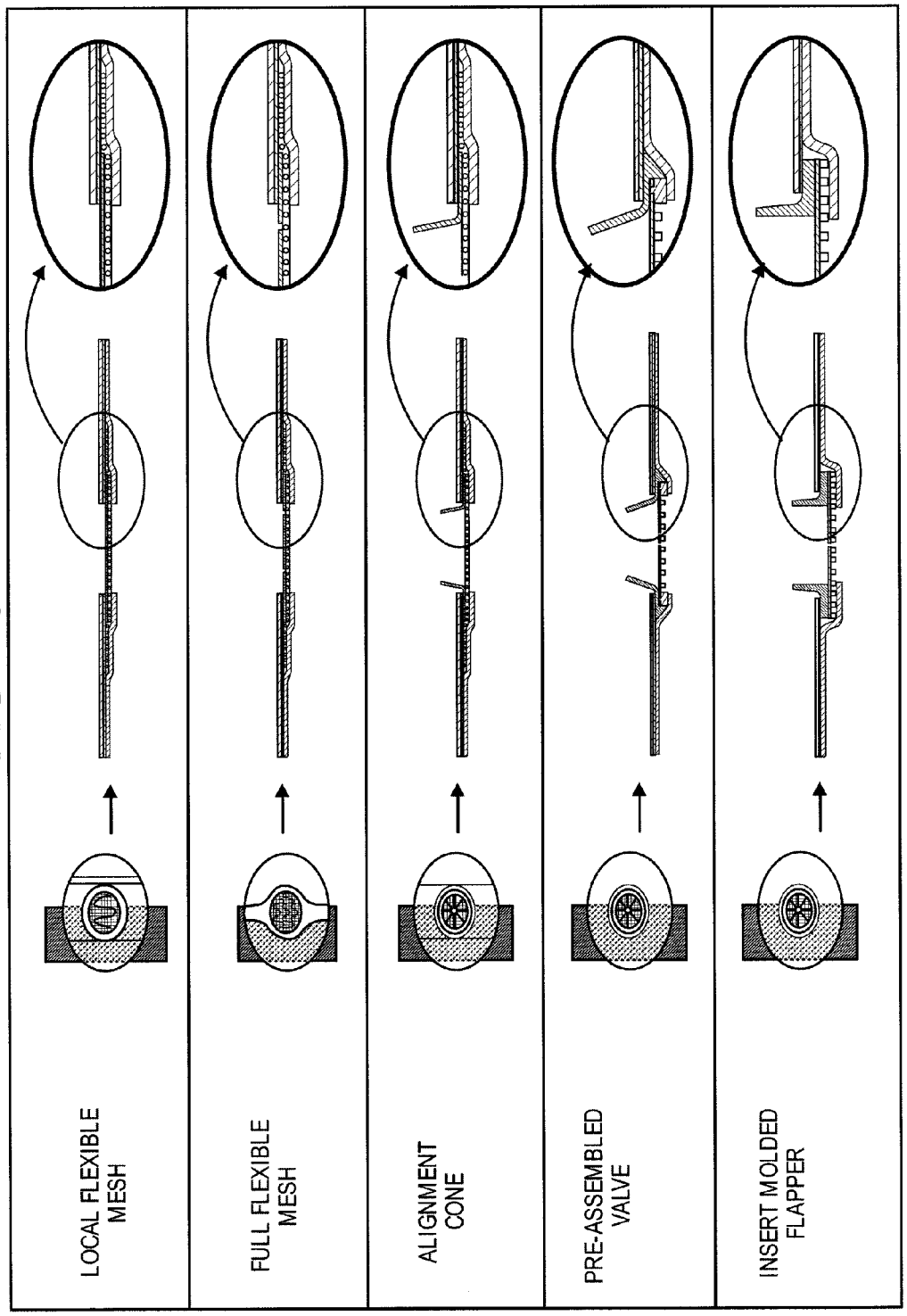
FIG. 18 shows five exemplary variations of the layered nasal devices.
Figure 20A:
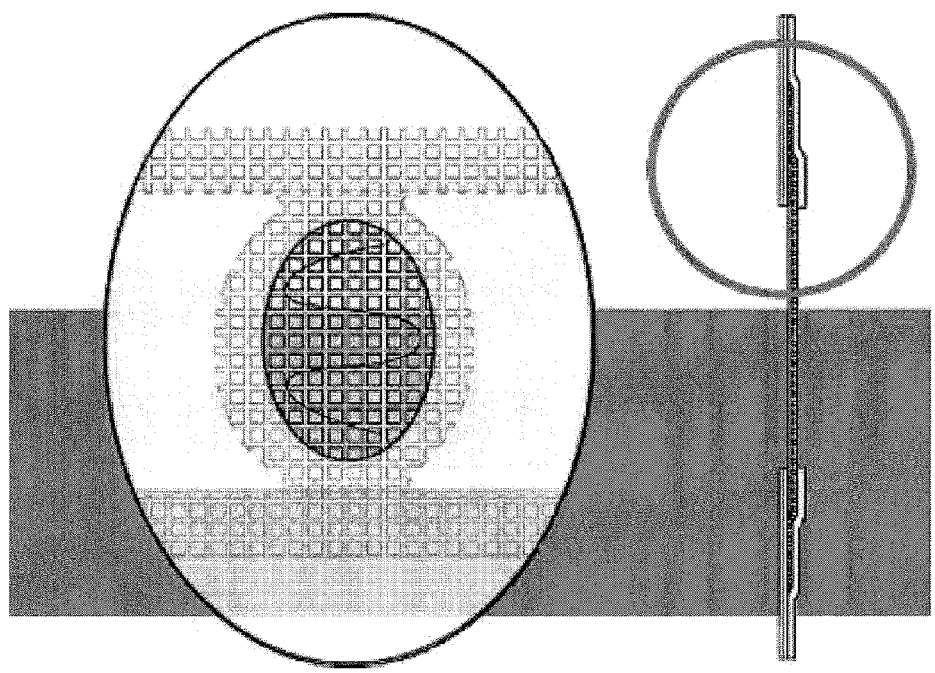
Figure 20G:
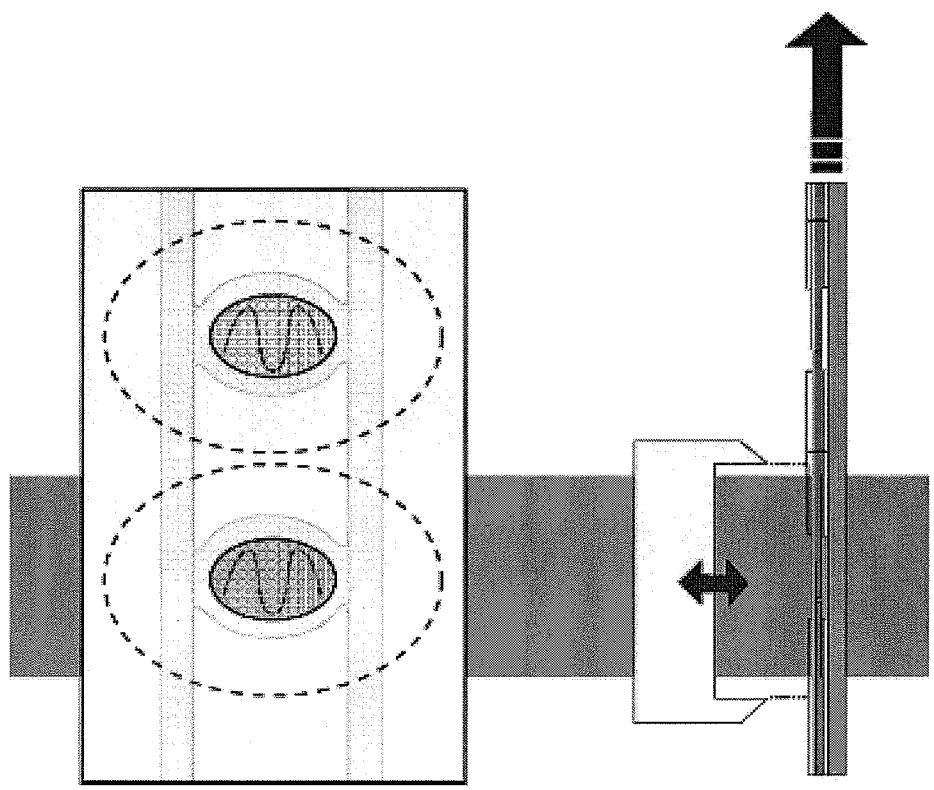
Figure 22A:
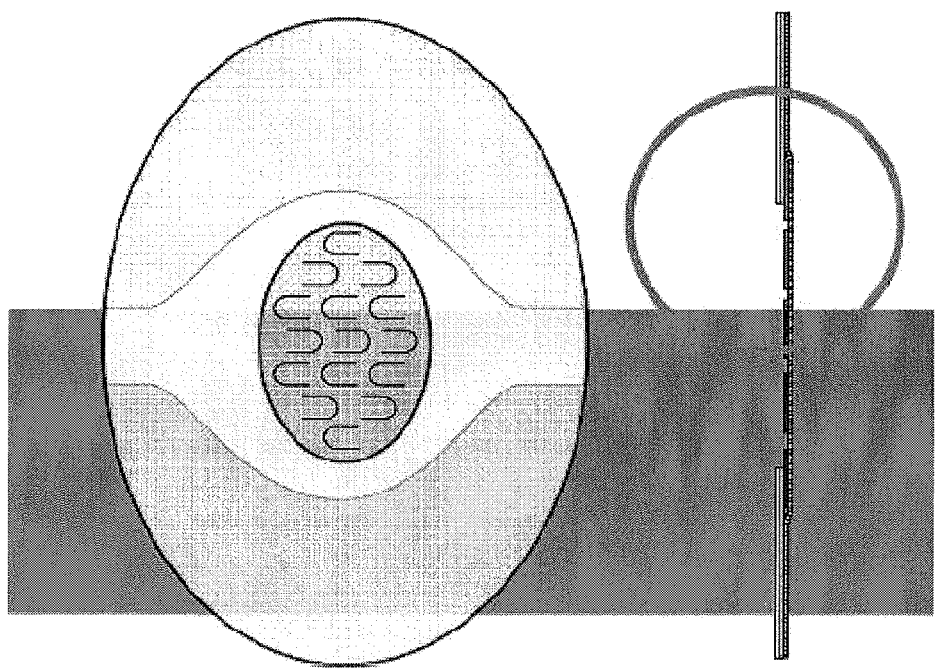
Figure 22F:
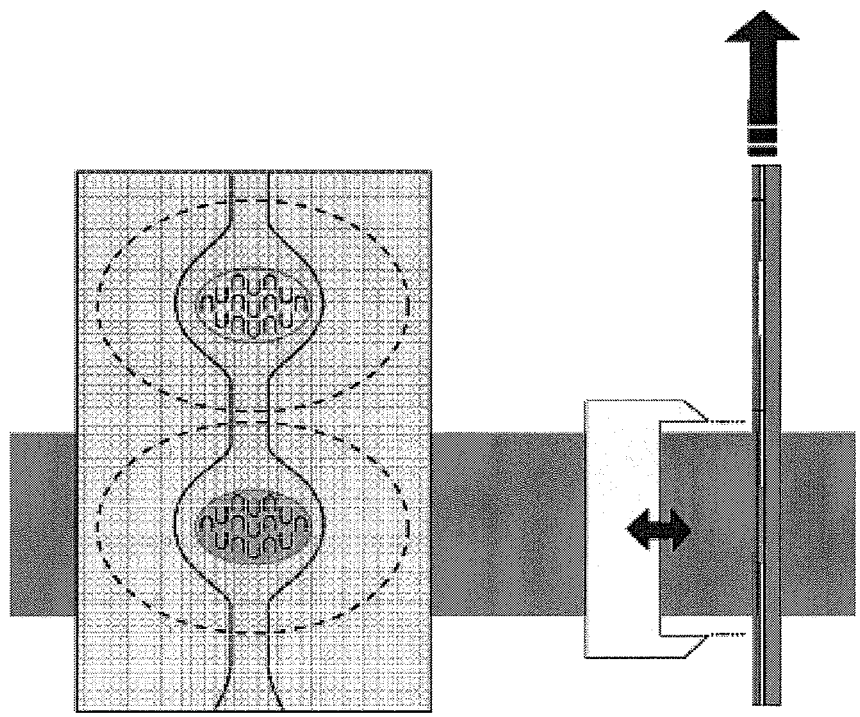

FIG. 18 shows five exemplary variations of the layered nasal devices described herein. Each of these variations is described briefly below with accompanying drawings.

FIGS. 19A and 19B show one variation of a layered nasal device having an airflow resistor including a flap valve limiter that is made of a flexible mesh. This flap valve limiter may be referred to as a local flexible mesh valve limiter because this mesh layer is trimmed, and is not coextensive with the adhesive of the adhesive holdfast region (e.g., it is underlies just the flap valve layer). This may be seen in the cross-section shown in FIG. 19A, and in the circular detail region shown in FIG. 19B. The left side of FIG. 19B shows a bottom view of this variation of an adhesive nasal device.

The adhesive nasal device may be formed by sequentially layering onto a backing layer that protects one side of double-sided adhesive (forming the adhesive holdfast), cutting out (e.g., die-cutting) an opening through this adhesive holdfast substrate, applying the flap valve layer (which may be any of the flap valves described above, but is shown here as a silicone S-cut flap valve) so that the flap valve spans the opening, applying the pre-trimmed mesh (over the flap valve spanning the opening, and securing another (single-sided) adhesive layer having a corresponding opening over the sandwiched flap valve and mesh.

The adhesive nasal device shown in FIGS. 19A and 19B is shown being worn by a subject in FIGS. 19C to 19E. FIGS. 20A-20G illustrate one method of manufacturing multiple adhesive nasal devices as shown in FIGS. 19A and 19B.

FIGS. 21A and 21B show another variation of a layered nasal device having an airflow resistor including a flap valve limiter that is made of a flexible mesh. This flap valve limiter may be referred to as a full flexible mesh because the mesh forming this limiter layer is not trimmed, and extends further than the opening through the adhesive holdfast region. This may be seen in the cross-section shown in FIG. 21A, and in the circular detail region shown in FIG. 21B. The left side of FIG. 21B shows a top view of a partially constructed adhesive nasal device.

This device may be formed by sequentially layering a backing layer protecting one side of double-sided adhesive (forming the adhesive holdfast), cutting out (e.g., via die-cutting) an opening through this substrate, applying a flap valve layer (e.g., any of the valves described above, shown here as a fish-scale flap valve) spanning this opening, and applying the un-trimmed mesh over the flap valve layer to sandwiched the flap valve with the mesh.

FIGS. 22A-22F illustrate one method of manufacturing multiple adhesive nasal devices as shown in FIGS. 19A and 19B.

Figure 23A:
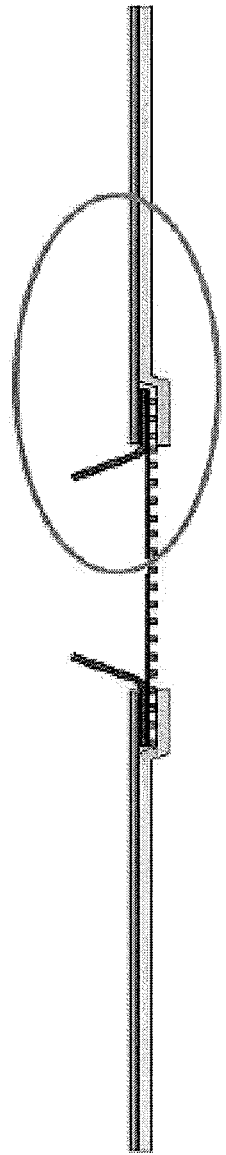
FIGS. 23A and 23B show another layered nasal device.
Figure 23B:
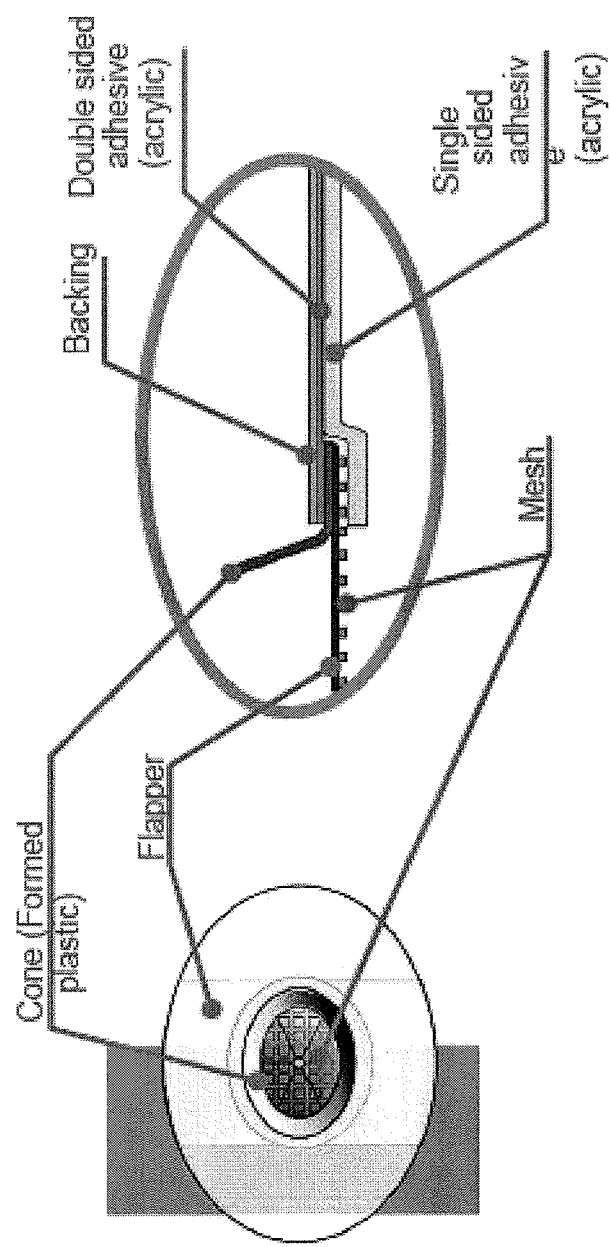

FIGS. 23A and 23B show another variation of a layered nasal device having an airflow resistor including a flap valve limiter that is made of a mesh and includes an alignment guide shown here as a cone. This may be seen in the cross-section shown in FIG. 23A, and in the detail region shown in FIG. 23B. The left side of FIG. 23B shows a top view of a partially constructed adhesive nasal device.

Similar to the devices above, this device may be formed by sequentially layering a backing layer protecting one side of double-sided adhesive (forming the adhesive holdfast), cutting out (e.g., via die-cutting) an opening through this substrate, inserting the alignment guide cone into the opening, applying a flap valve layer (e.g., any of the valves described above, shown here as a silicone six pie-cut flap valve) spanning this opening, applying the pre-trimmed mesh over the flap valve spanning the opening, and securing another (single-sided) adhesive layer having a corresponding opening over the sandwiched flap valve and mesh.

Figure 23D:
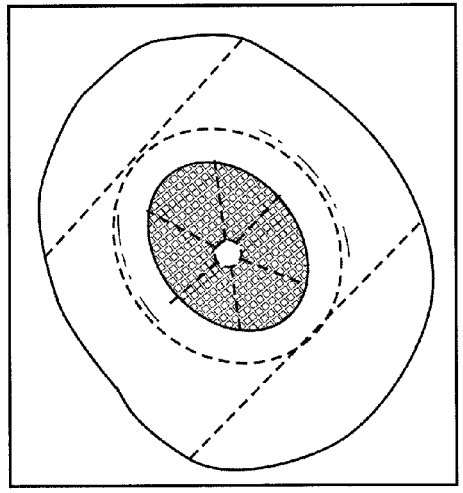
FIGS. 23C and 23D are examples of the device shown in FIGS. 23A and 23B, and FIGS. 23E and 23F show a subject wearing the device of FIGS. 23C and 23D.
Figure 23F:
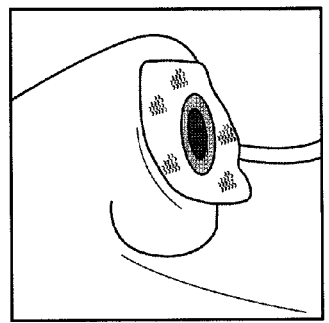
Figure 23C:
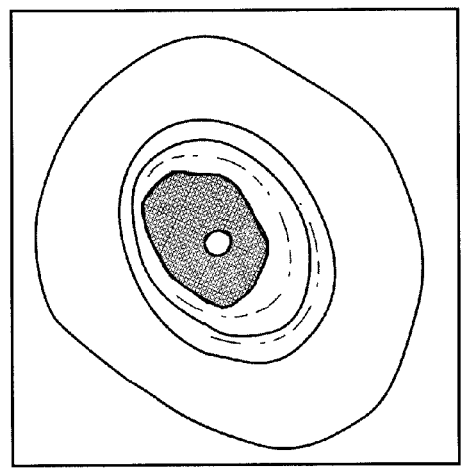
Figure 23E:
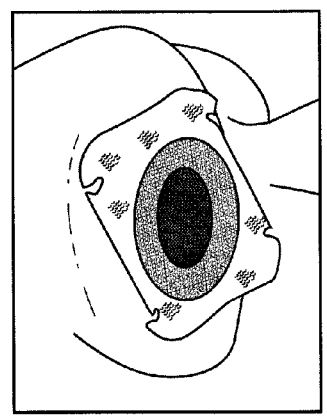
Figure 24A:
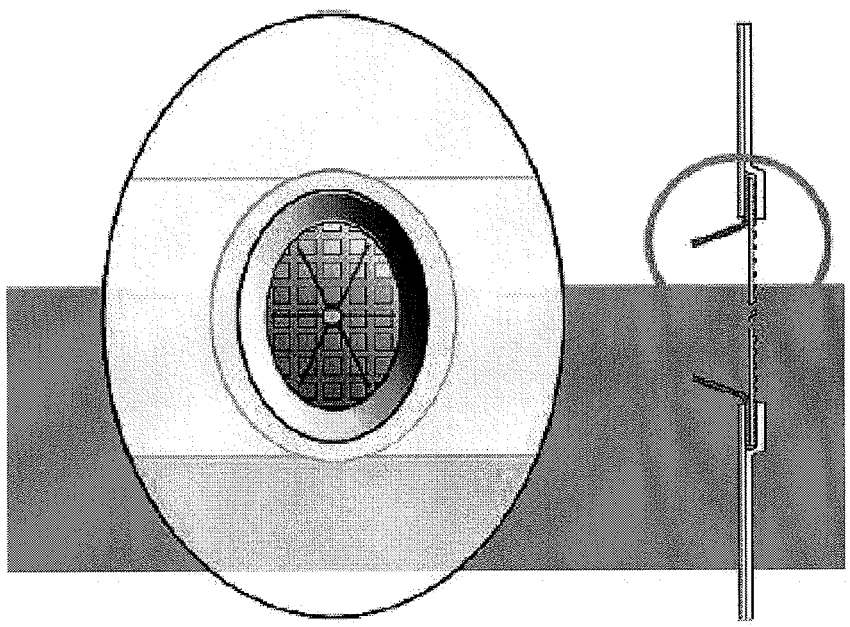
Figure 24F:
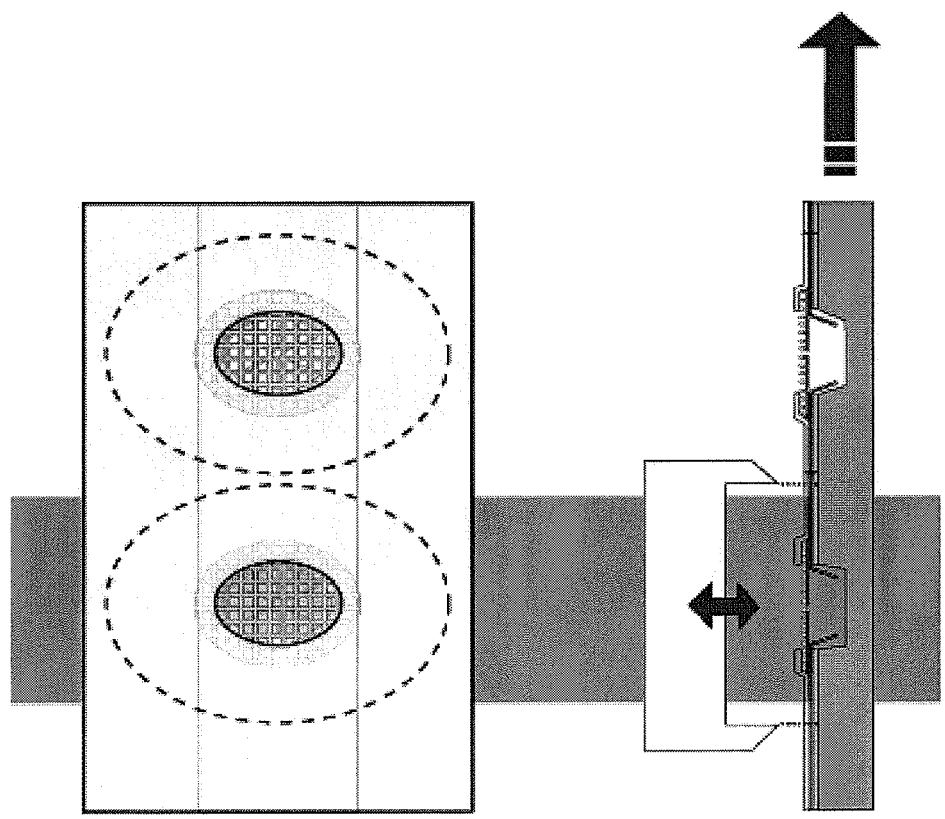

The adhesive nasal device shown in FIGS. 23A and 23B is illustrated in FIGS. 23C and 23D, and is shown worn by a subject in FIGS. 23E and 23F. FIGS. 24A-24F illustrate one method of manufacturing multiple adhesive nasal devices as shown in FIGS. 23A and 23B.

Figure 25A:
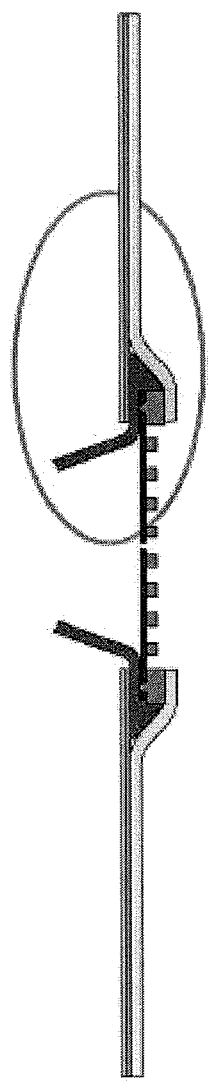
FIGS. 25A and 25B show another layered nasal device.
Figure 25B:
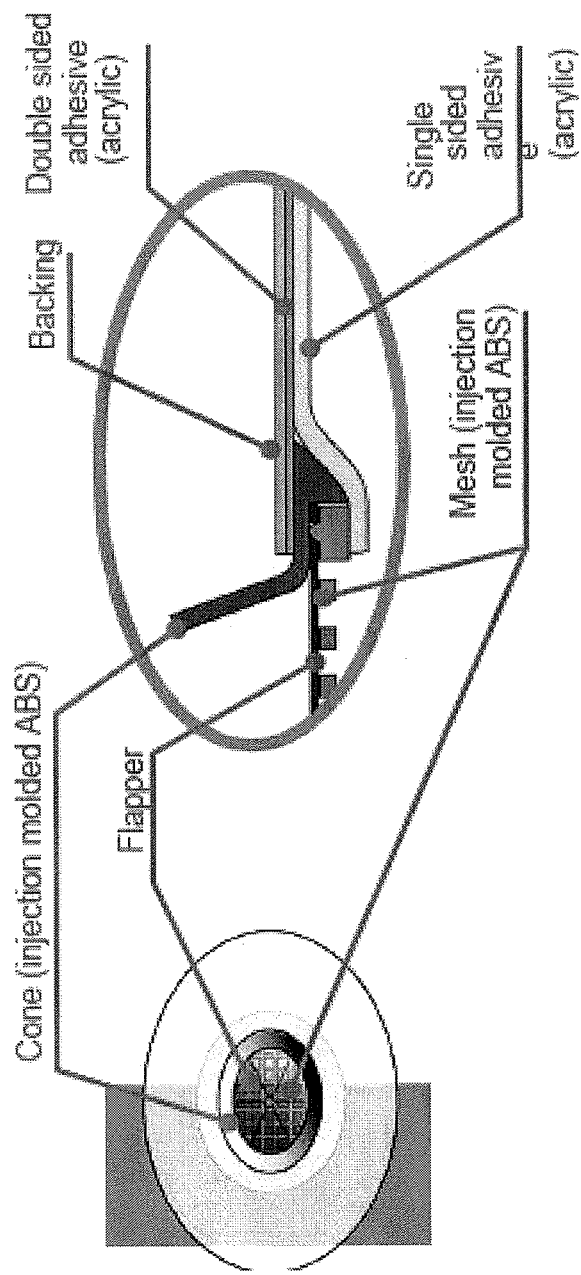

FIGS. 25A and 25B show another variation of a layered nasal device having an airflow resistor including a flap valve limiter that is a pre-molded mesh formed by injection molding and includes a conical alignment guide. This may be seen in the cross-section shown in FIG. 25A, and in the detail in the circled region shown in FIG. 25B. The left side of FIG. 25B shows a top view of a partially formed adhesive nasal device.

This variation of the adhesive nasal device may be formed by sequentially layering onto a backing layer protecting one side of double-sided adhesive (forming the adhesive holdfast), inserting the pre-molded alignment guide cone into the opening, applying a flap valve layer (e.g., any of the valves described above, shown here as a silicone six pie-cut flap valve), inserting the pre-molded mesh, and securing another (single-sided) adhesive layer having a corresponding opening to secure the mesh, valve and cone into position.

Figure 25C:
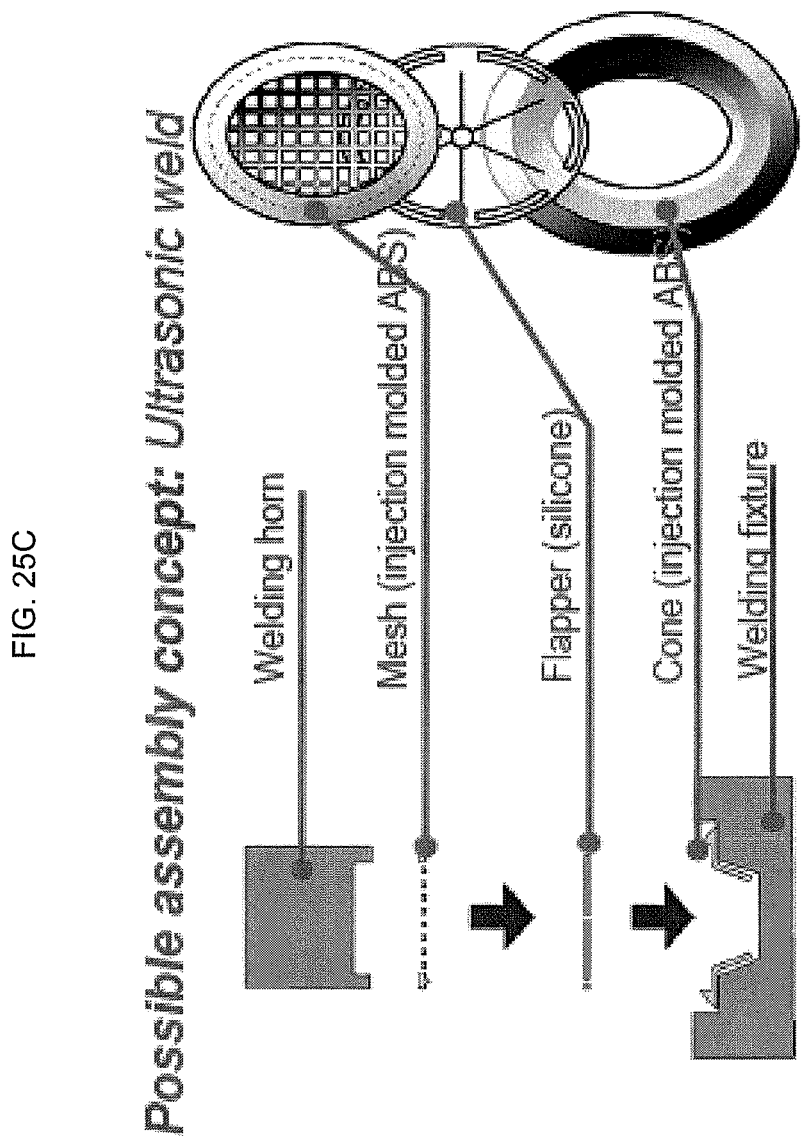
FIG. 25C shows one method of assembling the adhesive nasal device shown in FIGS. 25A and 25B.

One possible method of assembling the adhesive nasal device shown in FIGS. 25A and 25B is illustrated in FIG. 25C. In this example, a method of manufacturing the cone (application guide), flap valve and flap valve limiter (mesh) by ultrasonic welding is described. A welding horn and welding fixture are used to ultrasonically weld these three components together to form a subassembly, as shown. This subassembly may then be inserted into the opening formed in the adhesive substrate (adhesive holdfast).

Figure 26A:
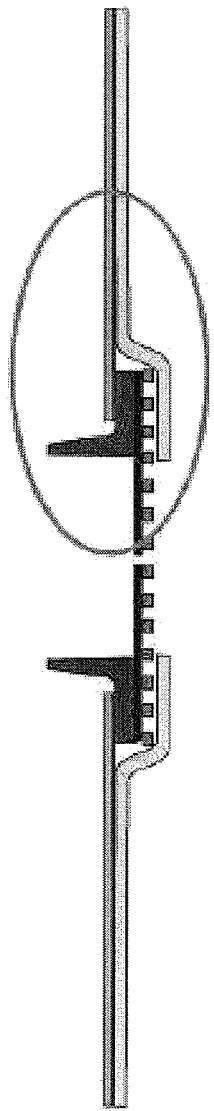
FIGS. 26A and 26B show another layered nasal device.
Figure 26B:
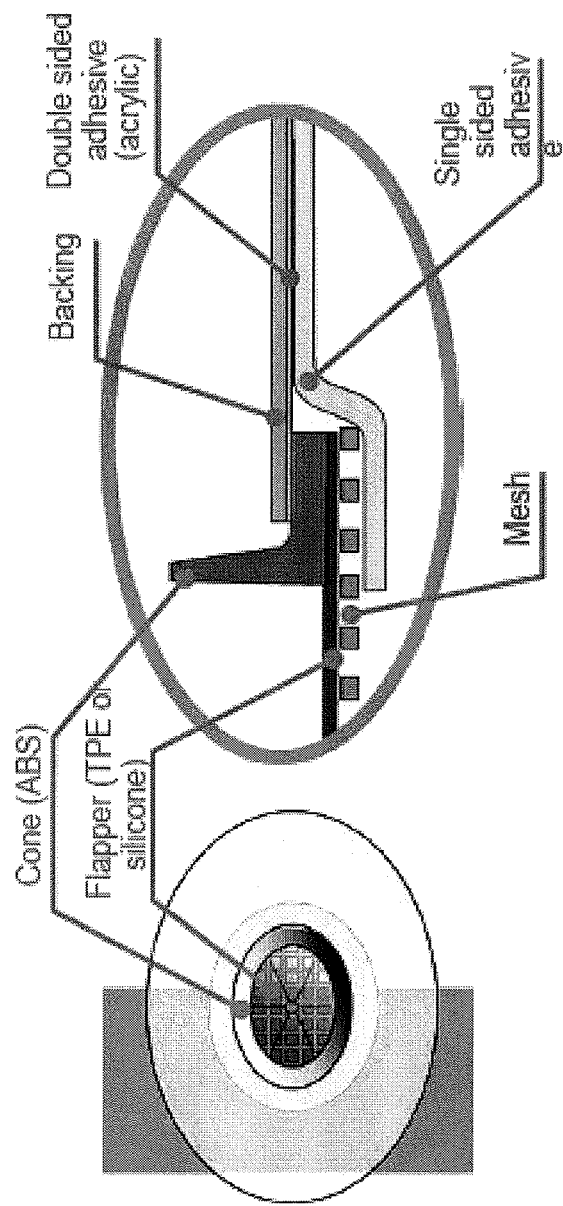

FIGS. 26A and 26B show another variation of a layered nasal device having an airflow resistor including a flap valve that is a pre-molded (e.g., formed by injection molding) and includes a conical alignment guide. This may be seen in the cross-section shown in FIG. 26A, and in the detail in the circled region shown in FIG. 26B. The left side of FIG. 26B shows a top view of an adhesive nasal device.

This variation of the adhesive nasal device may be formed by cutting an opening into a backing layer that protects one side of double-sided adhesive (forming the adhesive holdfast), inserting the pre-molded flap valve and cone subassembly into the opening, applying the flap valve limiter (mesh) over the flap valve, and securing another (single-sided) adhesive layer having a corresponding opening around the airflow resistor to secure the mesh, valve and cone in position.

Figures 26C, 26D, 26E:
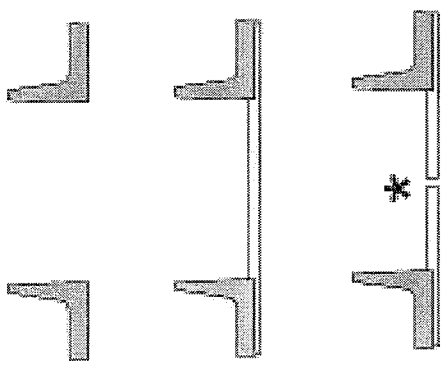
FIGS. 26C-26E illustrate one method of injection molding the subassembly including the cone and flap valve.
Figure 27A:
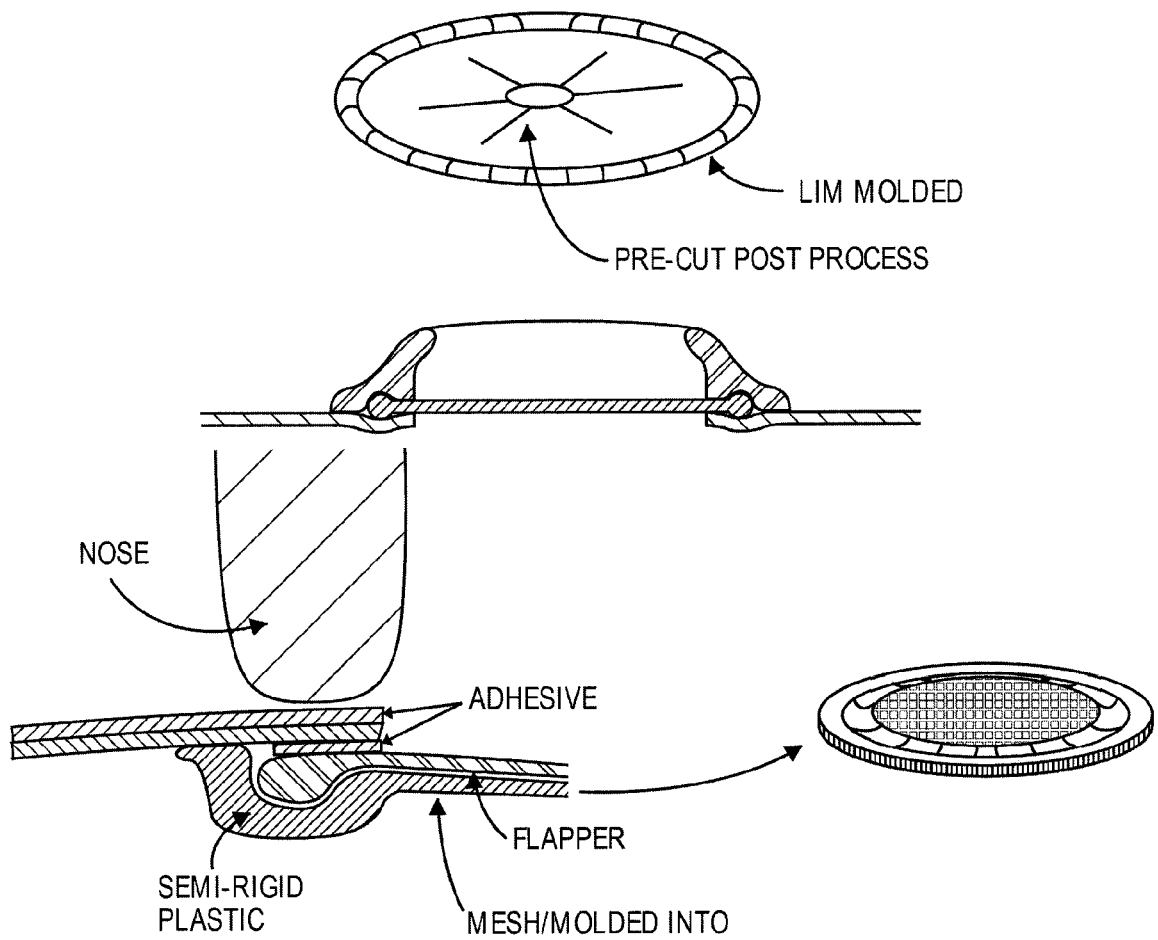

FIGS. 26C-26D illustrate one method of injection molding the subassembly including the cone and flap valve. In this example, the cone is first injection molded (in FIG. 26C), and then the flap valve layer is injection molded (or LIM molded) within the cone to a thickness of approximately 0.003" (in FIG. 26D). Finally, the flap valve leaflets are die cut from the molded flap valve layer (in FIG. 26E). FIGS. 27A-27C also show different views of a device having an injection molded flap valve.

Figure 28C:
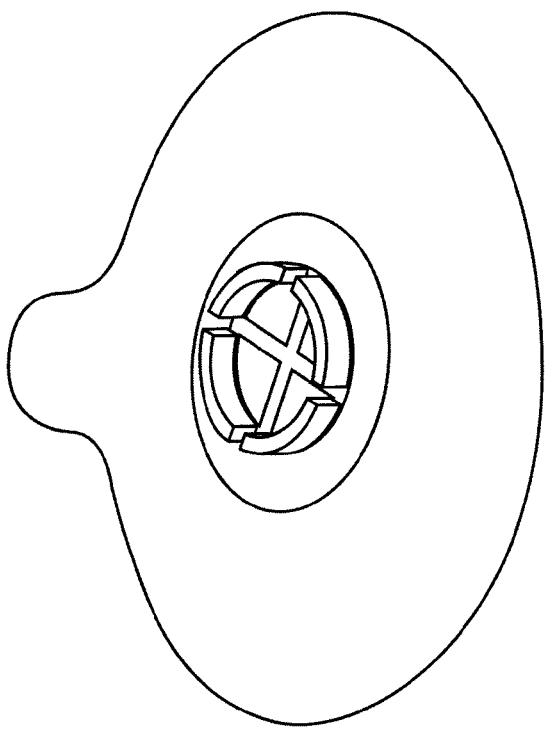
Figure 28B:
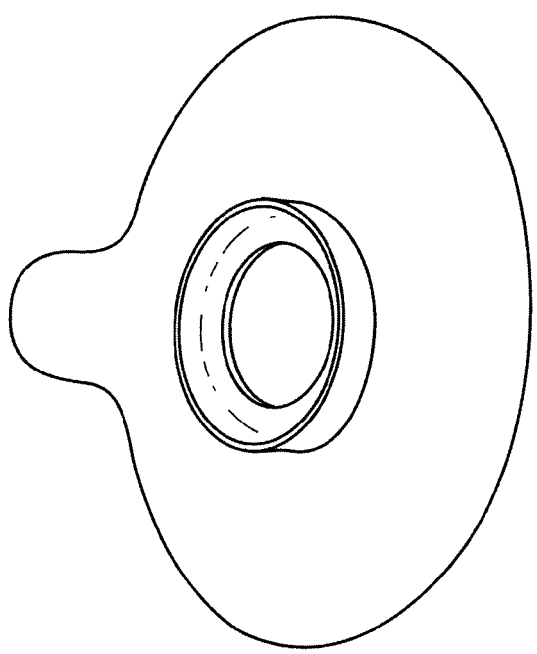

FIG. 28A includes an exploded view of an adhesive nasal device in which the airflow resistor is includes a stiff (e.g., die cut or injection molded) plastic piece that secure the flap valve and acts as the flap valve limiter. This airflow resistor subassembly can be secured within a cut-out region of an adhesive holdfast to form the adhesive nasal device. FIGS. 28B and 28C show bottom and top views, respectively, of this variation. The stiff subassembly may also act to prop open the nasal passages, as well as acting as an alignment guide.

Figure 29C:
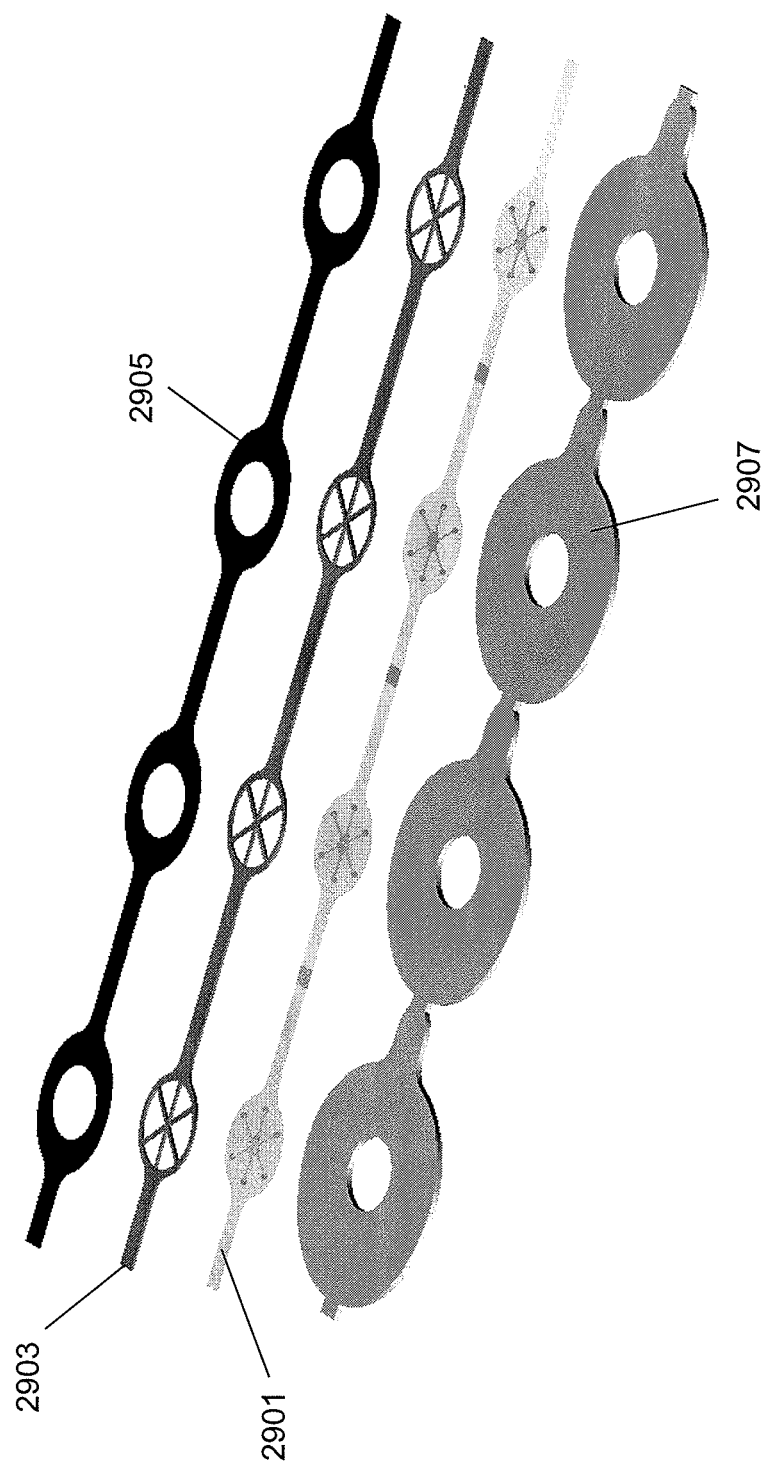
FIG. 29C illustrates a first method of fabrication a layered nasal device.
Figure 29D:
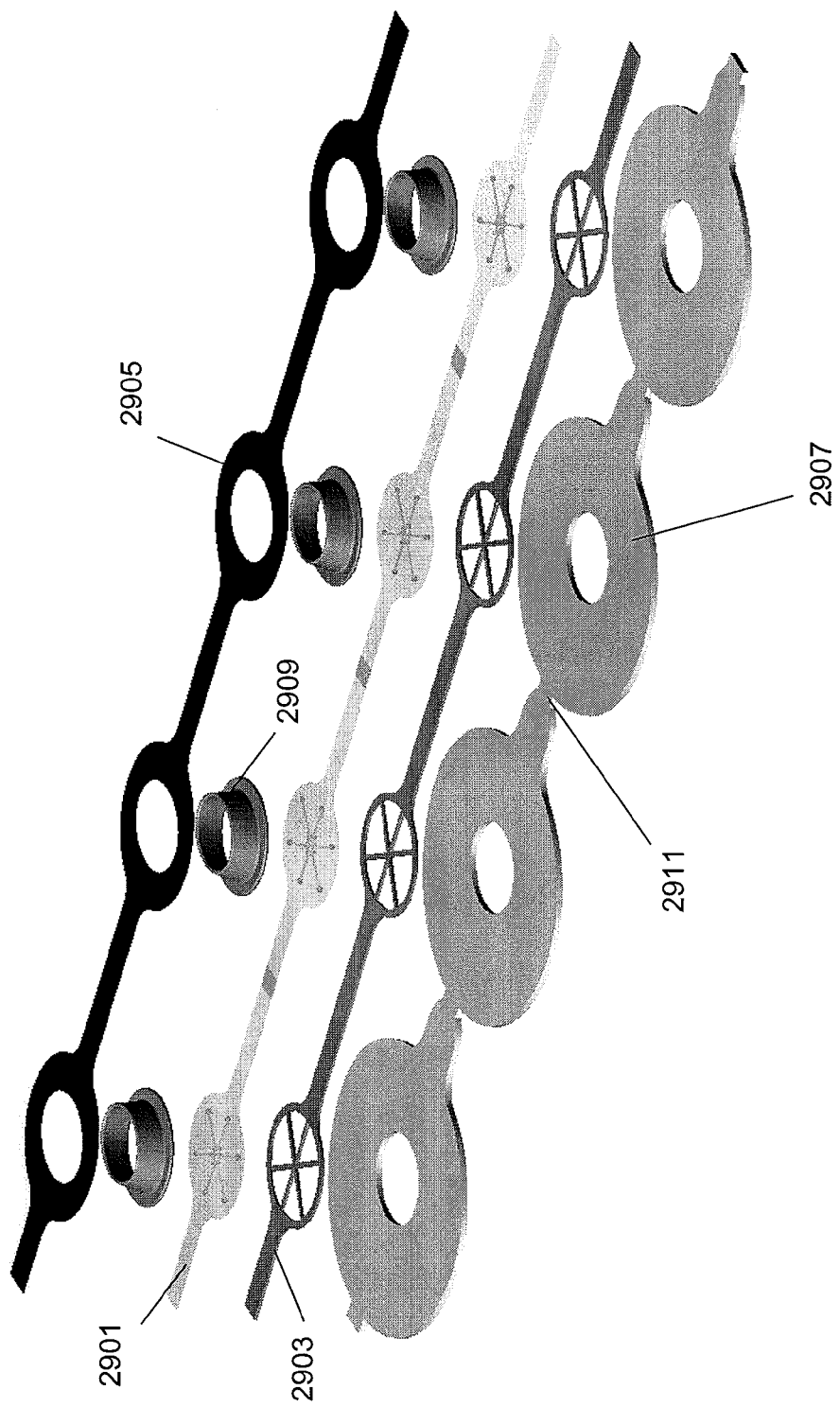
FIG. 29D illustrates another method of fabricating a layered nasal device.

FIGS. 29A and 29B show exploded views of layered nasal devices having slightly different arrangements of the layers. For example, in FIG. 29B, an additional adhesive layer is present between the flap valve limiter and the flap valve, compared with the adhesive nasal device shown in FIG. 29A. These exploded views may help indicate the general method of fabrication of the devices described herein. FIGS. 29C and 29D illustrate possible methods of fabricating exemplary layered nasal devices.

The devices described herein may be batch fabricated, or fabricated by hand. In particular, the layered devices described herein may be fabricated by sequentially layering various to form the final device. A layer maybe pre-processed by cutting, trimming, etc., or otherwise modifying it. Batch processing may be performed by layering strips or sheets corresponding to the different layers, and cutting or stamping the devices out of the strips or sheets after they have been at least partially assembled. FIGS. 29C and 29D schematically illustrate one method of fabricating devices from layered strips. For example, in FIG. 29C, the layers forming the device may be sequentially added after each layer has been formed. The adhesive holdfast layer 2907 (comprising an adhesive substrate and an adhesive) may be formed by, for example, cutting a continuous strip of annular shapes that are initially connected 2911, as shown. The layered airflow resistor may then be formed by cutting the flap valve leaflets from a flap valve substrate (e.g., a silicone layer) to form a flap valve layer 2901 that is also a continuous strip of connected flap valves, and placing the flap valve layer adjacent to a flap valve liming layer 2903. This layered airflow resistor may then be attached to the adhesive holdfast layer by an adhesive ring 2905. Once the layers have been assembled, the individual flap valves may be separated by cutting or otherwise removing the connecting region 2911. A similar process is illustrated in FIG. 29D, except the devices fabricated also include an aligner, shown here as a conical aligner 2909. The order of the layers in FIG. 29D is different than the arrangement shown in FIG. 29C. In FIG. 29D the skin-contacting surface of the adhesive holdfast is visible (facing "up" out of the page) and the flap valve limiter is between the flap valve layer and the adhesive substrate. In FIG. 29C, the skin-contacting surface of the adhesive holdfast is not visible (facing "down," out of the page) and the flap valve layer is between the flap valve limiter layer and the adhesive holdfast layer.

Figure 30:
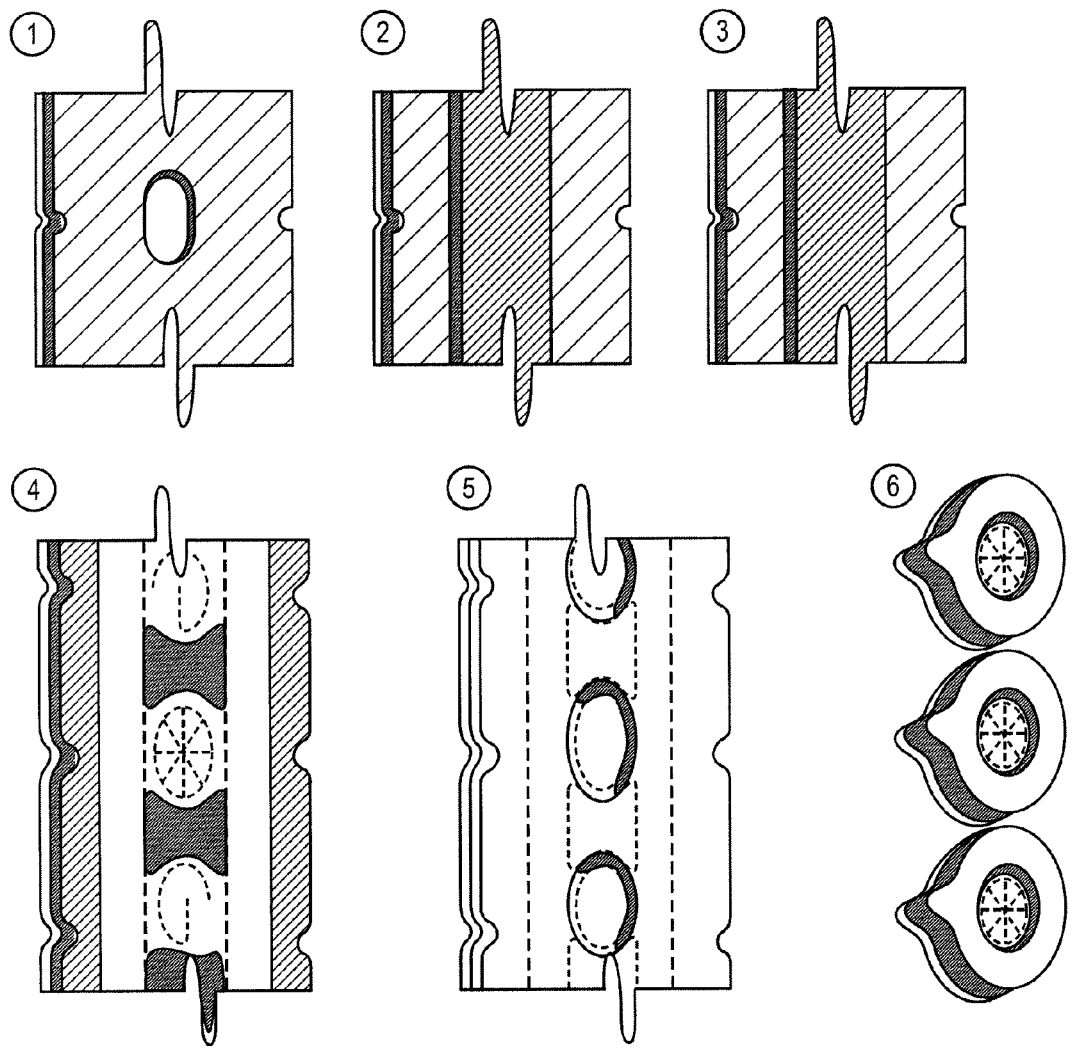

In one variation, a nasal adhesive device may be fabricated by forming each layer (e.g., but cutting the adhesive holdfast substrate, the flap leaflets, etc.), and by placing the positing the flap valve limiter adjacent to the flap valve layer and adhesively securing the layers (using, for example, an adhesive ring). As described in one of the examples below, the flap valve leaflets may be formed of the adhesive substrate layer. A continuous fabrication process may include layering the device as part of a rolling strip of materials that are sequentially layered, as shown in FIG. 30. In FIG. 30(1), openings are punched or cut form the adhesive holdfast layer that consists of a double-sided tape substrate and a removable backing layer. In step (2), a strip of flap valve material is applied, and the flap valve material is cut (e.g., die cut) to form the flap leaflets in step (3). The mesh (flap valve limiter) layer is applied in step (4) so that the mesh is aligned with the openings and the flap valves. An additional adhesive layer is applied in step (5) to seal the airflow resistor within the opening of the adhesive holdfast, and the individual adhesive nasal devices may be cut from the strip, as shown in step (6). FIG. 31 shows a similar fabrication method. Other batch fabrication methods were illustrated previously for some of the variations described above, for example in FIGS. 20A-20G, FIGS. 22A-22E, and FIGS. 24A-24F.

Figure 32A:
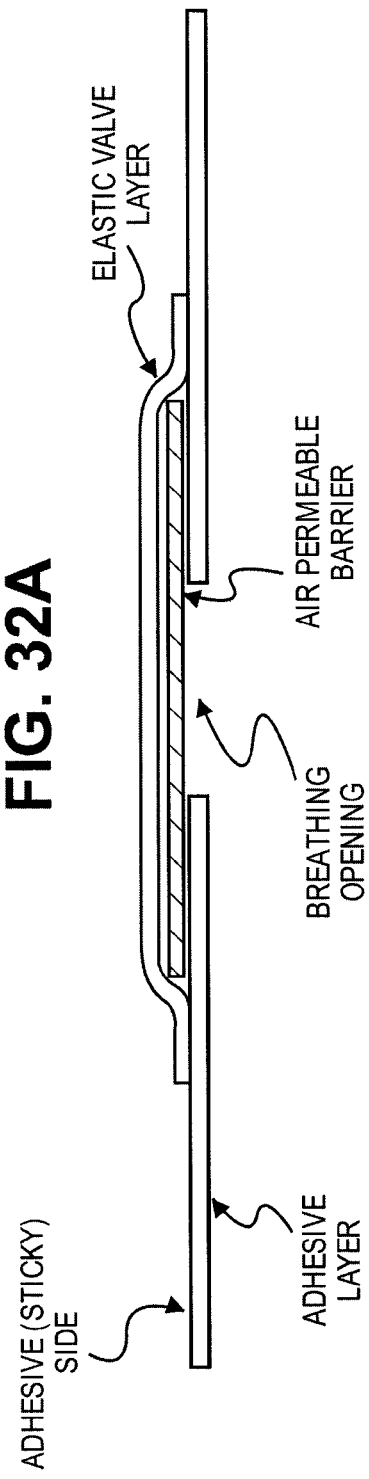
FIGS. 32A-32D show another variation of a layered nasal device.
Figure 32B:
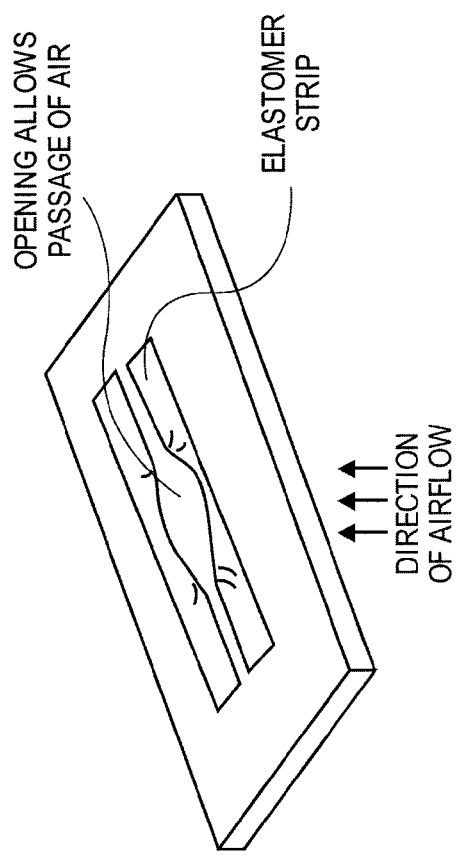
Figure 32C:
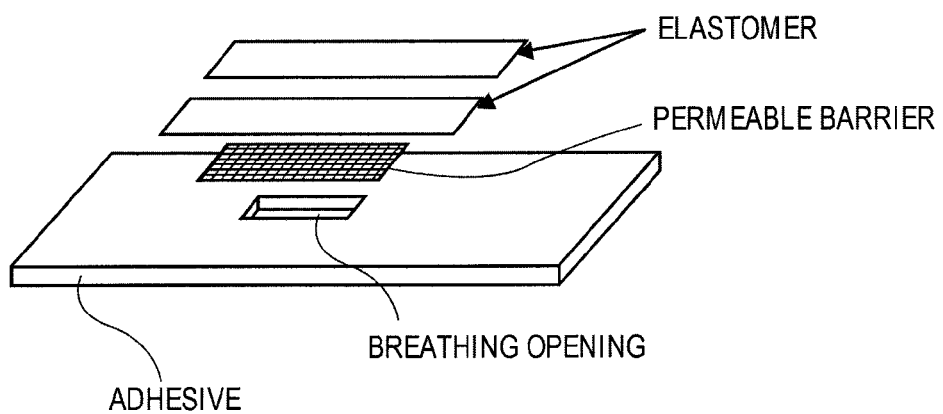
Figure 32D:
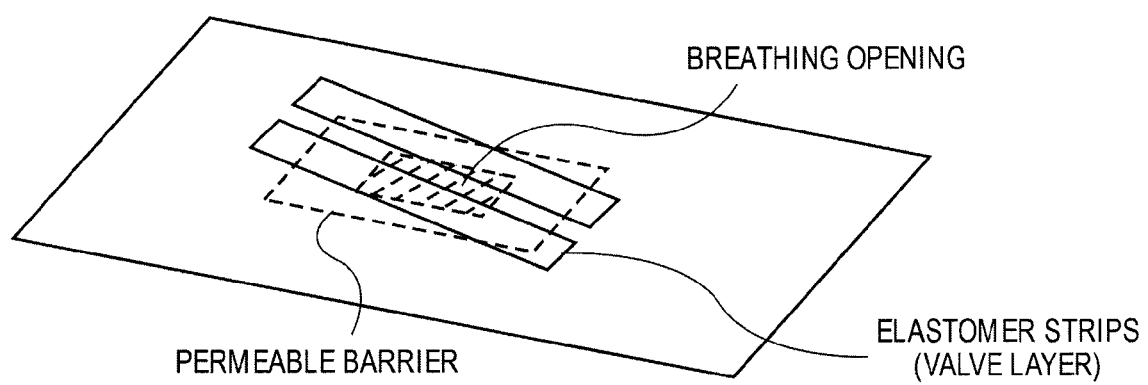

FIGS. 32A-32D show another variation of a layered nasal device. This device is a multi-layered layered device. The device shown has three layers: an adhesive (adhesive holdfast) layer, an air permeable barrier (the valve limiting layer), and the elastomeric valve layer. These layers are shown in FIG. 32A. FIGS. 32A and 32B show the arrangement of these layers to form the adhesive nasal device. The adhesive layer forms a substrate onto which the airflow resistor layers (the air permeable barrier and the elastomer) are secured. As in the previous examples, an opening through the adhesive holdfast is covered with an air permeable layer, such as a mesh. The edges of this layer may be secured to the adhesive layer by any appropriate method (including using the adhesive of the adhesive layer, or an additional adhesive). Two parallel strips of elastomeric material are placed adjacent to the air permeable layer spanning the opening, and secured at the ends (and possibly along one side). A gap (forming the leak pathway) may be left between the two strips, as shown in FIG. 32D. In some variations, multiple strips may be used to form the valve (e.g., see FIG. 2E-2G).

This adhesive nasal device may be placed in communication with a subject's nostril(s) so that when the subject inhales, the elastomeric bands forming the valve flex away from the air-permeable layer (the valve limiting layer), and open to allow air to flow with only minimal resistance. This is illustrated in FIG. 32B. During expiration, the strips of elastomeric material forming the valve are limited from flexing by the valve limiting layer formed from the air-permeable barrier, resulting in a resistance to expiration, as air is only allowed to pass through the leak pathway between the strips forming the valve layer.

The device shown in FIGS. 32A-32D, and any of the devices described herein, may be used to treat medical conditions including snoring, and typically can be worn by a subject to provide a small resistance to expiration (e.g., between about 2 and about 20 cm $H_2O$, between about 2 and about 8 cm $H_2O$, between about 2 and about 6 cm $H_2O$, or about 4 cm $H_2O$).

Figure 33B:
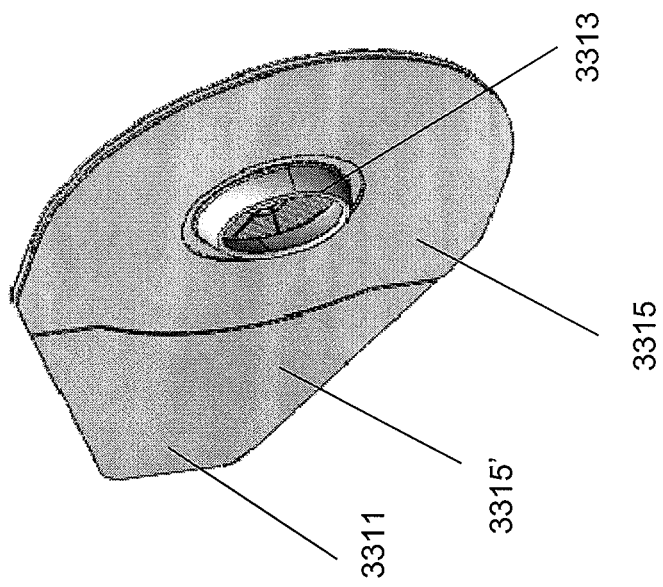
FIGS. 33A and 33B show front and back perspective views, respectively, of one variation of an adhesive layered nasal device as described herein.
Figure 33A:
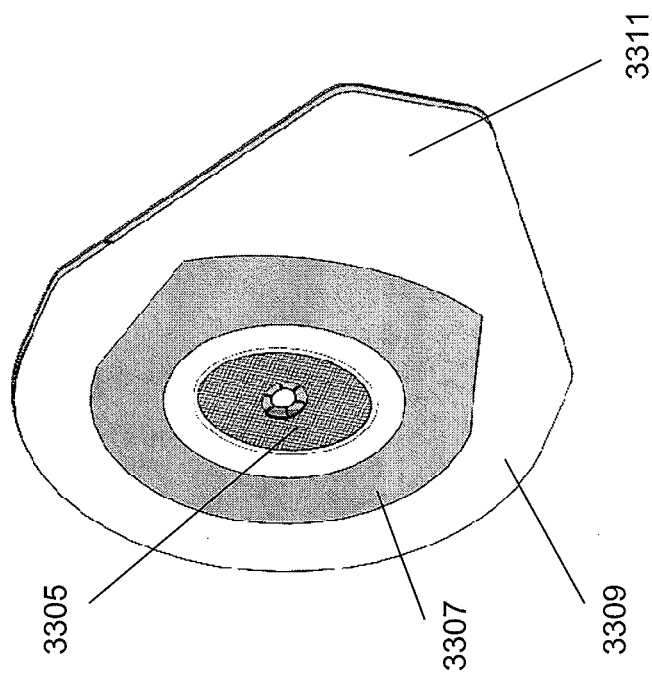

FIGS. 33A and 33B illustrate another example of a layered nasal device. FIG. 33A shows a front view of the device. The device includes an adhesive holdfast region that includes a tab or handle 3311 portion. The adhesive holdfast is a layer that surrounds an airflow resistor region that (in this example) includes a flap valve and a flap valve limiter. The flap valve limiter is visible in FIG. 33A as layer 3305, as is a portion of the adhesive substrate 3307. In this example, the adhesive substrate is formed from a thin film of material, and the airflow resistor is a flap valve that is formed in the adhesive substrate layer, as will be more readily apparent in the exploded view of FIG. 33C. The thin film of material (e.g., silicone, polyurethane, or other thin film material) may be very flexible, and may include (or be coated with) an adhesive material permitting the adhesive holdfast to comfortably conform to a subject's nasal region.

Figure 33C:
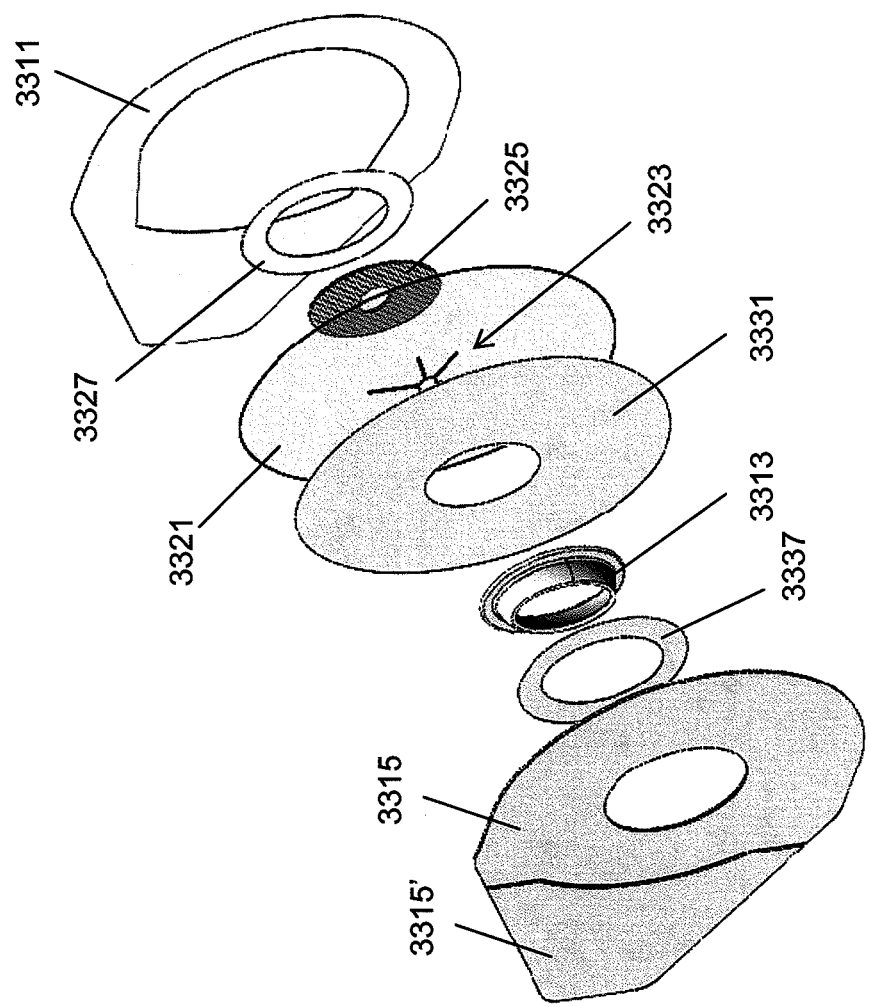
FIG. 33C shows an exploded perspective view of the device shown in FIGS. 33A and 33B.

The device in FIG. 33A also includes a support frame 3309. The support frame 3309 may help support the thin film of the adhesive substrate, preventing it from folding or wrinkling (or otherwise losing its shape) in an undesirable manner. The support frame may be adhesively attached to the adhesive substrate, and may be removed (similar to the protective coating region described above) from the device once it is positioned over the subject's nasal cavity. Removing the support frame may allow the device to conform (and perhaps seal) over a subject's nasal cavity. A support frame may extend across a portion of one side of the device (typically the side that does not contact the skin). In general, the support frame may extend to support at least three sides of the adhesive holdfast region, to maintain the general shape of the adhesive holdfast region. In some variations, the support frame covers the entire surface of the device (the side that does not contact the skin when the device is worn by a subject). A support frame may be made of any appropriate material, including the materials described above for the protective cover. The support frame may also be considered a layer, as shown in FIGS. 33A and 33C. The support frame may also include a handle or tab region to help facilitate removal of the support frame from device (e.g., by peeling it off) when the device is approximately positioned.

FIG. 33B shows the opposite side of the device shown in FIG. 33A. This side of the device may be referred to as the skin contacting side, since it typically includes the adhesive side of the adhesive holdfast, which is not visible beneath the protective cover 3315, 3315' in FIG. 33B. This protective cover 3315, 3315' has two regions that may be separately removed. The first region of the protective cover 3315 covers the adhesive holdfast around the airflow resistor, including the alignment guide 3313. A second protective cover 3315' covers the tab (or grip) region 3311. The first protective cover may be removed to position and initially attach the device to the subject (e.g., in communication with the subject's nasal cavity). The second protective cover 3315' can then be removed to further attach the tab region. Finally (in some variations), the support frame layer can then be removed from the opposite (outward facing) side to allow the device to completely adhere to the skin, as described above.

FIG. 33C shows an exploded view of the device shown in FIGS. 33A and 33B. In FIG. 33C, exposing individual layers. The central layer is the thin film adhesive substrate layer 3321. This layer is also the flap valve layer, and the central flap valve leaflets 3323 have been cut into the layer. A flap valve limiter layer 3325 is positioned adjacent to the flap valves, and secured in place with a ring of adhesive 3327. The support frame 3311 can be secured (e.g., via an adhesive) to the thin film of the adhesive substrate layer.

A layer of adhesive 3331 may be applied or otherwise secured to the opposite side of the thin film adhesive substrate. In some variations, both sides of the adhesive substrate are adhesive (or include an adhesive layer), or the thin film adhesive substrate is itself adhesive. An alignment guide 3313 may then be attached around the airflow resistor and secured to the layered adhesive holdfast by a ring of adhesive 3337 (e.g., a two-sided adhesive ring).

Method of Use

As previously mentioned, any of the layered adhesive devices described herein may be used to treat snoring or other sleep disordered breathing. A subject may apply the device to his or her own nose. For example, the devices may be first removed from clean or sterile packaging. The devices described herein may be sized (e.g., child/adult, small, medium, large, etc.), or one-size-fits-all. Placement of an adhesive nasal device may be done in front of a mirror or can occur without looking at a mirror. A device having an adhesive holdfast with a protective cover may be prepared for application by first removing the protective cover, and then aligning the airflow resistor (or alignment guide) with one or both nostrils (depending on the device). The device may then be applied to the nostril (e.g., over the nostril) by pushing the adhesive holdfast against the nostril to secure the airflow resistor in communication with the nostril(s). After placement of the adhesive nasal devices, the user may test whether an adequate seal has been created or has been maintained between the adhesive holdfast and the region in, on, over or around the nostrils through a variety of methods. On exhalation for example, it will be clear to the user whether a good seal has been created between the device and his nasal cavity because exhalation will be more difficult. Similarly, the device may be removed by peeling the adhesive holdfast away from the nostril.

An adhesive nasal device is typically worn over each nostril so that the airflow resistor allows airflow through the nostrils to be substantially unaffected by inspiration, but provides resistance to expiratory airflow through the nose. However, it may be advantageous to reverse this arrangement to inhibit inspiratory airflow and allow expiratory airflow to occur through the nose without substantial resistance. In some variations, an airflow resistor may be worn on only one nostril so that there is a resistance to airflow during expiration in only one nostril and there is no significant resistance to inspiration or exhalation through the other nostril. In one variation, a device having a fixed resistance (to both inspiration and expiration) could be worn by over, around or in one nostril, while the other nostril is in communication with an airflow resistor configured to have little inspiratory resistance and significant expiratory resistance. In some variation the device(s) may be worn or configured so that there is a greater resistance to airflow during inspiration in one nostril, and a greater resistance to airflow during exhalation in the other nostril. In general, however, it is believed that providing a slight resistance to airflow during expiration in both nostrils may be used to treat snoring or other sleep disordered breathing.

Figure 34A:
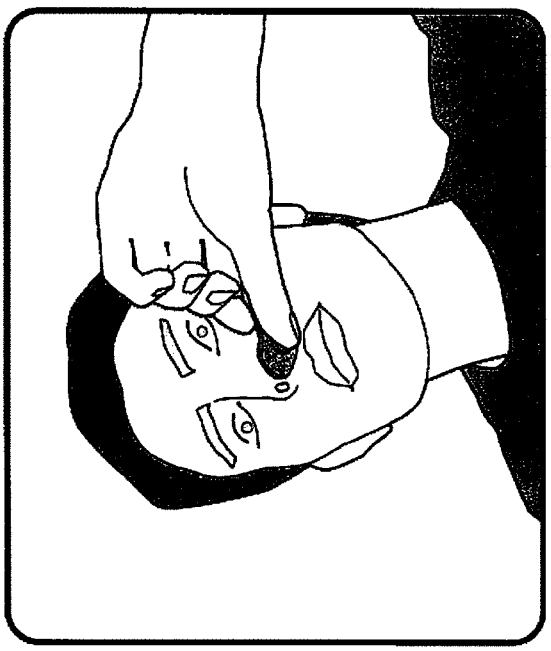
FIGS. 34A and 34B illustrate one exemplary method of using an adhesive nasal device.
Figure 34B:
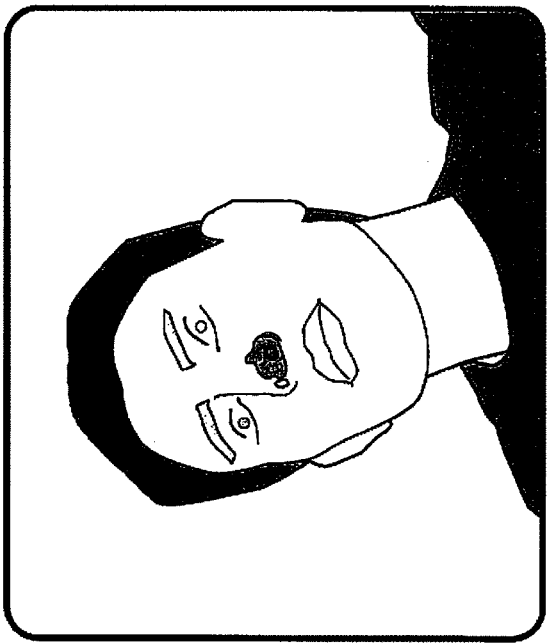

FIGS. 34A and 34B illustrate how an adhesive single-nostril nasal device such as those described above. In FIG. 34A, a user may first peel off all (or a part of) the protective cover, exposing the adhesive holdfast region. The user may then place the device over one of the nostrils, so that the passageway through the device is aligned with the nasal openings. An alignment guide may help the user to align the nasal opening and the central passageway of the device. The locating ring may have a texture, color, or shape that the user can feel, helping to position the device correctly. For example, the alignment guide may be a locating ring that is a thermoformed ring. The adhesive device may be applied against the nostril to secure it into position. The user may first wash the area to which the adhesive device will be applied to remove material (e.g., dirt, oils, etc.) that could prevent adhesion (and/or a seal) between the adhesive device and the nostril and/or nose.

Once a single-nostril device has been applied over one nostril (as shown in FIG. 34B), a second device may be applied to the other nostril. The adhesive holdfast regions of the two devices may overlap. To remove the devices, the user may simply peel off the adhesive devices. In some cases, as one device is removed, it will facilitate removal of the second device since the two once-independent devices may be adhered together. While the methods and devices have been described in some detail here by way of illustration and example, such illustration and example is for purposes of clarity of understanding only. It will be readily apparent to those of ordinary skill in the art in light of the teachings herein that certain changes and modifications may be made thereto without departing from the spirit and scope of the invention.

What is claimed is:

1. A layered nasal device adapted to be adhesively secured in communication with a subject's nasal cavity, the device comprising:
a layered airflow resistor configured to inhibit exhalation more than inhalation, wherein the layered airflow resistor comprises a flap valve adjacent to a flap valve limiting layer
at least one leak pathway through the device through which air may pass even when the airflow resistor is closed; and
an adhesive holdfast layer configured to secure the layered airflow resistor in communication with the subject's nasal cavity.

2. The device of claim 1, wherein the airflow resistor layer is disposed substantially in the plane of the adhesive holdfast layer.

3. The device of claim 1, wherein the adhesive holdfast layer comprises a flexible substrate and a biocompatible adhesive.

4. The device of claim 1, wherein the layered airflow resistor comprises the at least one leak pathway.

5. The device of claim 1, wherein the flap valve comprises a plurality of valve leaflets.

6. The device of claim 1, wherein the flap valve is part of a flap valve layer.

7. The device of claim 1, wherein the flap valve comprises a plurality of valve leaflets formed in a flap valve layer.

8. The device of claim 1, wherein the flap valve comprises a plurality of valve leaflets configured to open from a central point.

9. The device of claim 1, wherein the flap valve is formed from the adhesive holdfast layer.

10. The device of claim 1, wherein the flap valve comprises silicone or polyurethane.

11. The device of claim 1, wherein the flap valve limiting layer comprises a mesh.

12. The device of claim 1, further comprising an alignment guide.

13. The device of claim 12, wherein the alignment guide comprises a ring.

14. The device of claim 12, wherein the alignment guide comprises a conical alignment guide.

15. The device of claim 1, further comprising a tactile alignment guide.

16. The device of claim 1, further comprising a visual alignment guide.

17. The device of claim 1, further comprising a support frame.

18. A layered nasal device adapted to be adhesively secured in communication with a subject's nasal cavity, the device comprising:
a layered airflow resistor configured to inhibit exhalation more than inhalation, wherein the layered airflow resistor comprises a flap valve adjacent to a flap valve limiter and a leak pathway through the flap valve through which air may pass even when the airflow resistor is closed;
a layered adhesive holdfast comprising
a substrate layer, and
a layer of biocompatible adhesive.

19. The device of claim 18, wherein the layered adhesive holdfast at least partially surrounds the layered airflow resistor.

20. The device of claim 18, further comprising an alignment guide selected from the group consisting of: a ring, a conical alignment guide, a tactile alignment guide, and a visual alignment guide.

21. The device of claim 18, further comprising a support frame.

22. The device of claim 18, further comprising a support frame layer.

23. The device of claim 18, wherein the flap valve is formed from the substrate layer of the layered adhesive holdfast.

24. The device of claim 18, wherein the flap valve comprises a plurality of valve leaflets configured to open from a central point.

25. The device of claim 18, wherein the flap valve limiter is selected from the group consisting of: a mesh, a strut, a plurality of struts, and a plurality of partial struts.

26. The device of claim 1, wherein the layered nasal device is generally planar.

27. The device of claim 1, wherein the layered nasal device is flexible.

28. An adhesive nasal device that is adapted to be secured in communication with a subject's nasal cavity, the device comprising:
   an airflow resistor configured to inhibit exhalation more than inhalation
   a leak pathway through the flap valve through which air may pass even when the airflow resistor is closed; and
   a flexible adhesive holdfast layer configured to secure the airflow resistor in communication with the subject's nasal cavity, wherein the adhesive holdfast layer extends at least partially around the airflow resistor.

29. The device of claim 28, further comprising an alignment guide.

30. The device of claim 28, wherein the airflow resistor comprises a layered airflow resistor that is substantially planar.

31. The device of claim 28, wherein the airflow resistor includes a layered airflow resistor comprising a flap valve layer and a valve limiter.

32. The device of claim 28, wherein the adhesive nasal device is configured to be secured over both of a subject's nostrils.

33. The device of claim 28, wherein the flexible adhesive holdfast layer extends away from the airflow resistor and is configured to form a seal around one or both of the subject's nostrils.

34. The device of claim 28, wherein the flexible adhesive holdfast layer comprises a substrate layer and a biocompatible adhesive.

35. The device of claim 28, wherein the adhesive nasal device is generally flat and configured to be secured over at least one of a subject's nostrils.

36. The device of claim 28, wherein the layered nasal device is generally planar.

37. A layered nasal device that is generally planar and is adapted to be adhesively secured in communication with a subject's nasal cavity, the device comprising:
   a layered airflow resistor configured to inhibit exhalation wore than inhalation, wherein the layered airflow resistor comprises a flap valve adjacent to a flap valve limiting layer and a leak pathway through which air may pass even when the airflow resistor is closed; and
   an adhesive holdfast layer extending at least partially around the layered airflow resistor and configured to secure the layered airflow resistor in communication with the subject's nasal cavity.

38. The device of claim 1, wherein the device has a resistance exhalation of between 0.01 and 100 cm of $H_2O$ measured at a flow rate of 100 ml/sec.

39. The device of claim 18, wherein the device has a resistance exhalation of between 0.01 and 100 cm of $H_2O$ measured at a flow rate of 100 ml/sec.

40. A layered nasal device adapted to be adhesively secured in communication with a subject's nasal cavity, the device comprising:
   a layered airflow resistor configured to inhibit exhalation more than inhalation, wherein the layered airflow resistor comprises a flap valve adjacent to a flap valve limiting layer;
   at least one leak pathway through the device through which air may pass during exhalation; and
   an adhesive holdfast layer configured to secure the layered airflow resistor in communication with the subject's nasal cavity.

* * * * *